(12) United States Patent
Loh et al.

(10) Patent No.: US 9,079,824 B2
(45) Date of Patent: Jul. 14, 2015

(54) METHOD FOR THE SYNTHESIS OF AN AMINO ACETAL

(75) Inventors: Teck Peng Loh, Singapore (SG); Jiesheng Tian, Singapore (SG)

(73) Assignee: Nanyang Technological University, Singapore (SG)

(*) Notice: Subject to any disclaimer, the term of this patent is extended or adjusted under 35 U.S.C. 154(b) by 369 days.

(21) Appl. No.: 13/808,228

(22) PCT Filed: Jul. 6, 2011

(86) PCT No.: PCT/SG2011/000239
§ 371 (c)(1),
(2), (4) Date: Mar. 11, 2013

(87) PCT Pub. No.: WO2012/005693
PCT Pub. Date: Jan. 12, 2012

(65) Prior Publication Data
US 2013/0165682 A1 Jun. 27, 2013

Related U.S. Application Data

(60) Provisional application No. 61/361,846, filed on Jul. 6, 2010.

(51) Int. Cl.
| | |
|---|---|
| C07F 7/10 | (2006.01) |
| C07C 211/00 | (2006.01) |
| C07D 209/48 | (2006.01) |
| C07C 213/08 | (2006.01) |
| C07B 41/04 | (2006.01) |
| C07C 213/00 | (2006.01) |
| C07C 227/18 | (2006.01) |
| C07C 227/10 | (2006.01) |
| C07F 7/18 | (2006.01) |
| C07B 59/00 | (2006.01) |
| C07C 213/02 | (2006.01) |

(52) U.S. Cl.
CPC .............. *C07C 213/08* (2013.01); *C07B 41/04* (2013.01); *C07B 59/001* (2013.01); *C07C 213/00* (2013.01); *C07C 213/02* (2013.01); *C07C 227/10* (2013.01); *C07C 227/18* (2013.01); *C07D 209/48* (2013.01); *C07F 7/1844* (2013.01); *C07F 7/1892* (2013.01)

(58) Field of Classification Search
CPC .......................... C07F 7/1844; C07C 227/18
USPC ............................ 556/418; 564/457; 548/477
See application file for complete search history.

(56) References Cited

U.S. PATENT DOCUMENTS 2,425,628 A 8/1947 Loder et al.

OTHER PUBLICATIONS

Graham et al., Org. Biomol. Chem., 2003, 1, 834-849.*
Aboelella et al., "Effects of Thioether Substituents on the $O_2$ Reactivity of β-Diketiminate-Cu(I) Complexes: Probing the Role of the Methionine Ligand in Copper Monooxygenases," *J. Am. Chem. Soc.* 128: 3445-3458, 2006.
Alberico et al., "Aryl-Aryl Bond Formation by Transition-Metal-Catalyzed Direct Arylation," *Chem. Rev.* 107: 174-238, 2007.
Anderson et al., "Investigation of the importance of nitrogen substituents in a N-P chiral ligand for enantioselective allylic alkylation," *Tetrahedron: Asymmetry* 12: 923-935, 2001.
Bhat et al., *Chemistry of Natural Products*, Alpha Science Int'l Ltd., 2005, Chapter 5, "Amino Acids, Proteins and Bioconversions," pp. 317-393.
Block, "The Isolation and Synthesis of the Naturally Occurring α-Amino Acids," *Chem. Rev.* 38(3): 501-571, 1946.
Breuer et al., "Industrial Methods for the Production of Optically Active Intermediates," *Angew. Chem. Int. Ed.* 43: 788-824, 2004.
Campeau et al., "Palladium-catalyzed direct arylation of simples arenes in synthesis of biaryl molecules," *Chem. Commun.*: 1253-1264, 2006.
Chen et al., "Cu(II)-Catalyzed Functionalizations of Aryl C-H Bonds Using $O_2$ as an Oxidant," *J. Am. Chem. Soc.* 128: 6790-6791, 2006.
Ciblat et al., "A Modular Approach to Marine Macrolide Construction. 4. Assembly of C36-C51 and C29-C44 Building Blocks and Evaluation of Key Coupling Reactions Targeting Spongistatin 1 (Altohyrtin A)," *Organic Letters* 9(4): 719-722, 2007.
Curphey et al., "C-Alkylation of Aldehyde Enamines," *Chemical Communications* 369: 510, 1967.
Curphey et al., "A Study of the Alkylation of Enamines Derived from Sterically Hindered Amines," *J. Org. Chem.* 40(5): 607-614, 1975.
Daugulis et al., "Regioselective Functionalization of Unreactive Carbon-Hydrogen Bonds," *Synlett* 20: 3382-3388, 2006.
Davie et al., "Asymmetric Catalysis Mediated by Synthetic Peptides," *Chem. Rev.* 107: 5759-5812, 2007.
Davies, "Recent Advances in Catalytic Enantioselective Intermolecular C—H Functionalization," *Angew. Chem. Int. Ed.* 45: 6422-6425, 2006.
Davies, "Entwicklungen in der katalytischen enantioselektiven intermolekularen C—H-Funktionalisierung," *Angew. Chem.* 118: 6574-6577, 2006.
Dick et al., "Transition metal catalyzed oxidative functionalization of carbon-hydrogen bonds," *Tetrahedron* 62: 2439-2463, 2006.
Dyker, "Transition Metal Catalyzed Coupling Reactions under C—H Activation," *Angew. Chem. Int. Ed.* 38: 1698-1712, 1999.
Dyker, "Übergangsmetall-katalysierte Kupplungsreaktionen unter C—H-Aktivierung," *Angew. Chem.* 111: 1808-1822, 1999.
Fujii et al., "H-atom abstraction reaction for organic substrates via mononuclear copper(II)-superoxo species as a model for DβM and PHM," *Dalton Trans.*: 164-170, 2008.
Godula et al., "C—H Bond Functionalization in Complex Organic Synthesis," *Science* 312: 67-72, 2006.
Goj et al., "Developments in Catalytic Aromatic C—H Transformations: Promising Tools for Organic Synthesis," *Current Organic Chemistry* 9: 671-685, 2005.

(Continued)

*Primary Examiner* — Porfirio Nazario Gonzalez
*Assistant Examiner* — Kofi Adzamli
(74) *Attorney, Agent, or Firm* — Seed IP Law Group PLLC

(57) ABSTRACT

The present invention relates to a method for the synthesis of an α amino acetal, comprising (i) oxidizing a tertiary amine in the presence of a copper catalyst, at least one oxidant and a solvent, or (ii) reacting a secondary amine and an aliphatic aldehyde in the presence of a copper catalyst, at least one oxidant and a solvent.

19 Claims, 62 Drawing Sheets

(56) References Cited

OTHER PUBLICATIONS

Goldsmith et al., "Cleavage of Cyclic Esters by Magnesium Bromide-Acetic Anhydride. Sn2 Substitution at a Secondary Site," *J. Org. Chem.* 40(24): 3571-3574, 1975.

Graham et al., "Studies on the Lewis acid mediated cleavage of α-aminoacetals: synthesis of novel 1,2-aminoethers, and evidence for α-alkoxy aziridinium ion intermediates," *Org. Biol. Chem.* 1: 834-849, 2003.

Gröger, "Catalytic Enantioselective Strecker Reactions and Analogous Syntheses," *Chem. Rev.* 103: 2795-2827, 2003.

Hamada et al., "Copper-Catalyzed Aerobic Oxidative Amidation of Terminal Alkynes: Efficient Synthesis of Ynamides," *J. Am. Chem. Soc.* 130: 833-835, 2008.

Harada, "Asymmetric Synthesis of α-Amino-acids by the Strecker Synthesis," *Nature* 4912: 1201, 1963.

Helmchen et al., "Phosphinooxazolines—A New Class of Versatile, Modular P,N-Ligands for Asymmetric Catalysis," *Accounts of Chemical Research* 33(6): 336-345, 2000.

Hodgson et al., "Synthesis and C-Alkylation of Hindered Aldehyde Enamines," *J. Org. Chem.* 74: 1019-1028, 2009.

Huckstep et al., "A Convenient Method of Preparing the Leukotriene Precursor Methyl 5-Oxopentanoate," *Synthesis* 10: 881-882, Oct. 1982.

Ju et al., "Aqueous N-alkylation of amines using alkyl halides: direct generation of tertiary amines under microwave irradiation," *Green Chem.* 6: 219-221, 2004.

Ju et al., "Aqueous N-Heterocyclization of Primary Amines and Hydrazines with Dihalides: Microwave-Assisted Syntheses of N-Azacycloalkanes, Isoindole, Pyrazole, Pyrazolidine, and Phthalazine Derivatives," *J. Org. Chem.* 71: 135-141, 2006.

Kakiuchi et al., "Catalytic C-H/Olefin Coupling," *Accounts of Chemical Research* 35(10): 826-834, 2002.

Kakiuchi et al., "Catalytic Methods for C—H Bond Functionalization: Application in Organic Synthesis," *Adv. Synth. Catal.* 345: 1077-1101, 2003.

Kaneda et al., "Oxygenation of Enamines Using Copper Catalysts," *Journal of Molecular Catalysis* 15: 349-365, 1982.

King et al., "Mechanistic Study of Copper-Catalyzed Aerobic Oxidative Coupling of Arylboronic Esters and Methanol: Insights into an Organometallic Oxidase Reaction," *J. Am. Chem. Soc.* 131: 5044-5045, 2009.

Knowles, "Asymmetric Hydrogenation," *Acc. Chem. Res.* 16: 106-112, 1983.

Kuethe et al., "A Concise Synthesis of (S)-N-Ethoxycarbonyl-α-methylvaline," *J. Org. Chem.* 72: 7469-7472, 2007.

Lewis et al., "Reactivity of Dioxygen-Copper Systems," *Chem. Rev.* 104: 1047-1076, 2004.

Li et al., "CuBr-Catalyzed Direct Indolation of Tetrahydroisoquinolines via Cross-Dehydrogenative Coupling between $sp^3$ C—H and $sp^2$ C—H Bonds," *J. Am. Chem. Soc.* 127: 6968-6969, 2005.

Liang et al., "Contrasting Copper-Dioxygen Chemistry Arising from Alike Tridentate Alkyltriamine Copper(I) Complexes," *J. Am. Chem. Soc.* 124: 4170-4171, 2002.

Lucas et al., "Tolunene and Ethylbenzene Aliphatic C—H Bond Oxidations Initiated by a Dicopper(II)-µ-1,2-Peroxo Complex," *J. Am. Chem. Soc.* 131: 3230-3245, 2009.

Mahadevan et al., "Irreversible Reduction of Dioxygen by Simple Peralklated Diamine—Copper(I) Complexes: Characterization and Thermal Stability of a $[Cu_2(\mu-O)_2]^{2+}$ Core," *J. Am. Chem. Soc.* 119: 11996-11997, 1997.

Malhotra et al., "Autoxidation of Enamines and Schiff Bases of α,βUnsaturated Ketones. A New Synthesis of Unsaturated 1,4-Diones," *Journal of the American Chemical Society* 90(23): 6565-6566, Nov. 6, 1968.

Merino et al., "Organocatalyzed Strecker reactions," *Tetrahedron* 65: 1219-1234, 2009.

Miller, "Production of Some Organic Compounds under Possible Primitive Earth Conditions," *Journal of the American Chemical Society* 77(9): 2351-2361, 1955.

Mirica et al., "Structure and Spectroscopy of Copper-Dioxygen Complexes," *Chem. Rev.* 104: 1013-1045, 2004.

Miura et al., "Direct Arylation via Cleavage of Activated and Unactivated C—H Bonds," *Topics in Current Chemistry* 219: 211-241, 2002.

Mukherjee et al., "Chiral Counteranions in Asymmetric Transition-Metal Catalysis: Highly Enantioselective Pd/Brønsted Acid-Catalyzed Direct α-Allylation of Aldehydes," *J. Am. Chem. Soc.* 129: 11336-11337, 2007.

Nájera et al., "Catalytic Asymmetric Synthesis of α-Amino Acids," *Chem. Rev.* 107: 4584-4671, 2007.

Nam, "Guest Editorial—Dioxygen Activation by Metalloenzymes and Models," *Accounds of Chemical Research* 40(7): 465, Jul. 2007.

Park et al., "Thioether S-ligation in a side-on $\mu$-$\eta^2$:$\eta^2$-peroxodicopper(II) complex," *Chem. Commun.* 46: 91-93, 2010.

Phipps et al., "Cu(II)-Catalyzed Direct and Site-Selective Arylation of Indoles Under Mild Conditions," *J. Am. Chem. Soc.* 130: 8172-8174, 2008.

Prigge et al., "Dioxygen Binds End-On to Mononuclear Copper in a Precatalytic Enzyme Complex," *Science* 304: 864-867, May 7, 2004.

Punniyamurthy et al., "Recent Advances in Transition Metal Catalyzed Oxidation of Organic Substrates with Molecular Oxygen," *Chem. Rev.* 105: 2329-2363, 2005.

Ritleng et al., "Ru-, Rh-, and Pd-Catalyzed C—C Bond Formation Involving C—H Activation and Addition on Unsaturated Substrates: Reactions and Mechanistic Aspects," *Chem. Rev.* 102: 1731-1769, 2002.

Shu et al., "Synthesis of Enantiopure Fmoc-α-Methylvaline," *Organic Process Research & Development* 12: 298-300, 2008.

Smith et al., "Efficient, Selective, and Green: Catalyst Tuning for Highly Enantioselective Reactions of Ethylene," *Organic Letters* 10(8): 1657-1659, 2008.

Stahl, "Palladium Oxidase Catalysis: Selective Oxidation of Organic Chemicals by Direct Dioxygen-Coupled Turnover," *Angew. Chem. Int. Ed.* 43: 3400-3420, 2004.

Tian et al., "Copper-Catalyzed Rearrangement of Tertiary Amines through Oxidation of Aliphatic C—H Bonds in Air or Oxygen: Direct Synthesis of α-Amino Acetals," *Angew. Chem. Int. Ed.* 49: 8417-8420, 2010.

Tian et al., "Copper-catalyzed α-amination of aliphatic aldehydes," *Chem. Commun.* 47: 5458-5460, 2011.

Tsantrizos, "Peptidomimetic Therapeutic Agents Targeting the Protease Enzyme of the Human Immunodeficiency Virus and Hepatitis C Virus," *Accounts of Chemical Research* 41(10): 1252-1263, Oct. 2008.

Tsuchimoto et al., "Zirconium Triflate Catalyzed Direct Coupling Reaction of Lactams with Heterocyclic Arenes under Atmospheric Oxygen," *Angew. Chem. Int. Ed.* 43: 4231-4233, 2004.

Wang et al., "Expanding the Genetic Code," *Angew. Chem. Int. Ed.* 44: 34-66, 2005.

Würtele et al., "Aliphatic C—H Bond Oxidation of Toluene Using Copper Peroxo Complexes That Are Stable at Room Temperature," *J. Am. Chem. Soc.* 131: 7544-7545, 2009.

Yu et al., "σ-Chelation-directed C—H functionalizations using Pd(II) and Cu(II) catalysts: regioselectivity, stereoselectivity and catalytic turnover," *Org. Biomol. Chem.* 4: 4041-4047, 2006.

Zhang et al., "Dioxygen Activation under Ambient Conditions: Cu-Catalyzed Oxidative Amidation-Diketonization of Terminal Alkynes Leading to α-Ketoamides," *J. Am. Chem. Soc.* 132: 28-29, 2010.

Zuend et al., "Scaleable catalytic asymmetric Strecker syntheses of unnatural α-amino acids," *Nature* 461: 968-971, Oct. 15, 2009.

\* cited by examiner (A)

(B)

(A)

(B)

(Scheme 1)

(Scheme 2)

(Scheme 3)

(Scheme 6)

(Scheme 7)

(Scheme 8)

METHOD FOR THE SYNTHESIS OF AN AMINO ACETAL

CROSS-REFERENCE TO RELATED APPLICATION

This application claims the benefit of priority of U.S. Provisional Patent Application No. 61/361,846, filed 6 Jul. 2010, the contents of which being hereby incorporated by reference in its entirety for all purposes.

TECHNICAL FIELD

The invention relates to a method for the synthesis of an amino acetal, and in particular, an α-amino acetal (alpha-amino acetal) having the amino group formed at the α-position of the acetal.

BACKGROUND

Many natural products or bio-molecules contain α-amino acid or α-amino alcohol units in their structures. While these units may be obtained from naturally occurring α-amino acids, general methods to obtain other non-natural α-amino acids are highly sought-after. Direct synthesis of α-amino acids from air by means of biomimetic methods has been regarded as one of the most challenging tasks. The biological method involving copper enzymatic activation of dioxygen has attracted considerable attention, owing to the existence of important copper mono-oxygenases. Mimicking this system to study copper-dioxygen interactions and further applications of dioxygen-copper systems in organic synthesis, especially in the developments of aliphatic C—H bond oxidation or C—H bond amination chemistry, has attracted tremendous interest. For C—H bond activation, dioxygen-copper systems provide an alternative to the commonly employed methods which use expensive metal catalysts and stoichiometric metal oxidants.

SUMMARY

Various embodiments of the present invention provide for a direct synthesis method of forming α-amino acetals by employing less expensive copper catalysts and oxidants to oxidize the starting amine compounds. Yields as high as 80% (based on the starting amine compounds) have been achieved via the present method.

Various embodiments of the invention provide for a method for the synthesis of an α-amino acetal, comprising (i) oxidizing a tertiary amine in the presence of a copper catalyst, at least one oxidant and a solvent, or (ii) reacting a secondary amine and an aliphatic aldehyde in the presence of a copper catalyst, at least one oxidant and a solvent.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

(tert-butyldimethylsilyloxy)-3-methylbutan-2-yl)(isopropyl)amino)-5,5-dimethoxypentanoate (2j) of Example 1.

Figure 21A:
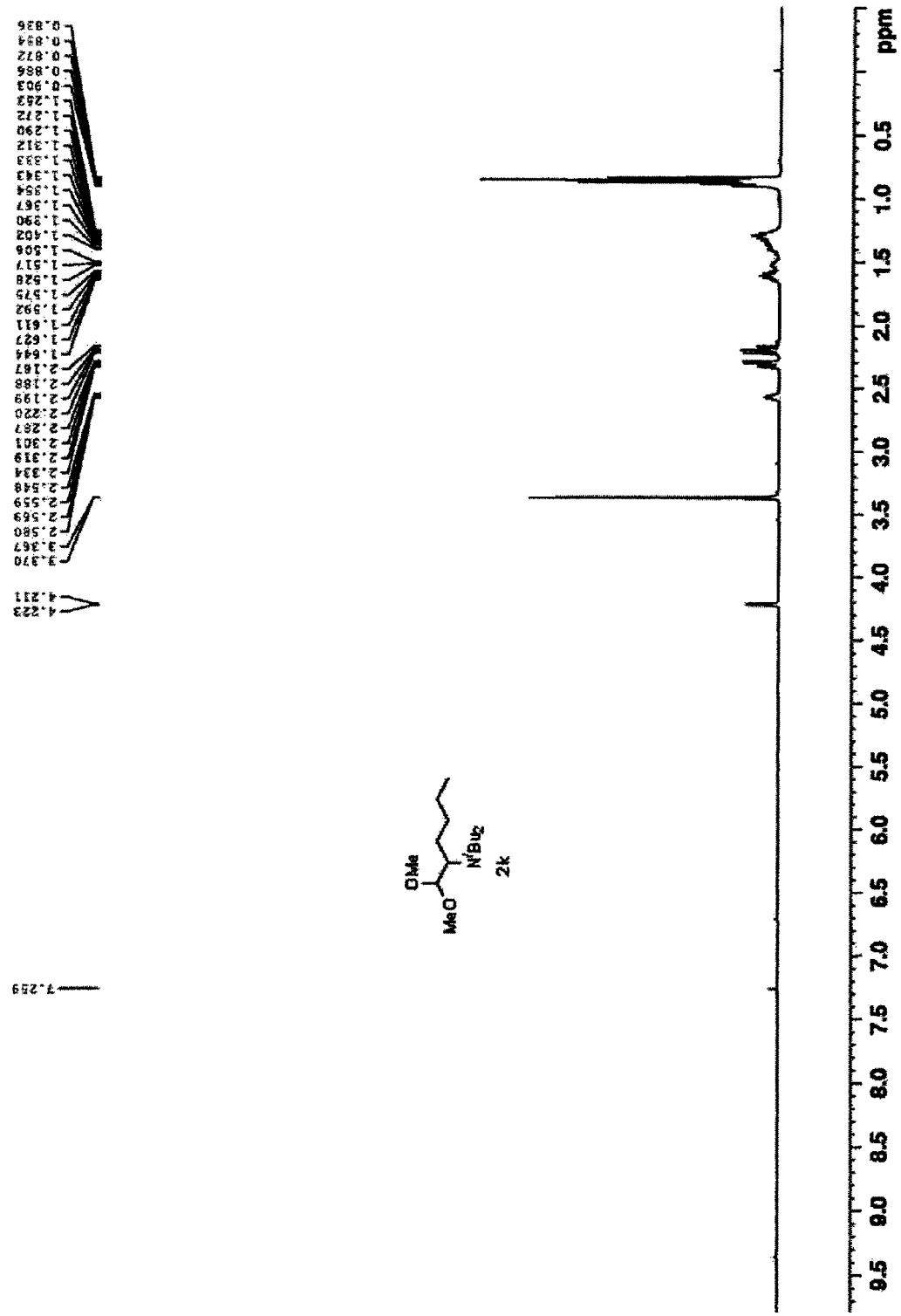
Figure 21B:
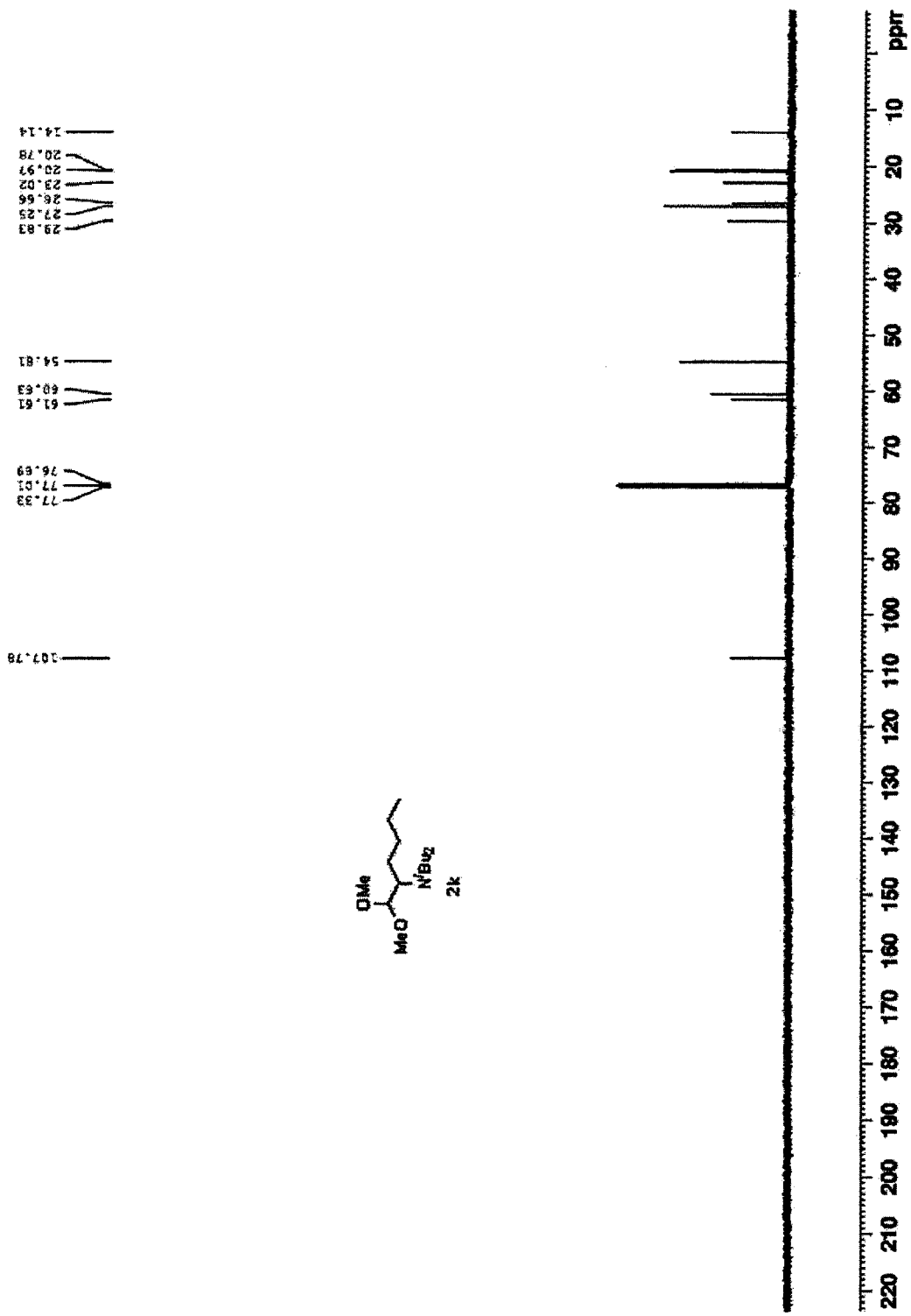

FIGS. 21(A) and (B) show, respectively, the $^1$H NMR and $^{13}$C NMR spectra of N,N-diisobutyl-1,1-dimethoxyhexan-2-amine (2k) of Example 1.

Figure 22A:
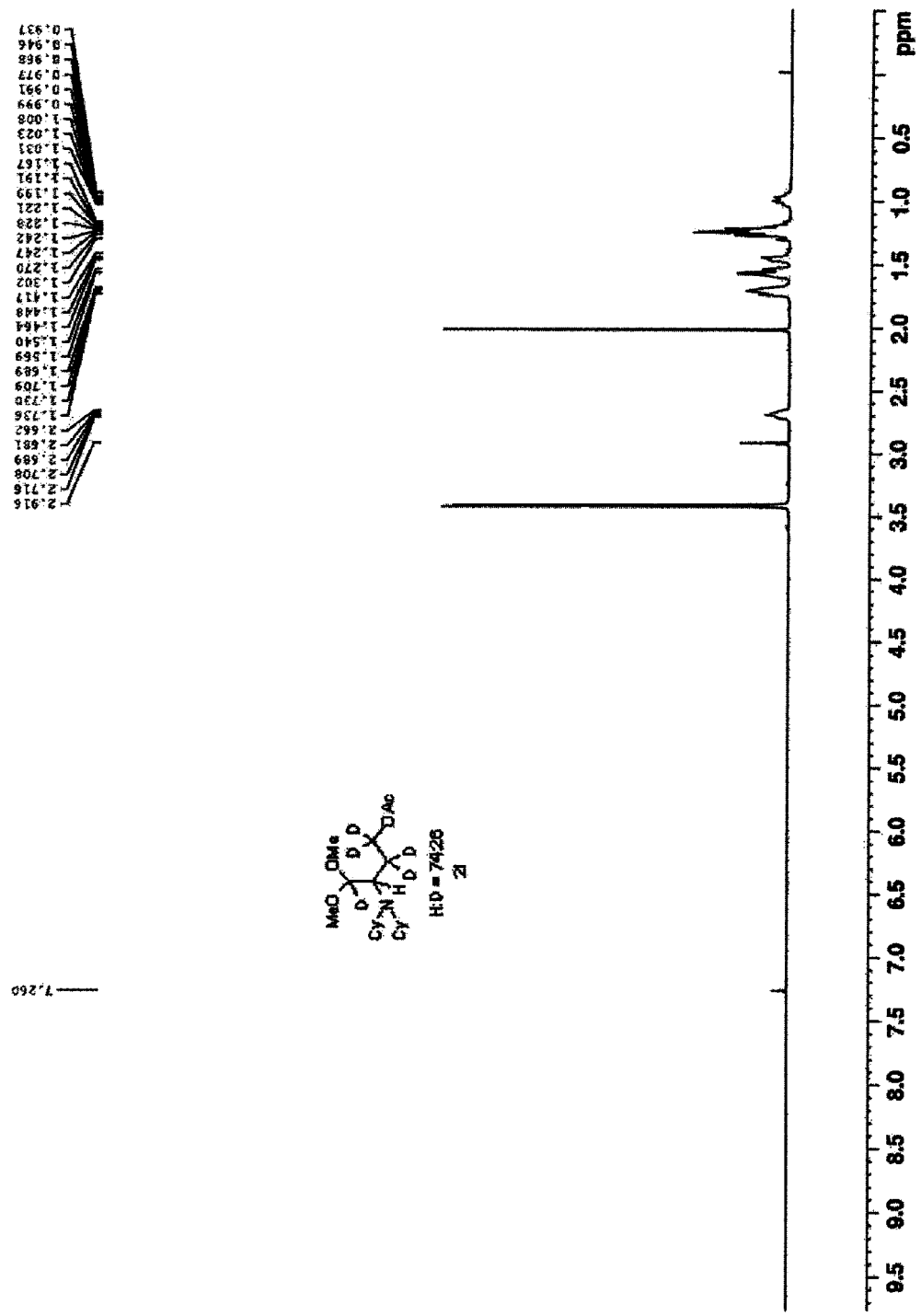
Figure 22B:
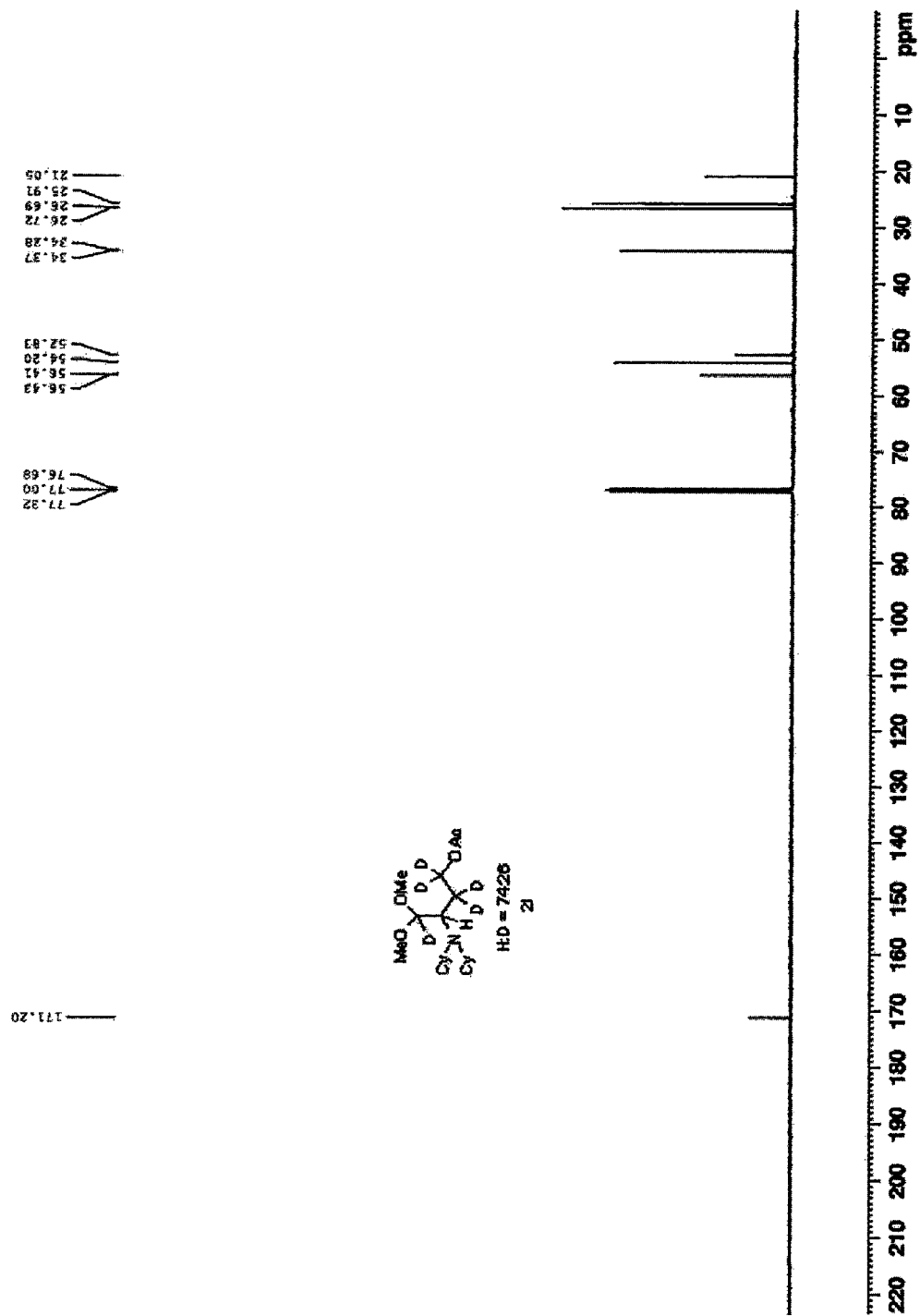

FIGS. 22(A) and (B) show, respectively, the $^1$H NMR and $^{13}$C NMR spectra of 3-(dicyclohexylamino)-4,4-dimethoxybutyl-D5 acetate (2l) of Example 1.

Figure 23A:
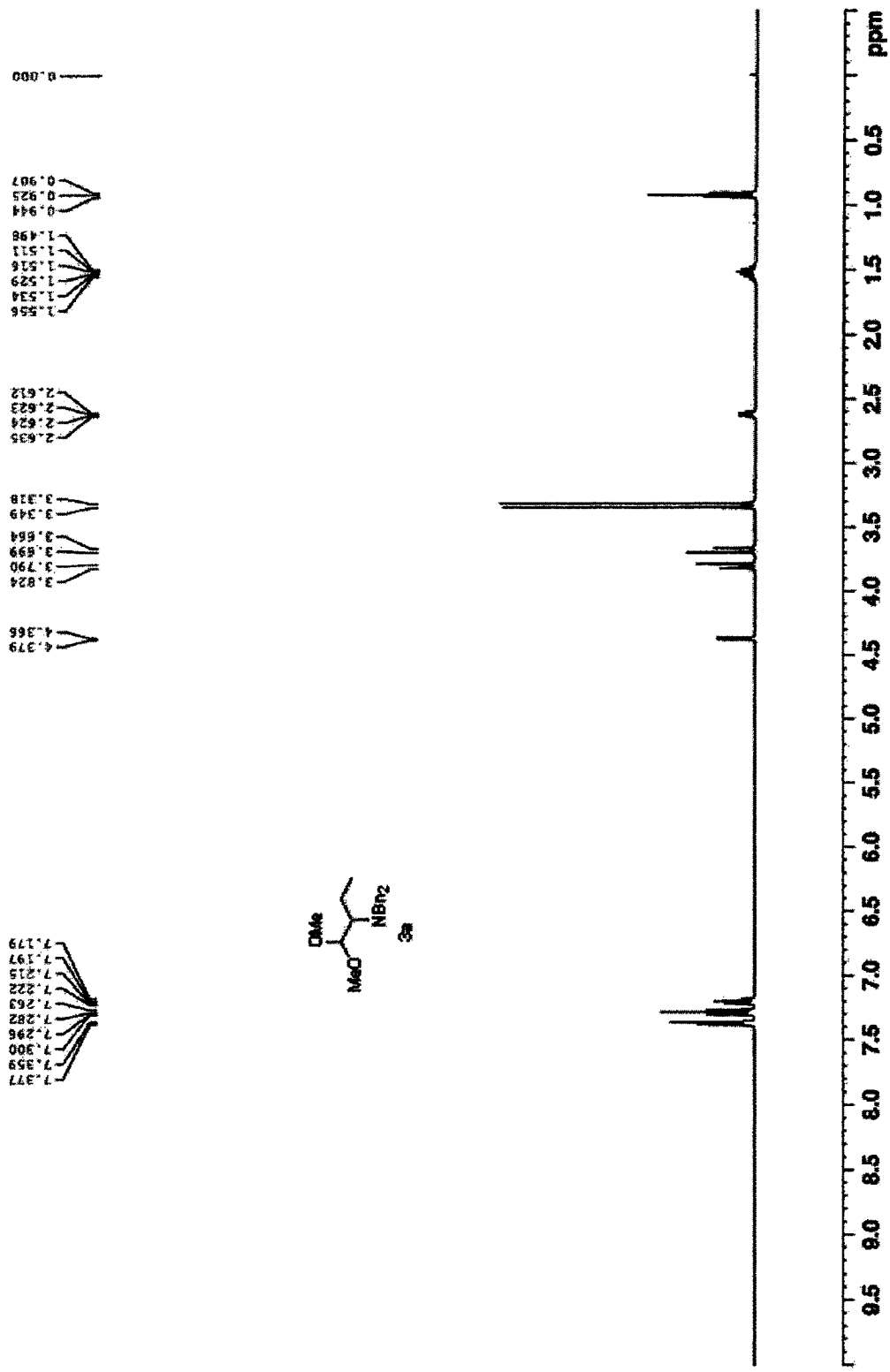
Figure 23B:
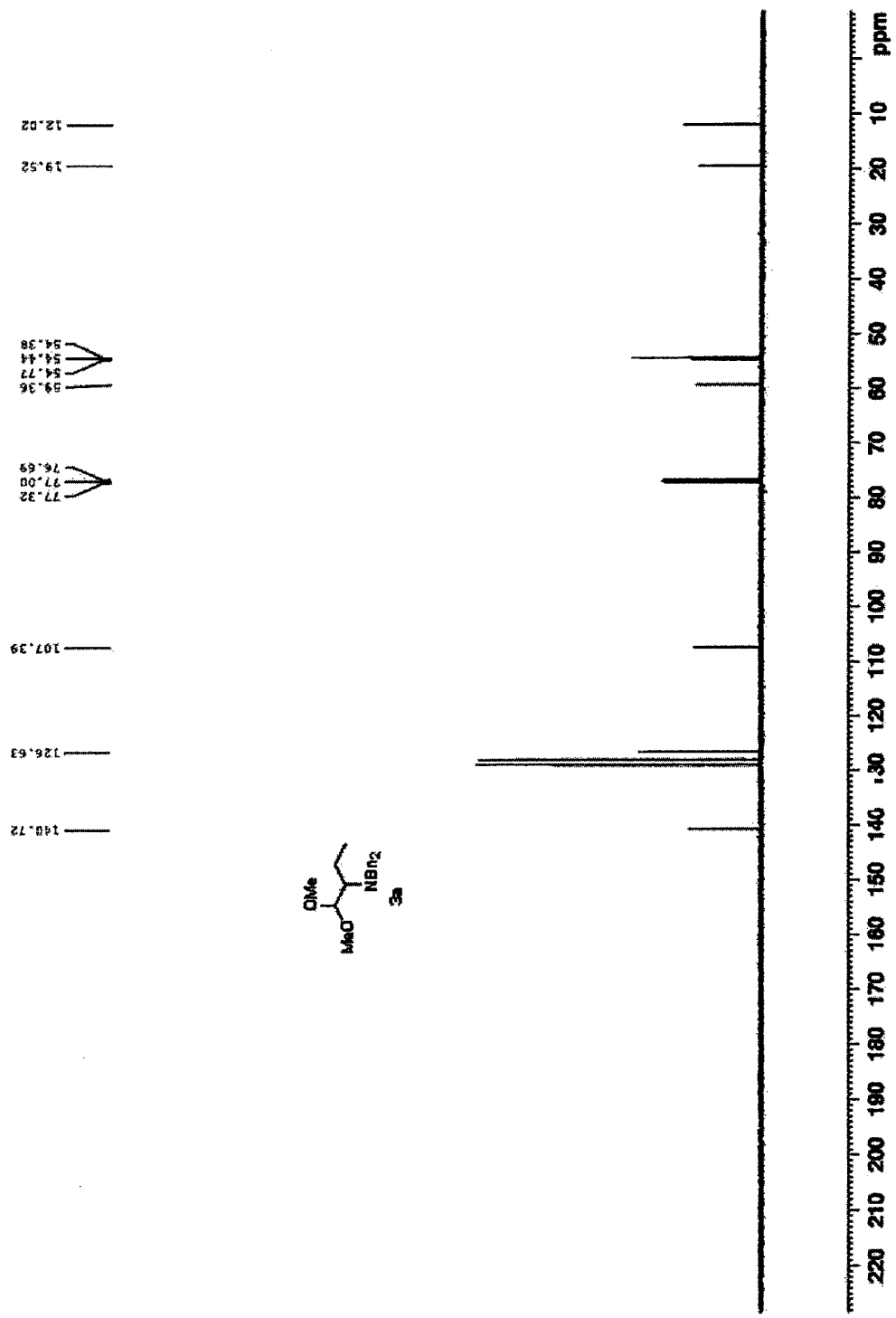

FIGS. 23(A) and (B) show, respectively, the $^1$H NMR and $^{13}$C NMR spectra of N,N-dibenzyl-1,1-dimethoxybutan-2-amine (3a) of Example 2.

Figure 24A:
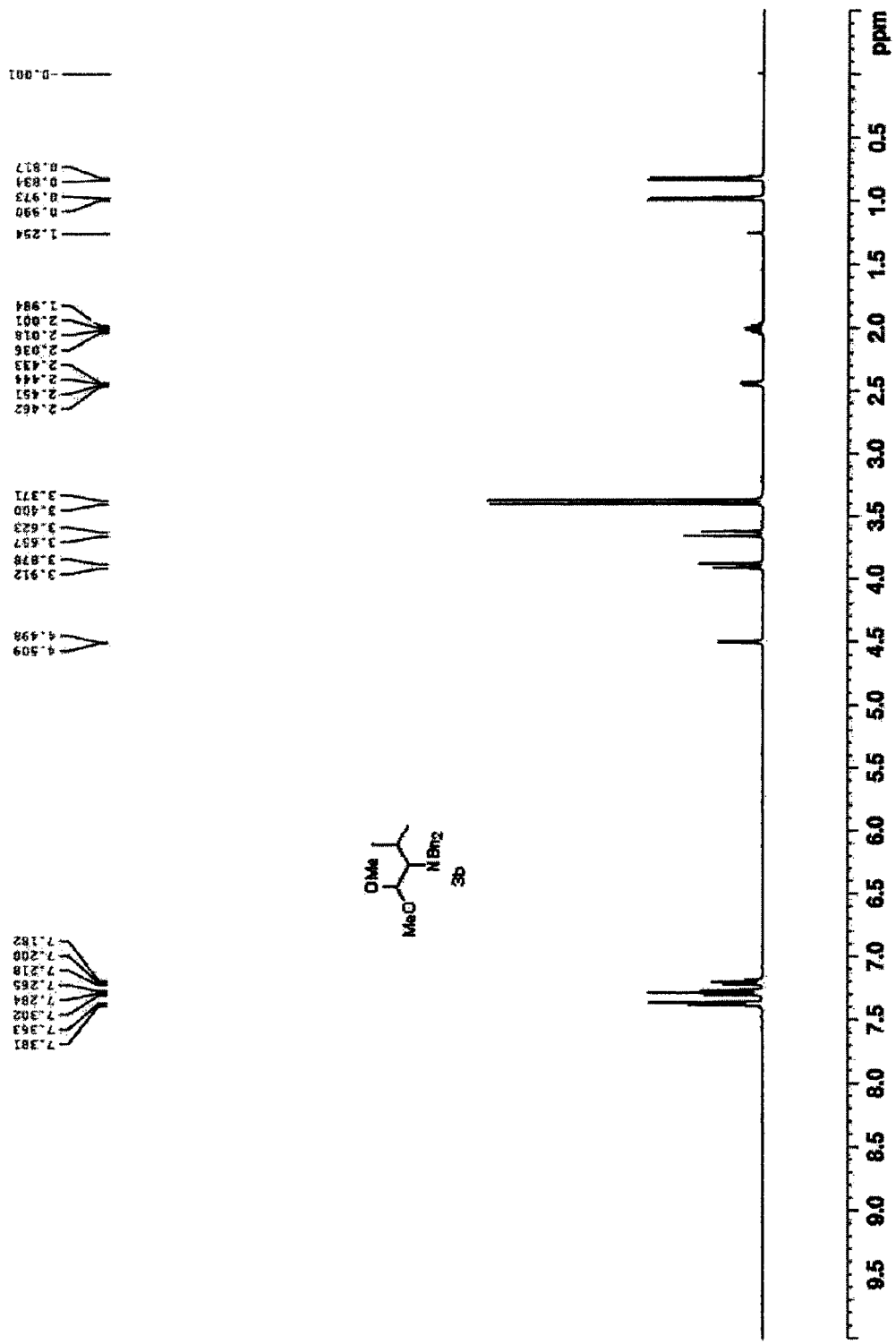
Figure 24B:
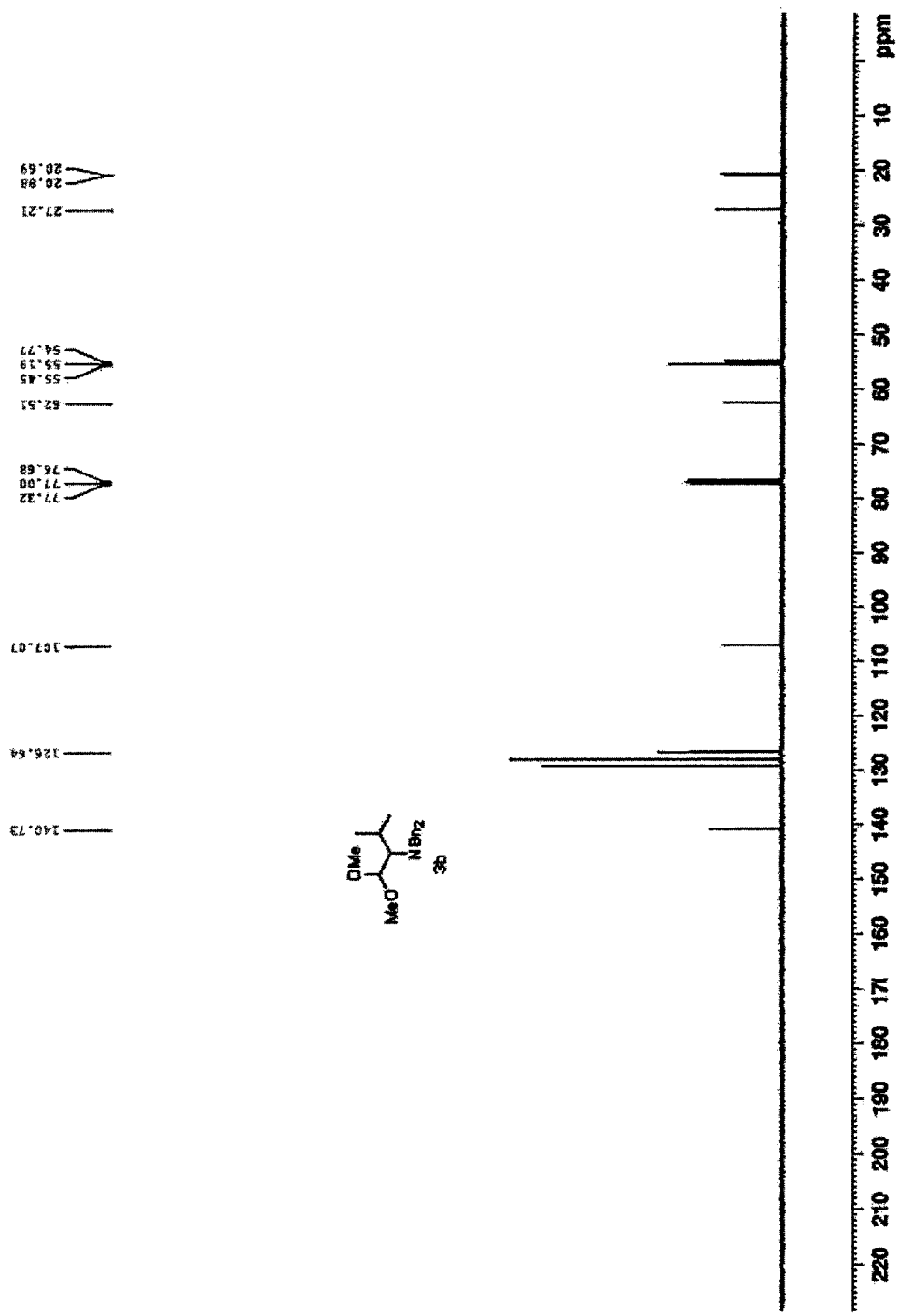

FIGS. 24(A) and (B) show, respectively, the $^1$H NMR and $^{13}$C NMR spectra of N,N-dibenzyl-1,1-dimethoxy-3-methylbutan-2-amine (3b) of Example 2.

Figure 25A:
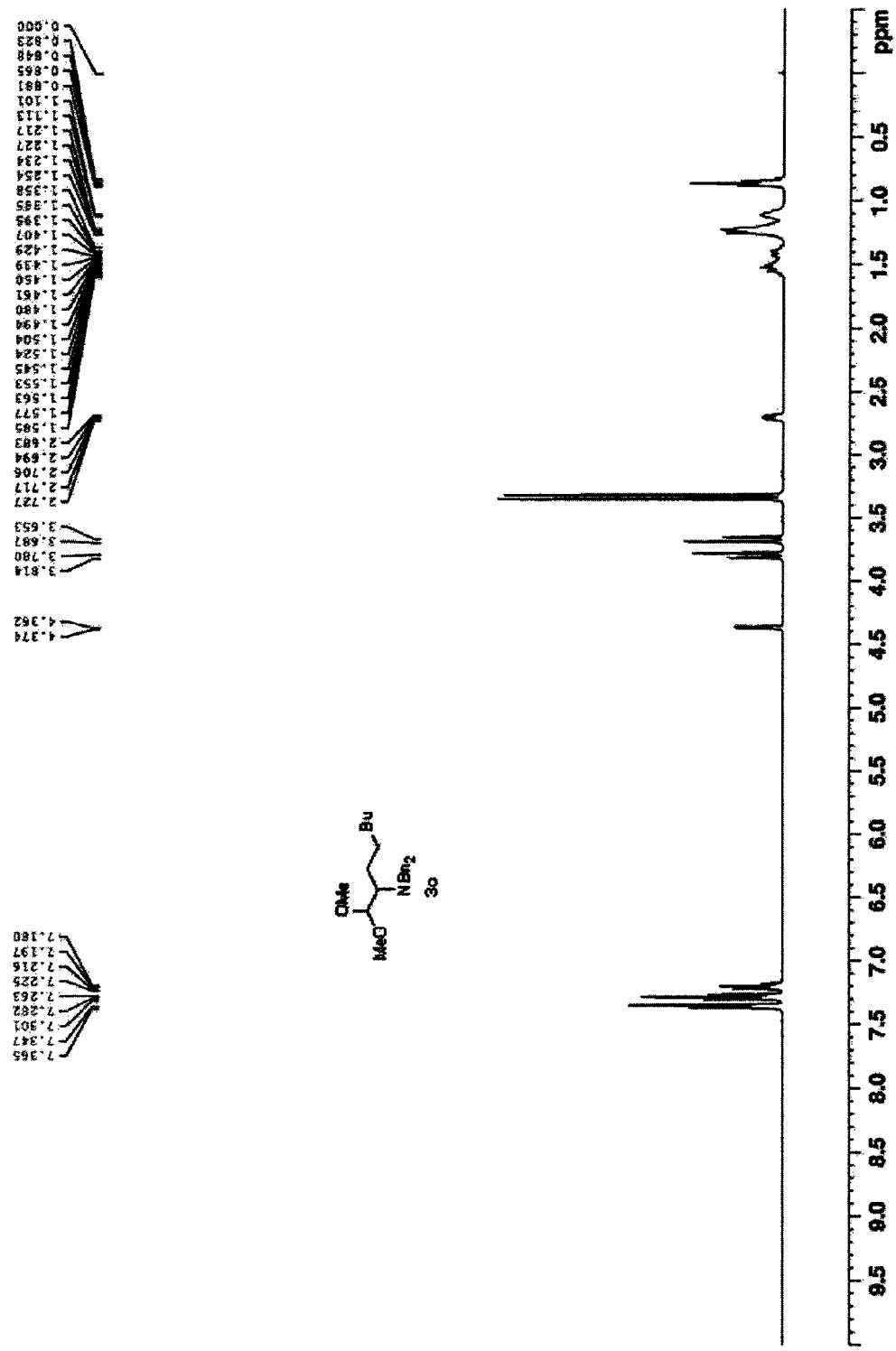
Figure 25B:
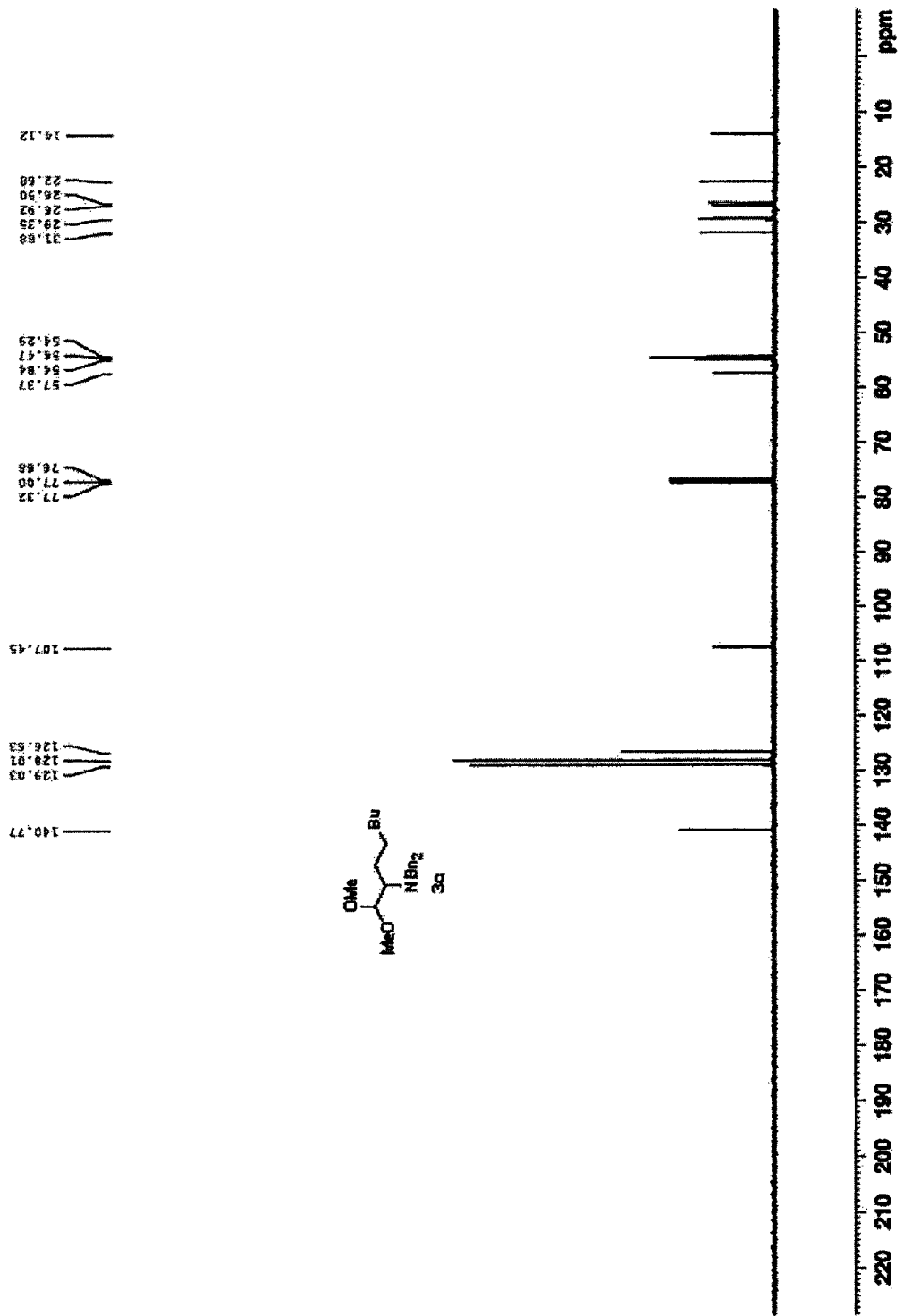

FIGS. 25(A) and (B) show, respectively, the $^1$H NMR and $^{13}$C NMR spectra of N,N-dibenzyl-1,1-dimethoxyoctan-2-amine (3c) of Example 2.

Figure 26A:
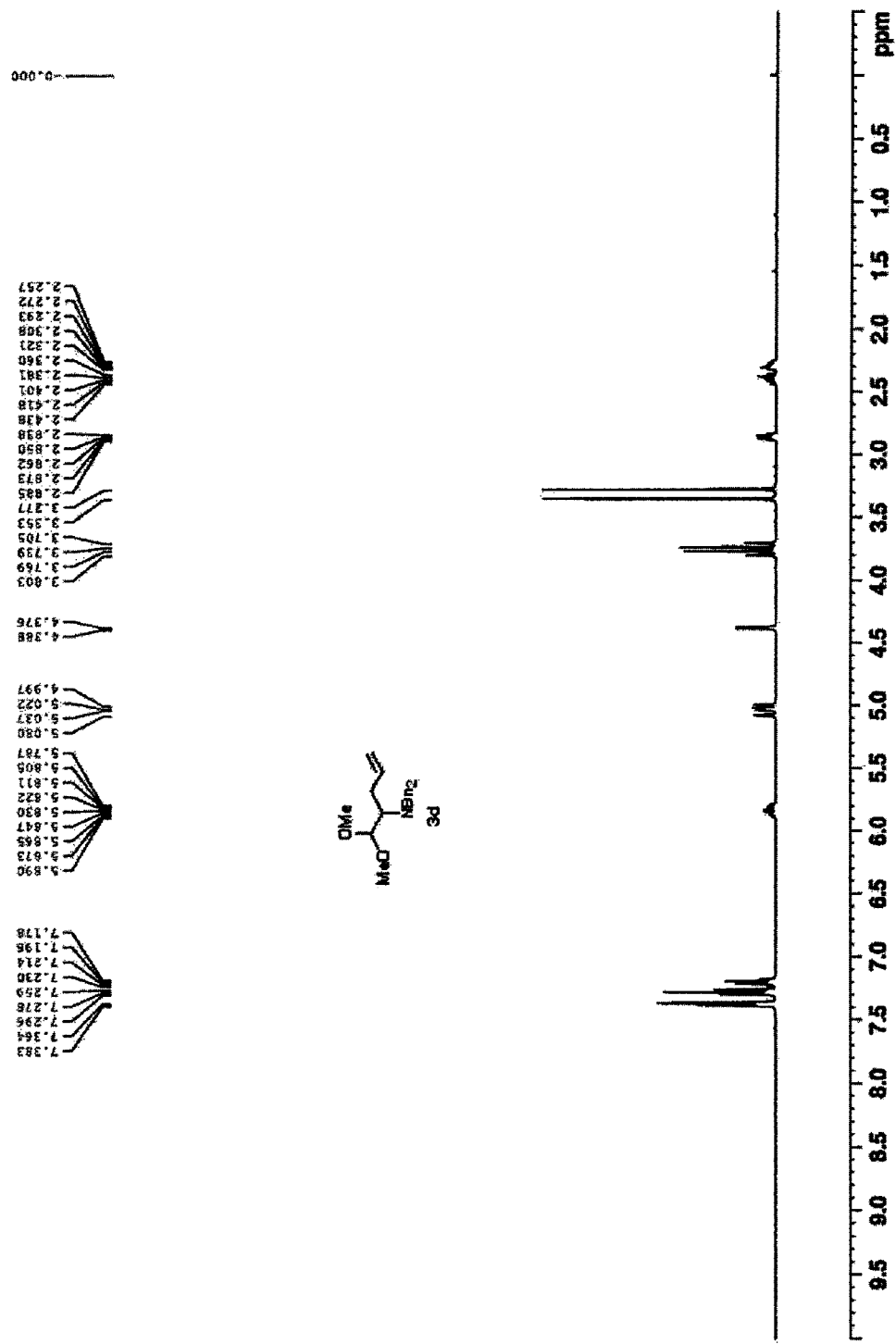
Figure 26B:
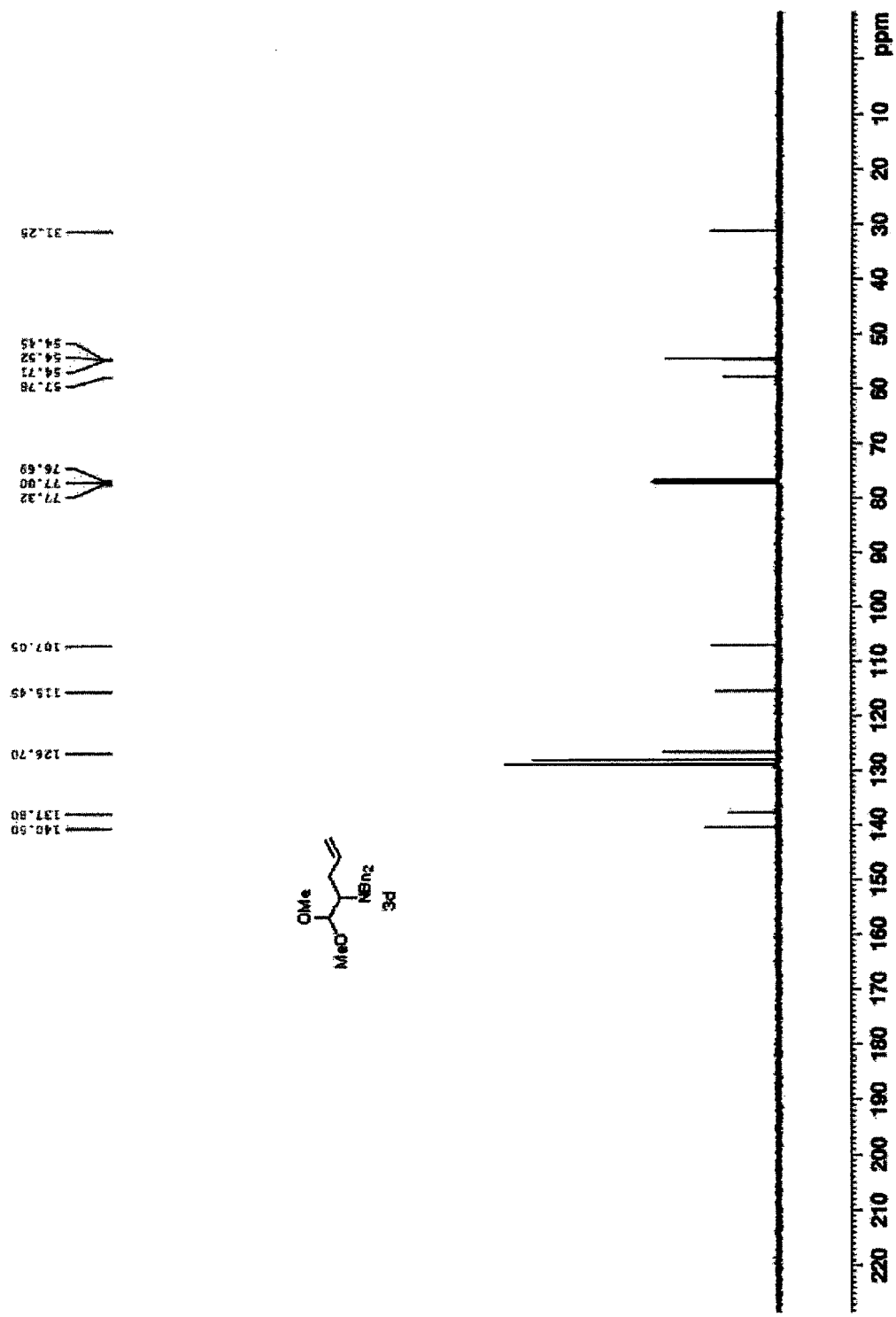

FIGS. 26(A) and (B) show, respectively, the $^1$H NMR and $^{13}$C NMR spectra of N,N-dibenzyl-1,1-dimethoxypent-4-en-2-amine (3d) of Example 2.

Figure 27A:
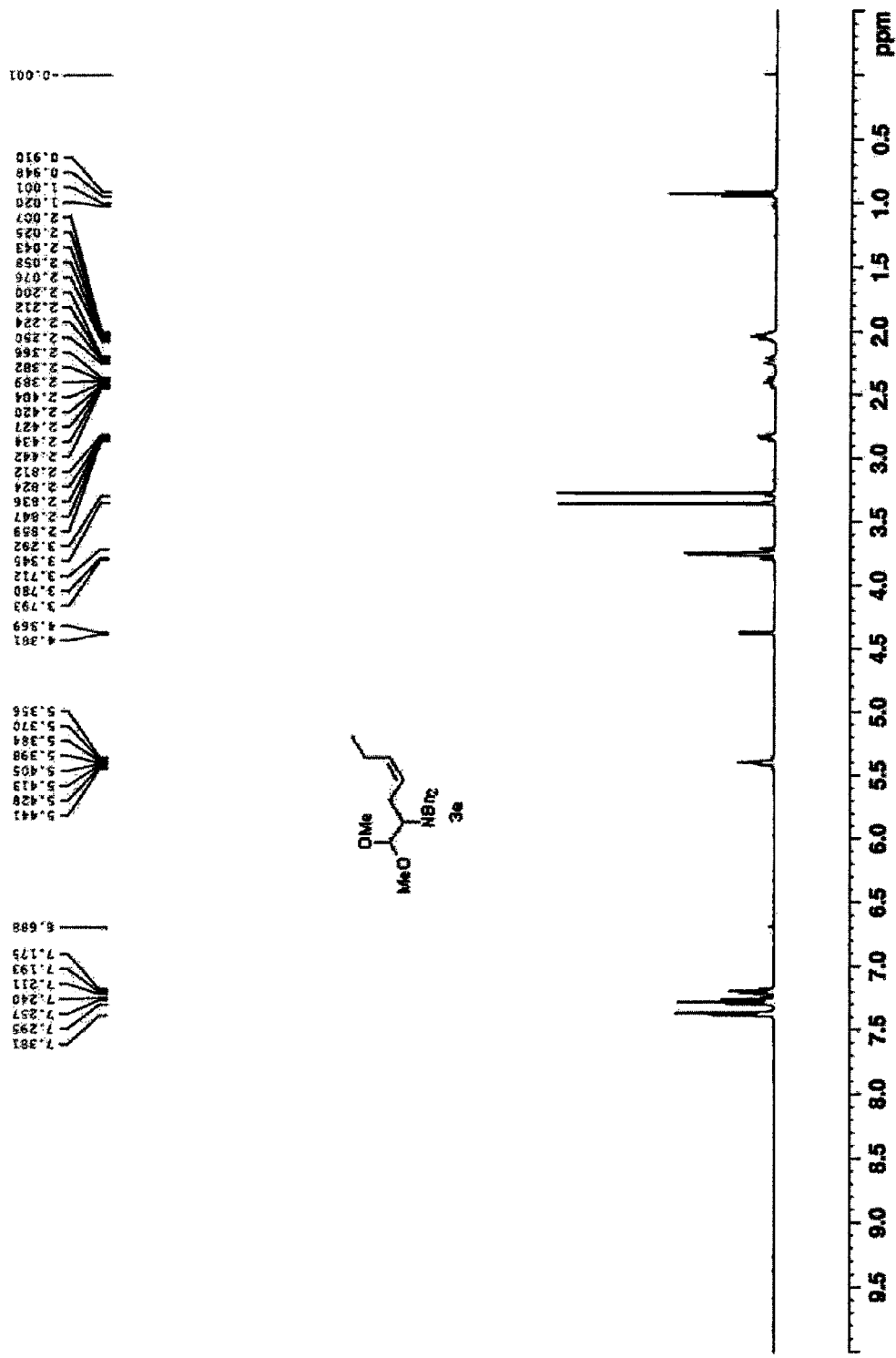
Figure 27B:
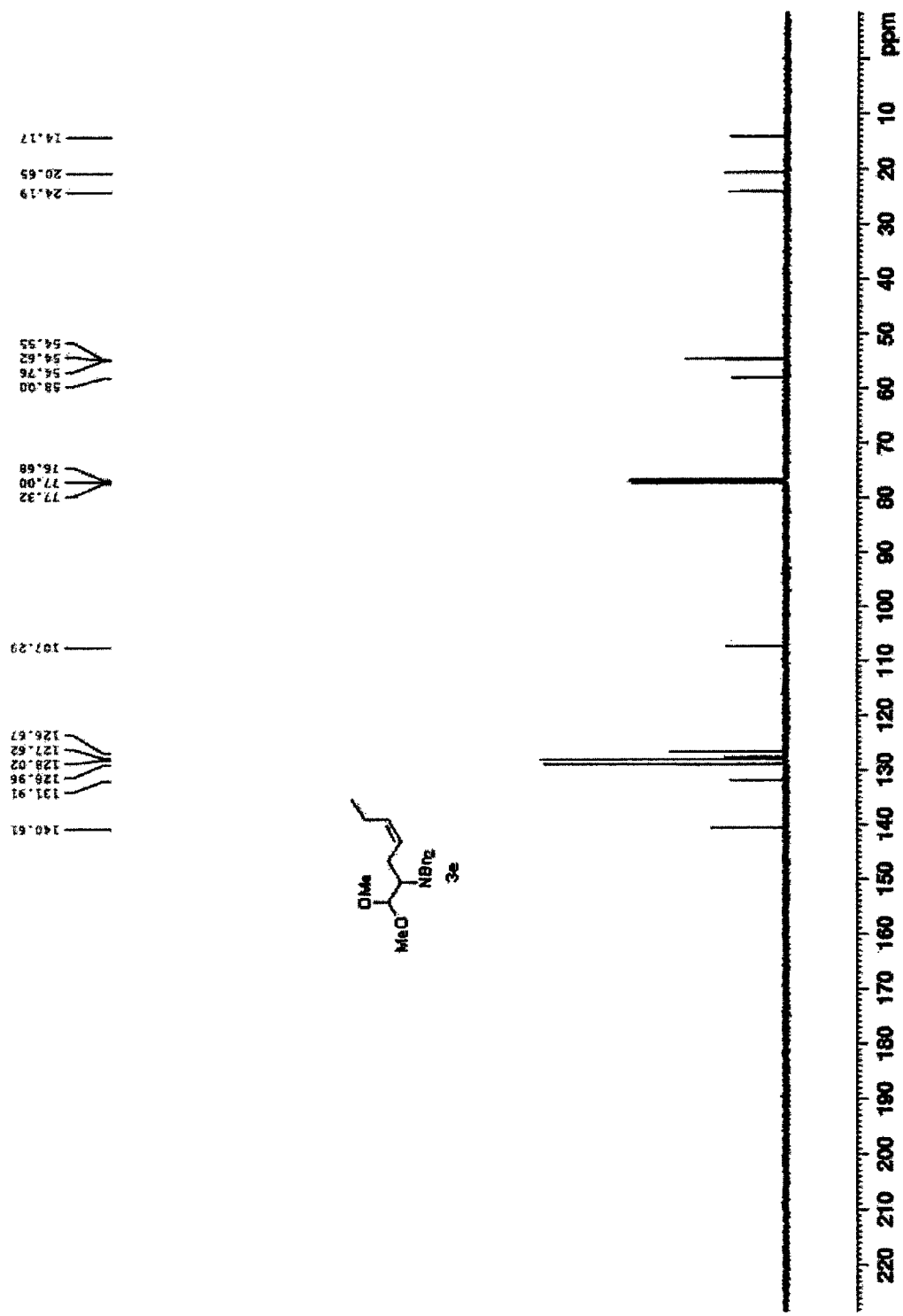

FIGS. 27(A) and (B) show, respectively, the $^1$H NMR and $^{13}$C NMR spectra of (Z)—N,N-dibenzyl-1,1-dimethoxyhept-4-en-2-amine (3e) of Example 2.

Figure 28A:
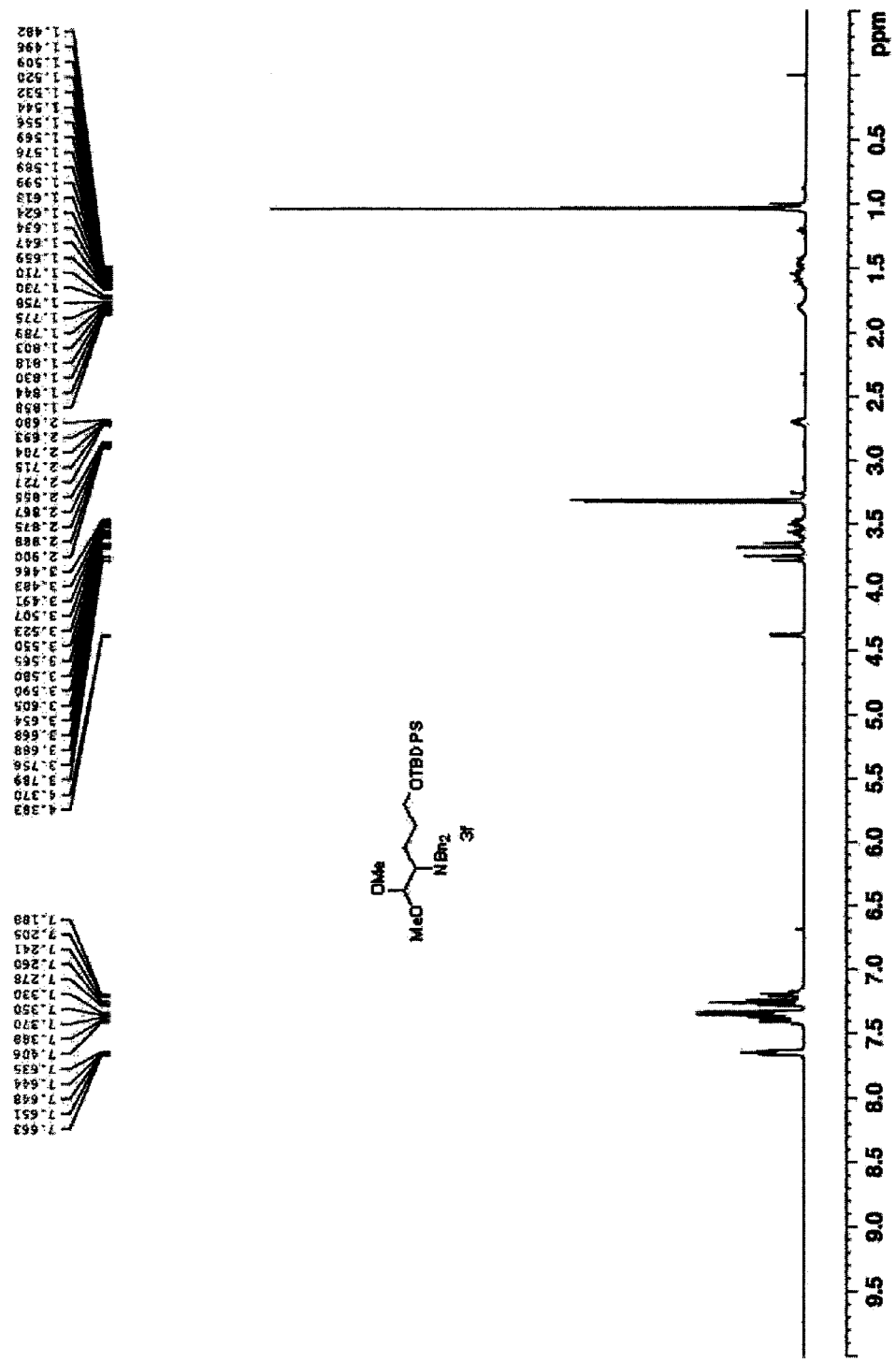
Figure 28B:
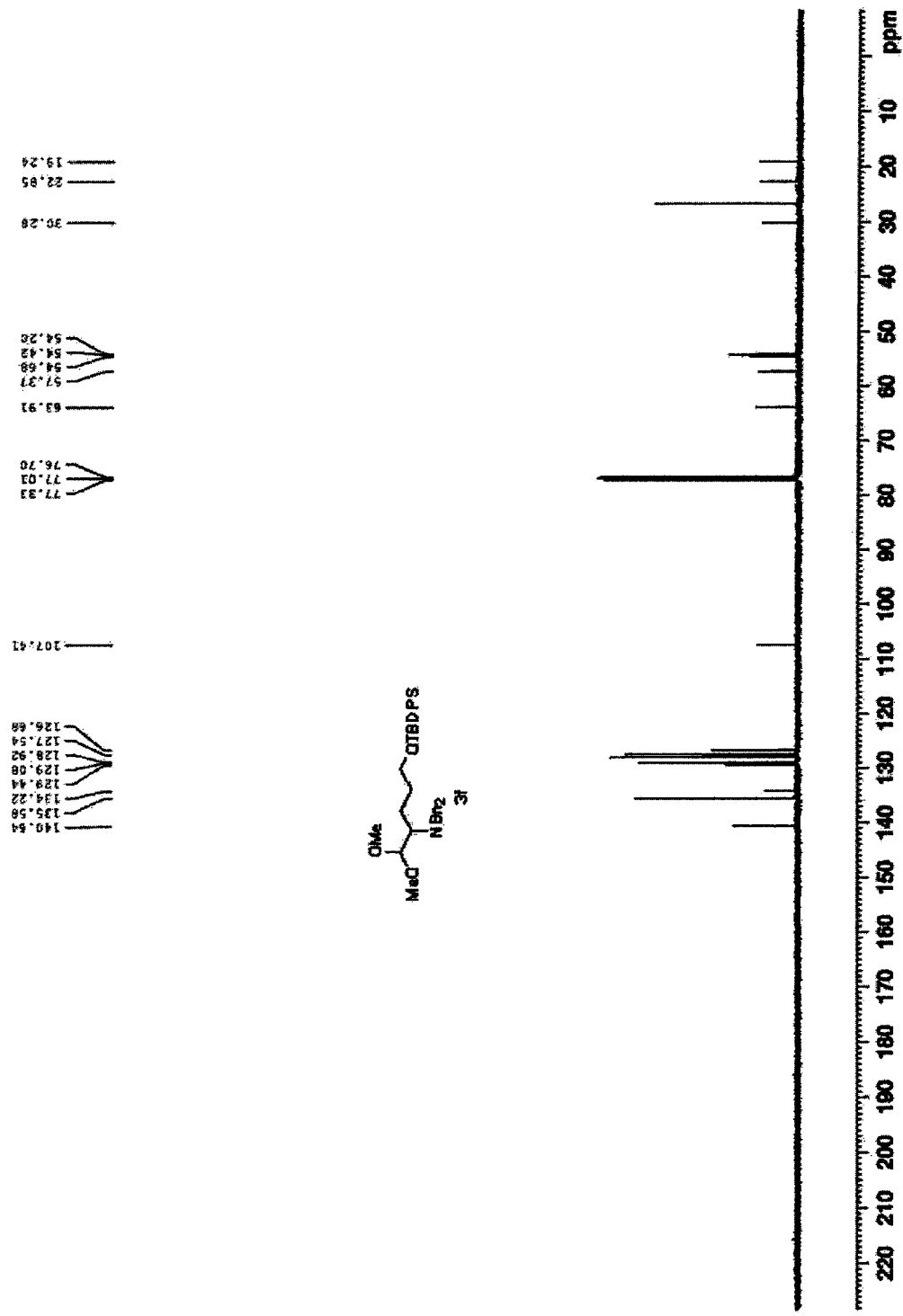

FIGS. 28(A) and (B) show, respectively, the $^1$H NMR and $^{13}$C NMR spectra of N,N-dibenzyl-5-(tert-butyldiphenylsilyloxy)-1,1-dimethoxypentan-2-amine (3f) of Example 2.

Figure 29A:
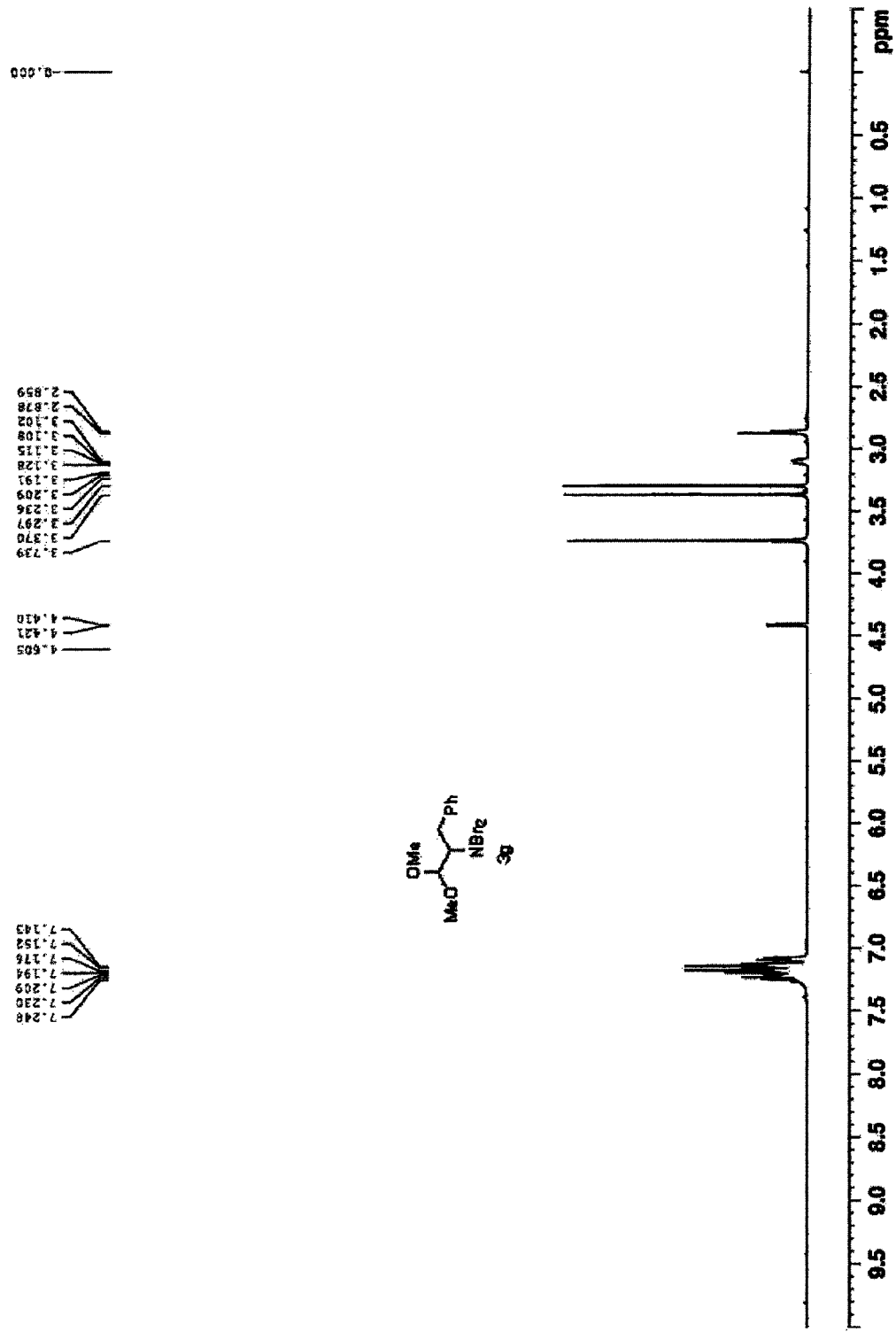
Figure 29B:
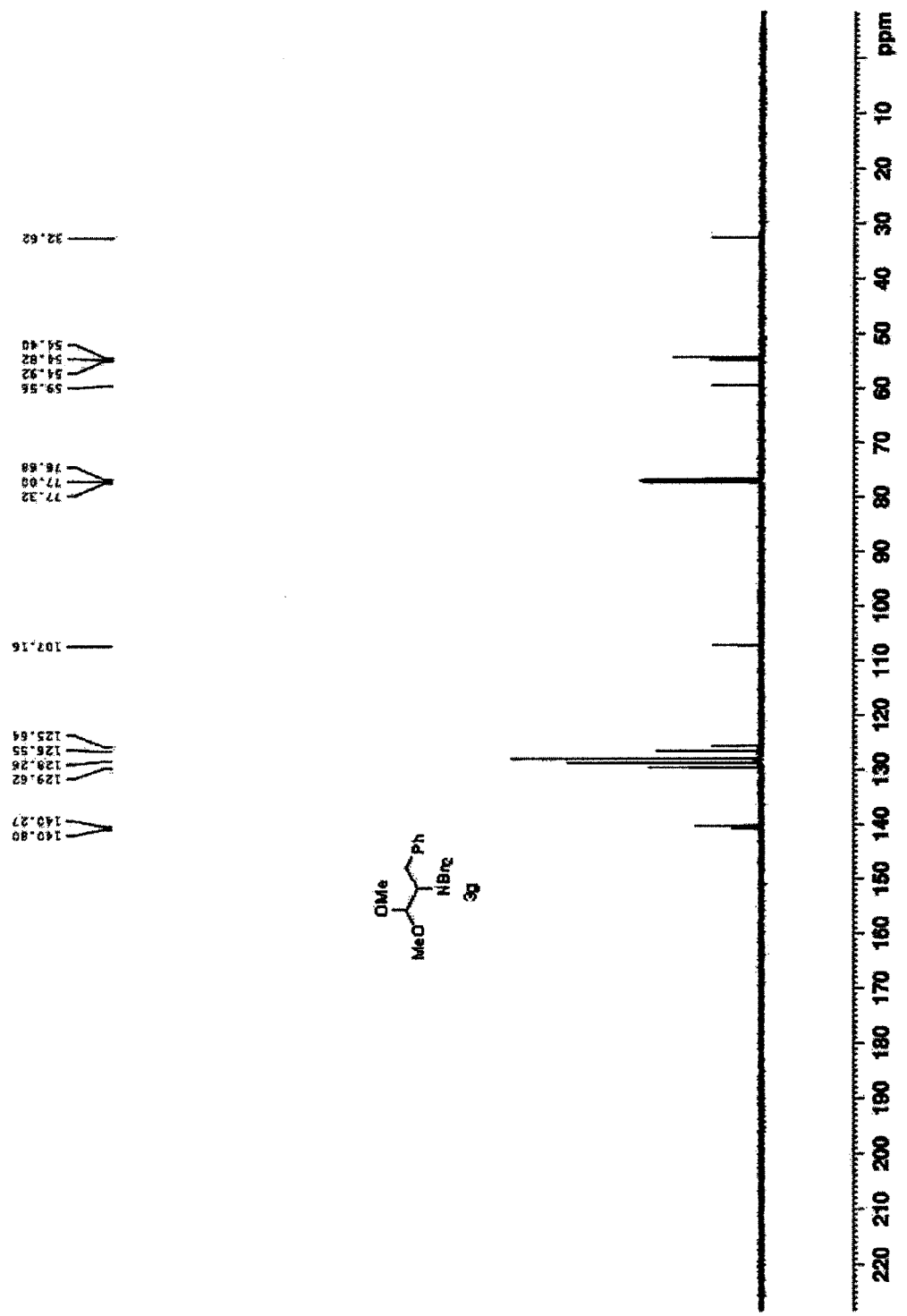

FIGS. 29(A) and (B) show, respectively, the $^1$H NMR and $^{13}$C NMR spectra of N,N-dibenzyl-1,1-dimethoxy-3-phenylpropan-2-amine (3g) of Example 2.

Figure 30A:
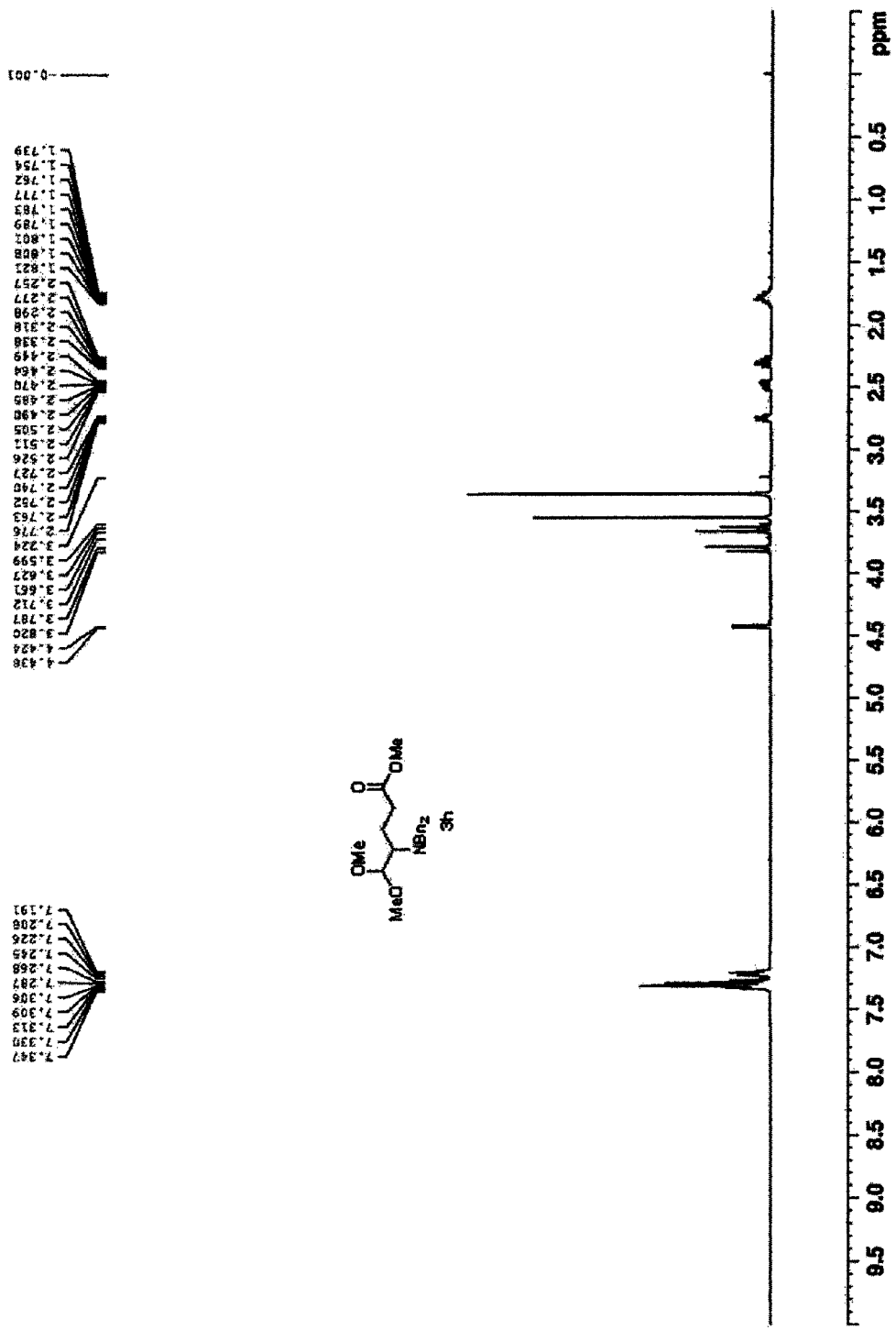
Figure 30B:
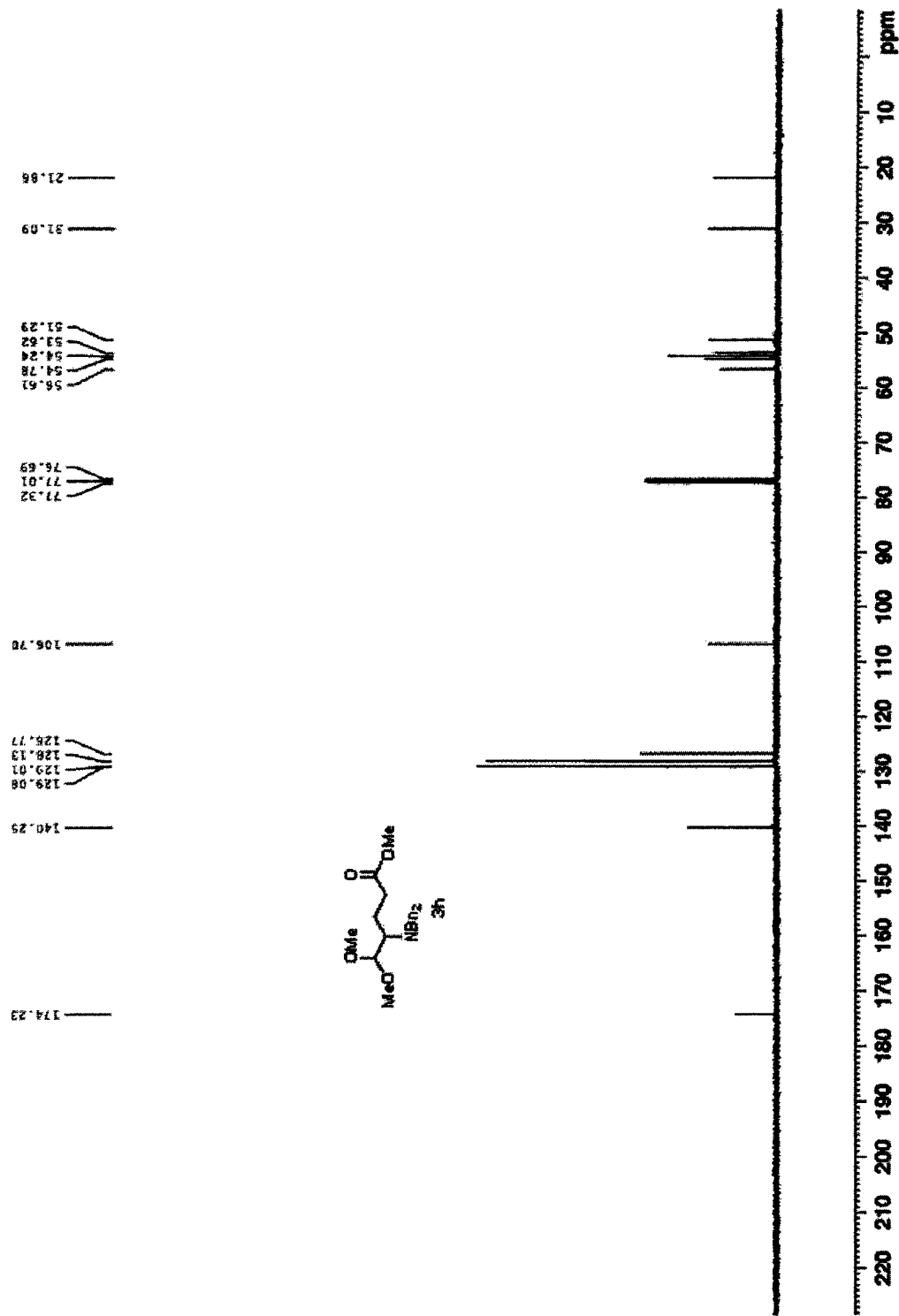

FIGS. 30(A) and (B) show, respectively, the $^1$H NMR and $^{13}$C NMR spectra of methyl 4-(dibenzylamino)-5,5-dimethoxypentanoate (3h) of Example 2.

Figure 31A:
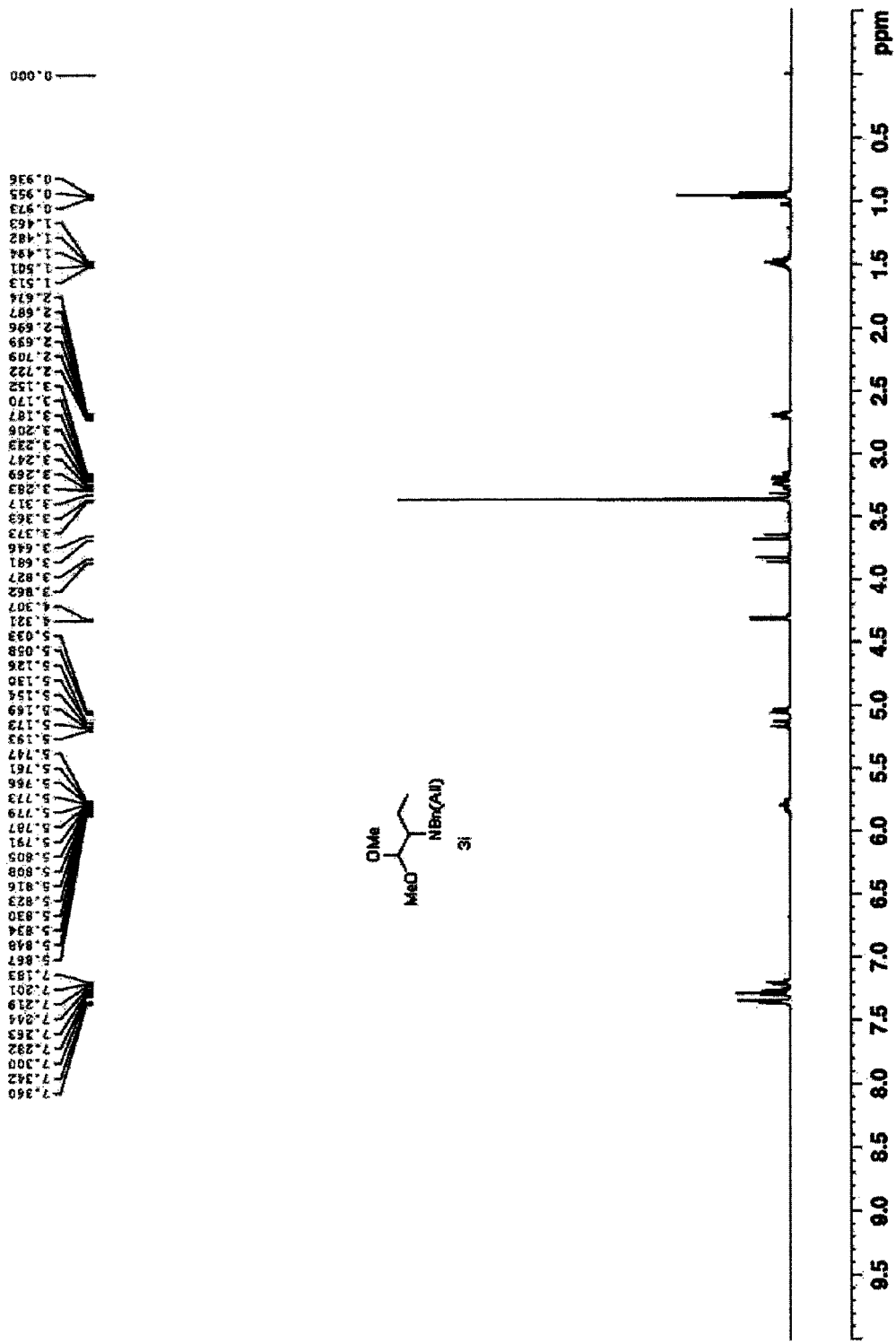
Figure 31B:
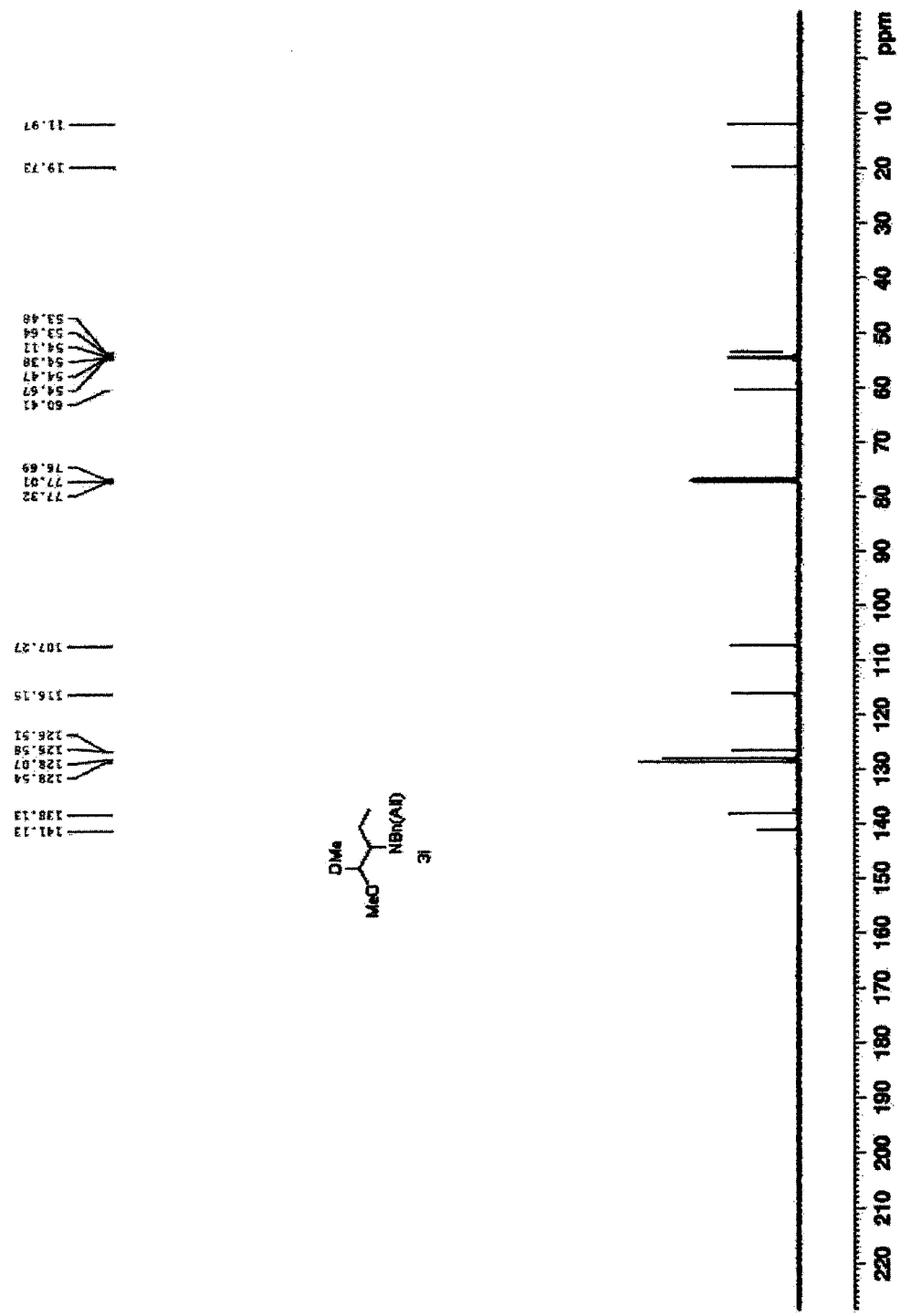

FIGS. 31(A) and (B) show, respectively, the $^1$H NMR and $^{13}$C NMR spectra of N-allyl-N-benzyl-1,1-dimethoxybutan-2-amine (3i) of Example 2.

Figure 32A:
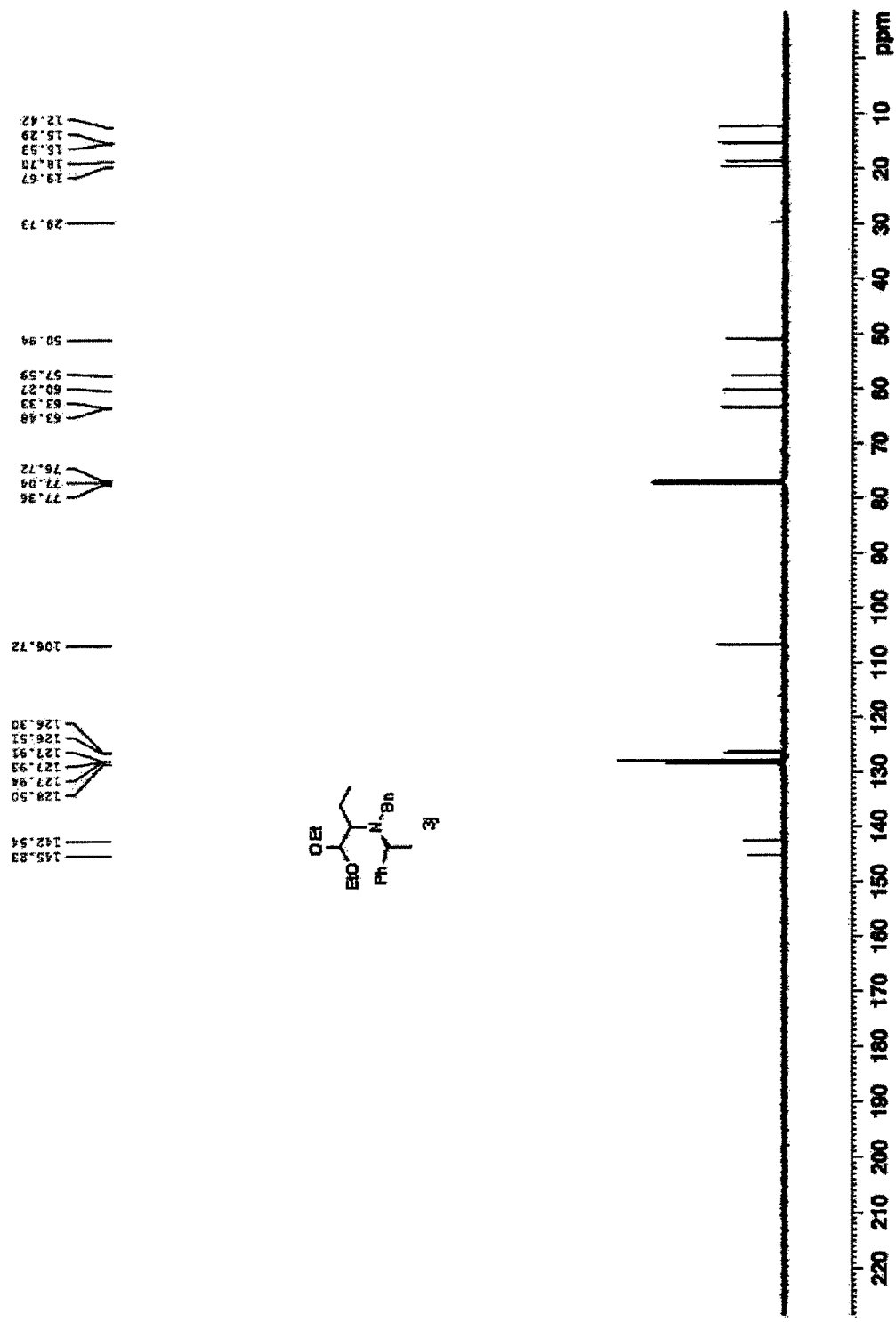
Figure 32B:
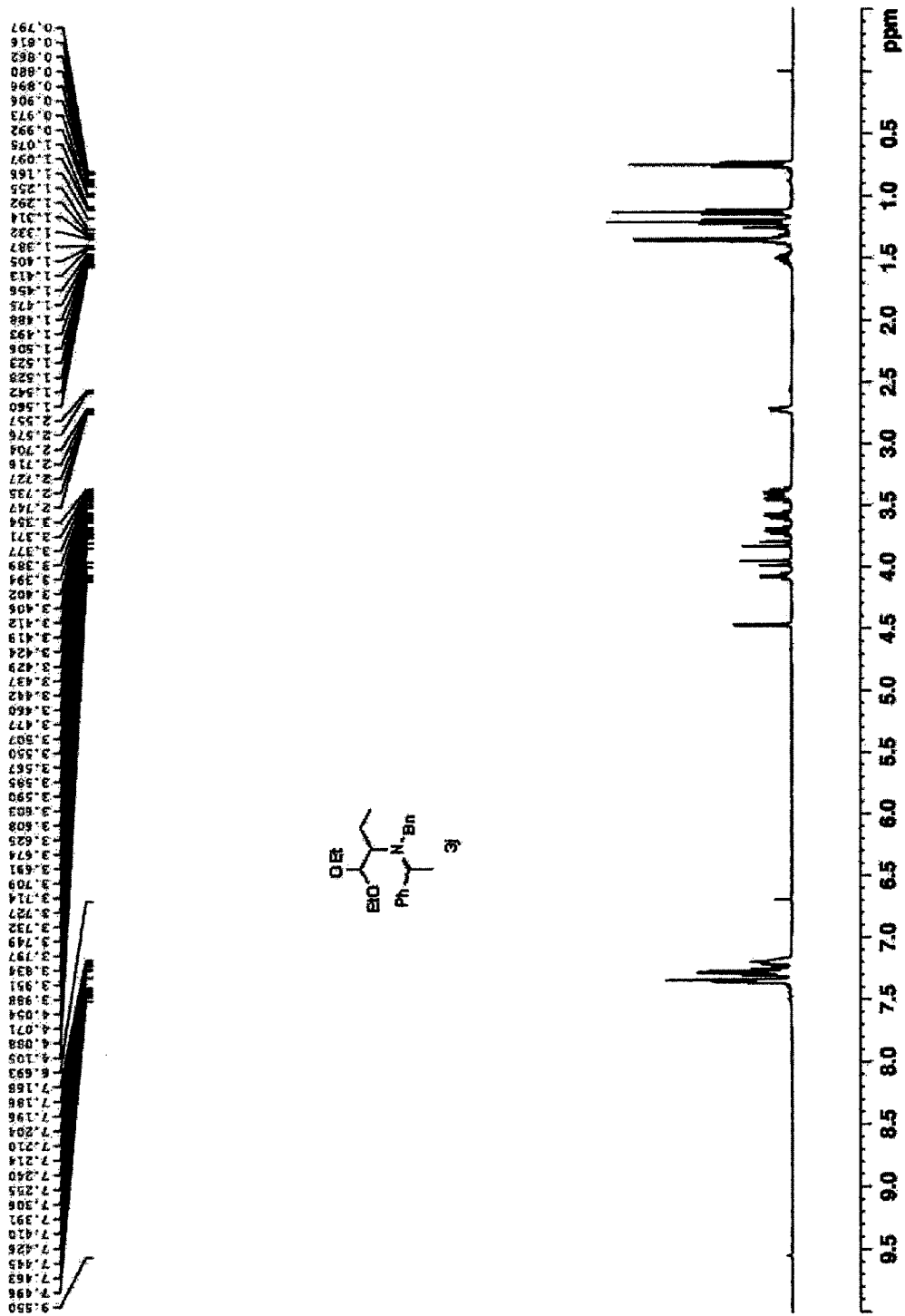

FIGS. 32(A) and (B) show, respectively, the $^1$H NMR and $^{13}$C NMR spectra of N-benzyl-1,1-diethoxy-N—((R)-1-phenylethyl)butan-2-amine (3j) of Example 2.

Figure 33A:
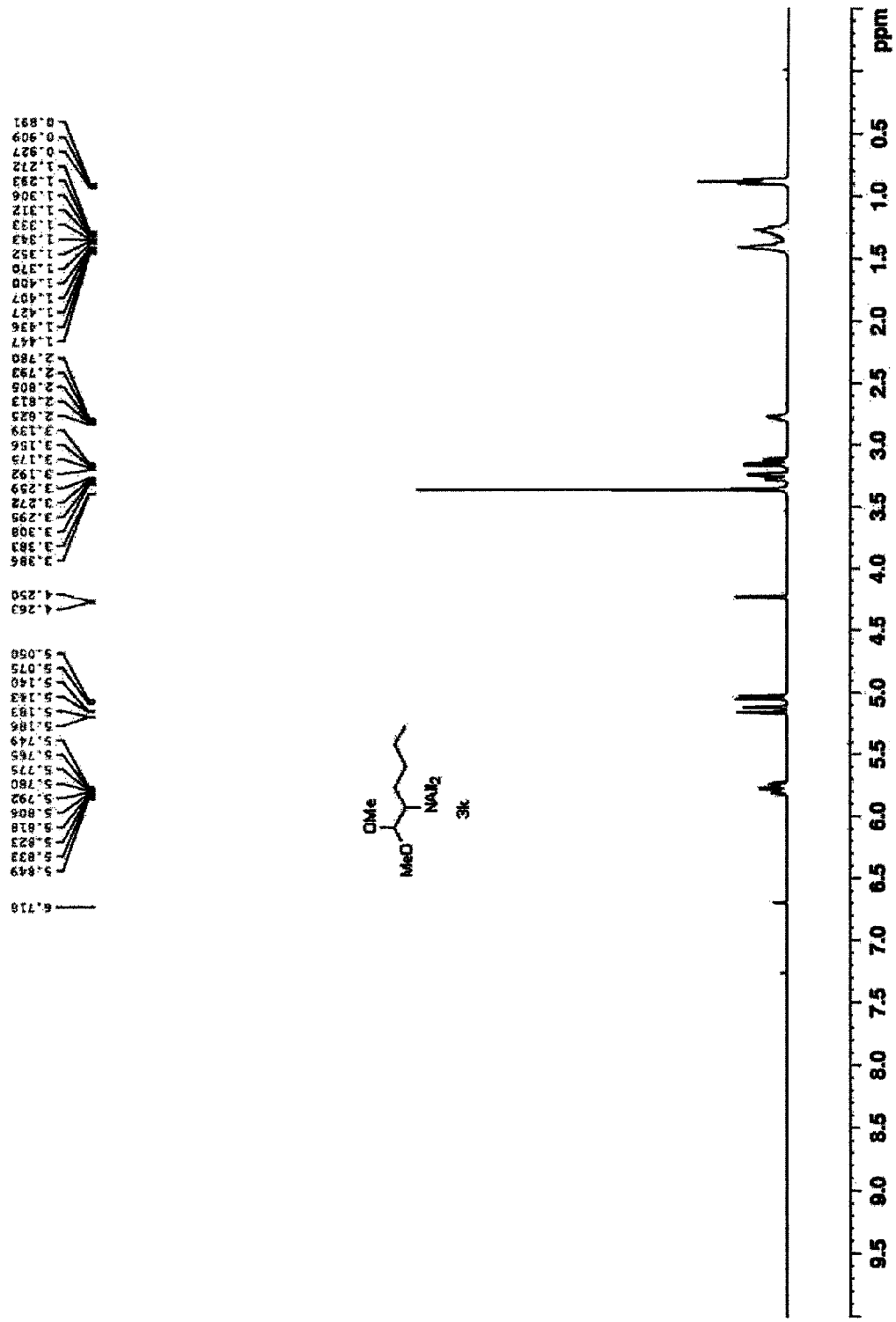
Figure 33B:
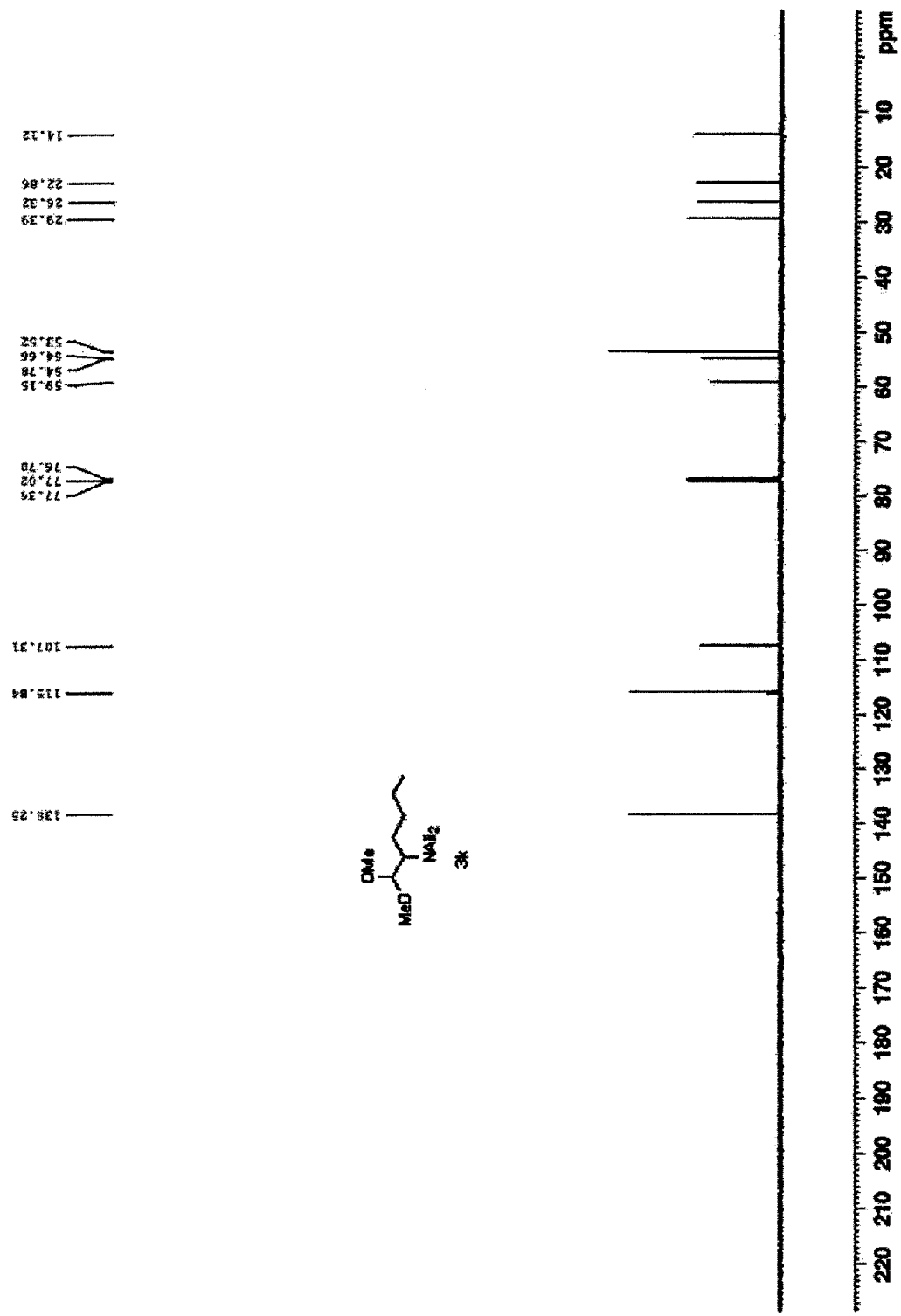

FIGS. 33(A) and (B) show, respectively, the $^1$H NMR and $^{13}$C NMR spectra of N,N-diallyl-1,1-dimethoxyhexan-2-amine (3k) of Example 2.

Figure 34A:
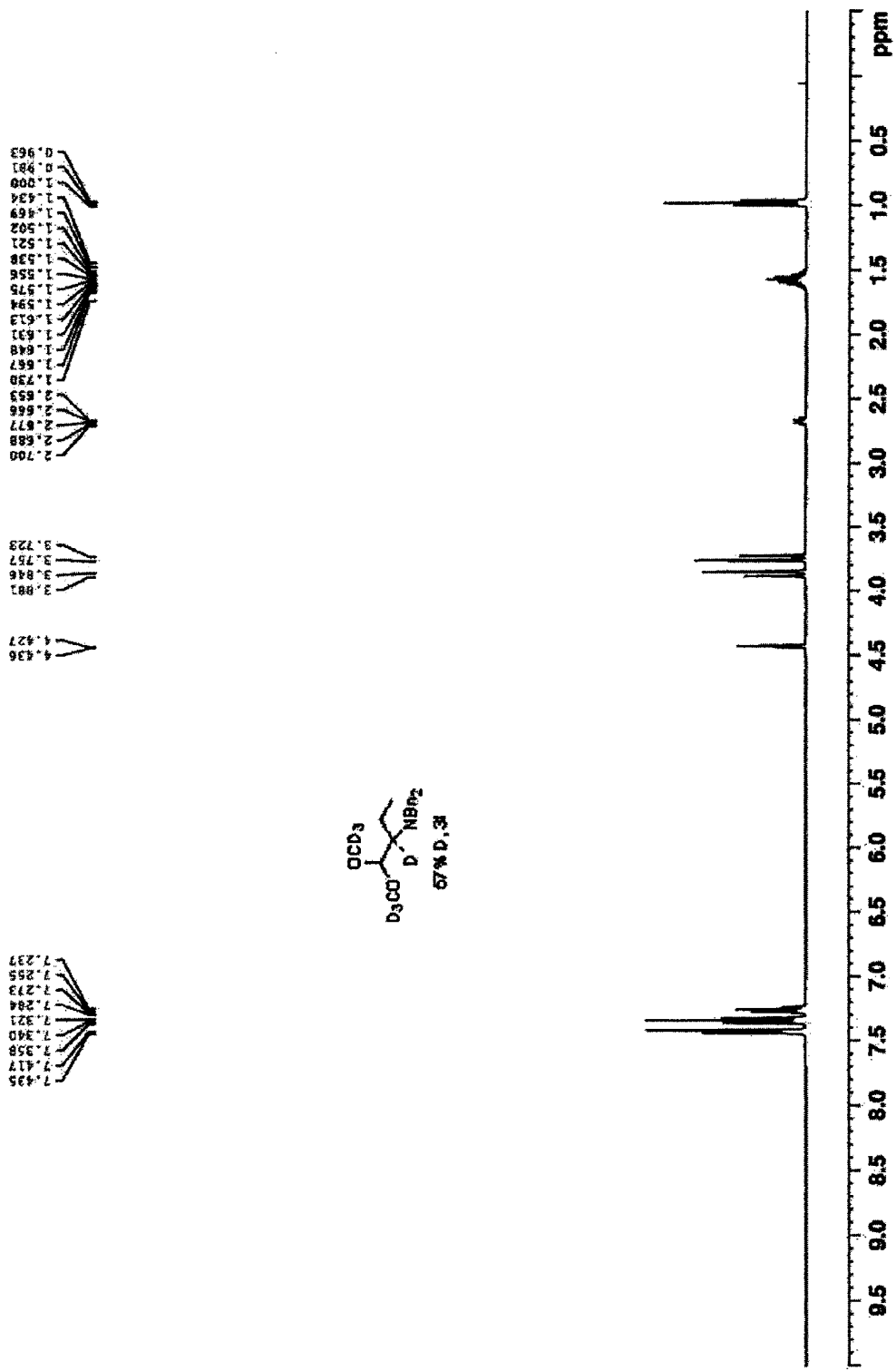
Figure 34B:
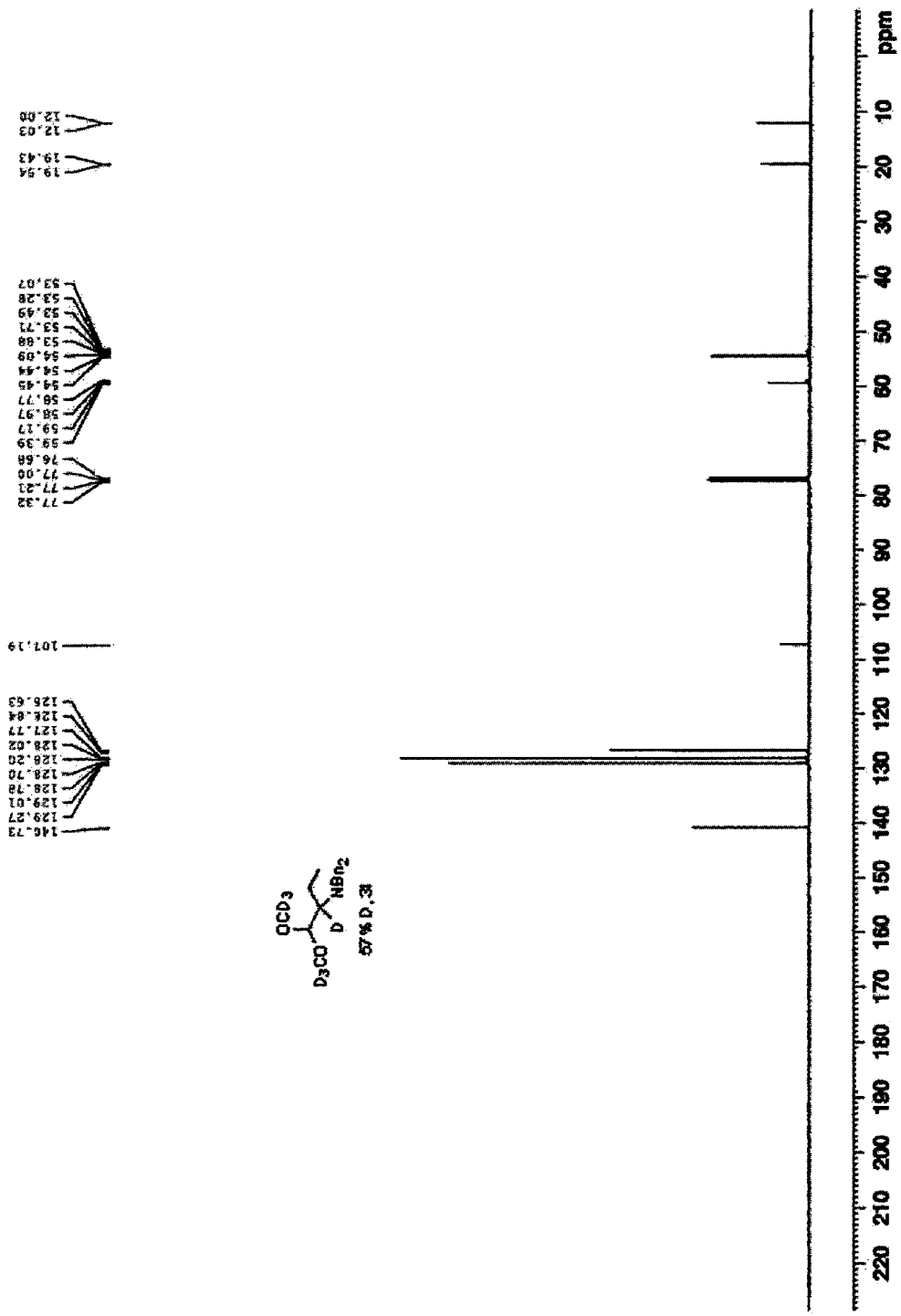

FIGS. 34(A) and (B) show, respectively, the $^1$H NMR and $^{13}$C NMR spectra of N,N-dibenzyl-1,1-dimethoxy-D6-butan-D1-2-amine (3l) of Example 2.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural changes may be made without departing from the scope of the invention. The various embodiments are not necessarily mutually exclusive, as some embodiments can be combined with one or more other embodiments to form new embodiments.

In various embodiments of the present invention, a method of synthesising an amino acetal is provided. The method may include oxidizing a tertiary amine in the presence of a copper catalyst, at least one oxidant and a solvent. The method may also include reacting a secondary amine and an aliphatic aldehyde in the presence of a copper catalyst, at least one oxidant and a solvent. The amino acetal formed thereof may be an α-amino acetal having the amino group formed at the α-position of the acetal.

In various embodiments, the method may include the synthesis of an α-amino acetal of formula I,

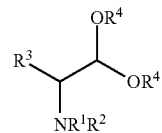

Formula I wherein the method comprises oxidizing a tertiary amine of formula II

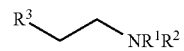

Formula II in the presence of a copper catalyst, one or more alcohols of formula $R^4OH$, at least one oxidant and a solvent, wherein each $R^1$, $R^2$, $R^3$, and $R^4$ is independently selected from the group consisting of substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ cycloalkyl, substituted or unsubstituted $C_3$-$C_{20}$ heterocycloalkyl, substituted or unsubstituted $C_3$-$C_{20}$ cycloalkenyl, and substituted or unsubstituted $C_3$-$C_{20}$ heterocycloalkenyl.

In various embodiments, the method may include the synthesis of an α-amino acetal of formula I,

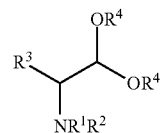

Formula I wherein the method comprises reacting a secondary amine of formula III, $HNR^1R^2$  Formula III with an aliphatic aldehyde of formula IV,

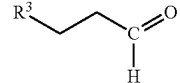

Formula IV in the presence of a copper catalyst, one or more alcohols of formula $R^4OH$, at least one oxidant and a solvent, wherein each $R^1$, $R^2$, $R^3$, and $R^4$ is independently selected from the group consisting of substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ cycloalkyl, substituted or unsubstituted $C_3$-$C_{20}$ heterocycloalkyl, substituted or unsubstituted $C_3$-$C_{20}$ cycloalkenyl, and substituted or unsubstituted $C_3$-$C_{20}$ heterocycloalkenyl.

In various embodiments, the method may include the synthesis of an α-amino acetal of formula I,

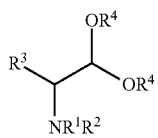

Formula I wherein the method comprises oxidizing an enamine of formula V,

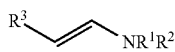

Formula V in the presence of a copper catalyst, one or more alcohols of formula $R^4OH$, at least one oxidant and a solvent, wherein each $R^1$, $R^2$, $R^3$, and $R^4$ is independently selected from the group consisting of substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ cycloalkyl, substituted or unsubstituted $C_3$-$C_{20}$ heterocycloalkyl, substituted or unsubstituted $C_3$-$C_{20}$ cycloalkenyl, and substituted or unsubstituted $C_3$-$C_{20}$ heterocycloalkenyl.

In the context of various embodiments, by "$C_1$-$C_{20}$ alkyl" is meant a straight chain or branched chain hydrocarbon group having from 1 to 20 carbon atoms. A $C_1$-$C_{20}$ alkyl group may be substituted or unsubstituted. Exemplary substituents include $C_1$-$C_{10}$ alkoxy, $C_5$-$C_{20}$ aryl, $C_5$-$C_{20}$ aryloxy, sulfhydryl, $C_5$-$C_{20}$ arylthio, halogen, hydroxyl, amino, sulfonyl, carbonyl, nitro, cyano, and carboxyl. Further, the alkyl group may comprise one or more heteroatoms, such as oxygen, nitrogen, and/or sulfur. $C_1$-$C_{20}$ alkyl groups include, without limitation, methyl, ethyl, n-propyl, isopropyl, n-butyl, iso-butyl, sec-butyl, tert-butyl, n-pentyl, and n-hexyl, among others.

In the context of various embodiments, by "$C_2$-$C_{20}$ alkenyl" is meant a straight chain or branched chain hydrocarbon group containing one or more double bonds and having from 2 to 20 carbon atoms. The $C_2$-$C_{20}$ alkenyl group may be substituted or unsubstituted. Exemplary substituents include $C_1$-$C_{10}$ alkoxy, $C_5$-$C_{20}$ aryl, $C_5$-$C_{20}$ aryloxy, sulfhydryl, $C_5$-$C_{20}$ arylthio, halogen, hydroxyl, amino, sulfonyl, carbonyl, nitro, cyano, and carboxyl. Further, the alkenyl group may comprise one or more heteroatoms, such as oxygen, nitrogen, and/or sulfur. $C_2$-$C_{20}$ alkenyl groups include, without limitation, vinyl, allyl, 1-propenyl, 1-butenyl, 2-butenyl, 3-butenyl, 2-methyl-1-propenyl, and 2-methyl-2-propenyl.

In the context of various embodiments, by "$C_2$-$C_{20}$ alkynyl" is meant a straight chain or branched chain hydrocarbon group containing one or more triple bonds and having from 2 to 20 carbon atoms. The $C_2$-$C_{20}$ alkynyl group may be substituted or unsubstituted. Exemplary substituents include $C_1$-$C_{10}$ alkoxy, $C_5$-$C_{20}$ aryl, $C_5$-$C_{20}$ aryloxy, sulfhydryl, $C_5$-$C_{20}$ arylthio, halogen, hydroxyl, amino, sulfonyl, carbonyl, nitro, cyano, and carboxyl. Further, the alkynyl group may comprise one or more heteroatoms, such as oxygen, nitrogen, and/or sulfur. $C_2$-$C_{20}$ alkynyls include, without limitation, ethynyl, 1-propynyl, 2-propynyl, 1-butynyl, 2-butynyl, and 3-butynyl.

In the context of various embodiments, by "$C_3$-$C_{20}$ cycloalkyl" is meant a group comprising a non-aromatic ring (i.e. an alicyclic ring) wherein each of the atoms forming the ring is a carbon atom. The $C_3$-$C_{20}$ cycloalkyl may be formed by three, four, five, six, seven, eight, nine, or more than nine carbon atoms including twenty carbon atoms. Examples of $C_3$-$C_{20}$ cycloalkyl include cyclopropane, cyclobutane, cyclopentane, cyclohexane, cycloheptane, among others. In certain embodiments, the $C_3$-$C_{20}$ cycloalkyl may be optionally substituted. Exemplary substituents include $C_1$-$C_{10}$ alkoxy, $C_5$-$C_{20}$ aryl, $C_5$-$C_{20}$ aryloxy, sulfhydryl, $C_5$-$C_{20}$ arylthio, halogen, hydroxyl, amino, sulfonyl, carbonyl, nitro, cyano, and carboxyl.

In the context of various embodiments, by "$C_3$-$C_{20}$ cycloalkenyl" is meant a group comprising a non-aromatic ring (i.e. an alicyclic ring) wherein each of the atoms forming the ring is a carbon atom and contains one or more double bonds. The $C_3$-$C_{20}$ cycloalkenyl may be formed by three, four, five, six, seven, eight, nine, or more than nine carbon atoms including twenty carbon atoms. Examples of $C_3$-$C_{20}$ cycloalkenyl include cyclopropene, cyclobutene, cyclopentene, cyclohexene, cycloheptene, 1,3-cyclohexadiene, 1,4-cyclohexadiene, among others. In certain embodiments, the $C_3$-$C_{20}$ cycloalkenyl may be optionally substituted. Exemplary substituents include $C_1$-$C_{10}$ alkoxy, $C_5$-$C_{20}$ aryl, $C_5$-$C_{20}$ aryloxy, sulfhydryl, $C_5$-$C_{20}$ arylthio, halogen, hydroxyl, amino, sulfonyl, carbonyl, nitro, cyano, and carboxyl.

In the context of various embodiments, the terms "$C_3$-$C_{20}$ heterocycloalkyl" and "$C_3$-$C_{20}$ heterocycloalkenyl" have the general above definitions of "$C_3$-$C_{20}$ cycloalkyl" and "$C_3$-$C_{20}$ cycloalkenyl", respectively, except in the alicyclic ring at least one of the carbon atom in the ring is substituted with a heteroatom. Heteroatoms are typically independently selected from oxygen, sulfur, nitrogen, and phosphorus, but are not limited to those atoms. The $C_3$-$C_{20}$ heterocycloalkyl or $C_3$-$C_{20}$ heterocycloalkenyl may be formed by three, four, five, six, seven, eight, nine, or more than nine atoms including twenty atoms. Examples of $C_3$-$C_{20}$ heterocycloalkyls and $C_3$-$C_{20}$ heterocycloalkenyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazohdme, oxazoline, oxazolidine, oxazolidinone, thiazoline, thiazolidine, and 1,3-oxathiolane. In certain embodiments, the $C_3$-$C_{20}$ heterocycloalkyls and $C_3$-$C_{20}$ heterocycloalkenyls may be optionally substituted. Exemplary substituents include alkoxy, aryl, aryloxy, sulfhydryl, arylthio, halogen, hydroxyl, amino, and carboxyl.

In various embodiments, the copper catalyst may include copper (II) halide or copper (I) halide. The halide may include iodide, bromide and chloride.

In various embodiments, the copper catalyst may be selected from the group consisting of $CuBr_2$, $CuI_2$, CuI, and CuBr.

In various embodiments, the copper catalyst may be $CuBr_2$ or $CuI_2$.

In various embodiments, the copper catalyst may be CuI, CuBr or $CuBr_2$.

In yet further various embodiments, the copper catalyst may include copper salts such as, but not limited to, copper (II) acetate ($Cu(OAc)_2$) and copper (II) triflate $Cu(OTf)_2$.

In various embodiments, the one or more alcohols may be methanol or ethanol. In various other embodiments, the alcohol is n-propanol, isopranol, isubutanol, tert-butanol, n-butanol, n-pentanol. Also contemplated are alcohols that have two or more hydroxy groups, i.e. are diols, triols, etc. Exemplary diols include, but are not limited to, 1,2-ethanediol, 1,3-propanediol, 1,4-butanediol, and glycerin.

In various embodiments, $R^1$ and $R^2$ may be selected from the group consisting of substituted or unsubstituted $C_1$-$C_{10}$ alkyl and substituted or unsubstituted $C_3$-$C_{10}$ cycloalkyl.

In various embodiments, $R^3$ may be substituted or unsubstituted $C_1$-$C_{10}$ alkyl.

In various embodiments, the solvent may include an organic solvent. For example, the organic solvent may include acetonitrile (MeCN), methanol (MeOH), 1,2-dichloroethane (DCE), tetrahydrofuran (THF) and dimethyl sulfoxide (DMSO).

In one embodiment, the solvent may be MeOH.

In another embodiment, the solvent may be MeCN.

In various embodiments, a mixture of organic solvents may also be used. For example, a mixture of MeOH and MeCN may be used. In various embodiments, the solvent may include a mixture of MeOH and MeCN having a volume ratio of MeOH:MeCN in a range of between about 1:1 and about 1:10, such as about 1:2, about 1:3, about 1:4, about 1:5, about 1:6, about 1:7, about 1:8 and about 1:9.

In various embodiments, the amine may be oxidized by air or molecular oxygen ($O_2$).

In yet various embodiments, oxidants such as a peroxide may be used. For example, tert-butyl hydroperoxide, di-tert-butyl peroxide, tert-butyl benzoylperoxide, or a mixture thereof may be used.

In one embodiment, the oxidant may be tert-butyl hydroperoxide.

In various embodiments, the reaction may be carried out at a temperature of less than about 100° C. For example, the reaction may be carried out at a temperature of less than about 60° C.

In one embodiment, the reaction may be carried out at a temperature of about 40° C.

In another embodiment, the reaction may be carried out at room temperature.

In various embodiments, the reaction may be optionally carried out in the presence of a nitrogen donor ligand. The nitrogen donor ligand acts a ligand to suppress the formation of undesirable side products during the reaction process.

In one embodiment the nitrogen donor ligand used may be N,N,N',N'-tetramethylethylenediamine (TMEDA). Optionally, when TMEDA is used, the tertiary amine is N,N-dicyclohexyl-n-butylamine.

In various embodiments, the molar ratio of copper catalyst: TMEDA may be between about 1:1 and about 1:5. For example, the molar ratio of copper catalyst:TMEDA may be about 1:2.

In various embodiments, the reaction is carried out at atmospheric pressure.

The reaction may be carried out over a short period to a long period. In various embodiments, the reaction may be carried out for a period of between about 1 and about 100 hours.

In one embodiment, the reaction may be carried out for a period of between about 5 and about 48 hours.

In various embodiments, N,N-dicyclohexyl-n-butylamine is oxidized in the presence of $CuBr_2$, oxygen, TMEDA, MeOH and MeCN.

In one embodiment, N,N-dicyclohexyl-n-butylamine (0.5 mmol, 1 equiv.) is oxidized in an oxygen atmosphere at 40° C. using 25 mol % (0.25 equiv.) of $CuBr_2$ and 50 mol % (0.5 equiv.) of TMEDA as the catalytic system, the volume ratio of (0.2 mL) MeOH to (2 mL) MeCN being about 1:4.

In various embodiments, dibenzylamine and butyraldehyde are reacted in the presence of CuI, tert-butyl hydroperoxide, MeOH and MeCN.

In one embodiment, dibenzylamine (0.5 mmol, 1 equiv.) and butyraldehyde (0.75 mmol) are reacted at about 40° C. in the presence of CuI (40 mol %, 0.4 equiv.), tert-butyl hydroperoxide (~5.5 M in decane, 1.1 equiv.), and the volume ratio of (0.4 mL) MeOH to (2 mL) MeCN was 1:5.

In order that the invention may be readily understood and put into practical effect, particular embodiments will now be described by way of the following non-limiting examples.

EXAMPLES

Example 1

Copper-Catalyzed Rearrangement of Tertiary Amines Via Aliphatic C—H Bond Oxidation in Air or Oxygen In this example, a novel rearrangement of tertiary amines via aliphatic C—H bond oxidation in dioxygen-copper catalytic systems for the direct synthesis of α-amino acetals is provided. Compared with expensive metal catalyst and stoichiometric metal oxidants employed in the traditional methods for C—H bond oxidation, this catalytic system has the obvious advantages of mild reaction conditions and the use of air or oxygen as the oxidant.

Furthermore, a mechanism to account for the product observed was proposed based on the trapping and deuterium labelling experiments.

General Procedures

All reactions were carried out without exclusion of air or moisture unless otherwise stated. Copper salts, and N,N,N',N'-tetramethylethylenediamine (TMEDA) were purchased from commercial suppliers, and used directly as received. Commercial solvents and reagents were used without further purification. Tertiary aliphatic amines 1(a-i), and enamine were synthesized according to literatures (Y. H. Ju, R. S. Varma, *Green Chem.*, 2004, 6, 219-221; Y. H. Ju, R. S. Varma, *J. Org. Chem.*, 2006, 71, 135-141; C. R. Smith, T. V. RajanBabu, *Org. Lett.*, 2008, 10(8), 1657-1659; D. M. Hodgson, C. D. Bray, N. D. Kindon, N. J. Reynolds, S. J. Coote, J. M. Urn, and K. N. Houk, *J. Org. Chem.* 2009, 74, 1019-1028). Reactions were monitored through thin layer chromatography [Merck 60 F254 precoated silica gel plate (0.2 mm thickness)]. Subsequent to elution, spots were visualized using UV radiation (254 nm) on Spectroline Model ENF-24061/F 254 nm. Further visualization was possible using basic solution of potassium permanganate or acidic solution of ceric molybdate as stain, followed by heating on a hot plate. Flash chromatography was performed using Merck silica gel 60 with distilled solvents. Infrared spectra were recorded on a Shimadzu IR Prestige-21 FT-IR. Liquid samples were examined as film between NaCl salt plates. HRMS spectra were recorded on a Waters Q-T of Permier Spectrometer. $^1$H NMR and $^{13}$C NMR spectra were recorded using Bruker Avance 300, 400 and 500 MHz spectrometers. Chemical shifts for $^1$H NMR spectra are reported as δ in units of parts per million (ppm) downfield from $SiMe_4$ (δ 0.0) and relative to the signal of chloroform-d (δ 7.260, singlet). Multiplicities were given as: s (singlet); brs (broad singlet); d (doublet); t (triplet); q (quartet); dd (doublets of doublet); ddd (doublets of doublets of doublet); td (triplet of doublet); m (multiplets); ddt (doublet of doublet of triplet) and etc. Coupling constants are reported as a J value in Hz. Carbon nuclear magnetic resonance spectra ($^{13}$C NMR) are reported as δ in units of parts per million (ppm) downfield from SiMe$_4$ (δ 0.0) and relative to the signal of chloroform-d (δ 77.00, triplet).

Figure 1:
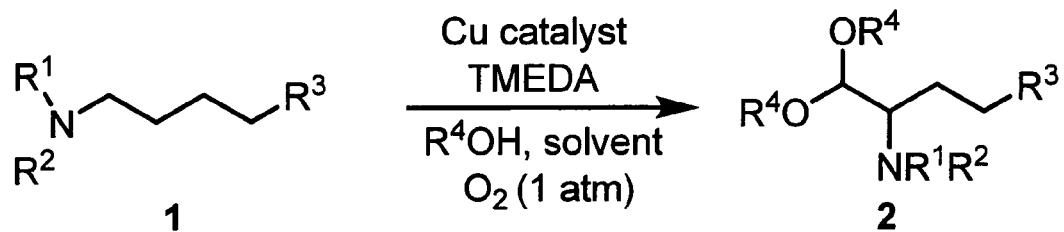
FIG. 1(A) shows a method for copper-catalyzed oxidative rearrangement of tertiary amines via C—H bond oxidation.
FIG. 1(B) shows a method for copper-catalyzed C—H bond amination for direct synthesis of α-amino acetals from secondary amines and aliphatic aldehydes.
Figure 1:
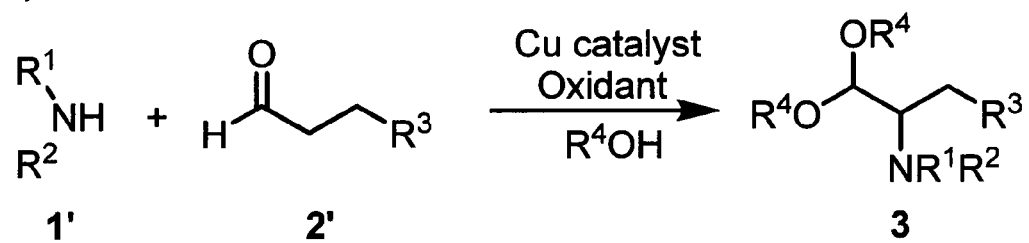

General Experimental Procedure for Copper-Catalyzed Oxidative Rearrangement of Tertiary Aliphatic Amines Typical procedure for the copper-catalyzed oxidative rearrangement of tertiary amines (N,N-dicyclohexyl-n-butylamine 1a as an example) is illustrated in FIG. 1. N,N-dicyclohexyl-n-butylamine 1a (0.118 g, 0.5 mmol) was added to a mixture of CuBr$_2$ (28 mg, 0.125 mmol), and TMEDA (29 mg, 0.25 mmol) in methanol (0.5 mL)/acetonitrile (2.0 mL) in air at room temperature. The mixture was stirred at 40° C. using O$_2$ balloon until N,N-dicyclohexyl-n-butylamine 1a was completely converted by TLC detection. The resulting reaction mixture was mixed with a small amount of silica gel and concentrated. The crude product was purified by flash column chromatography (silica gel; triethylamine/ethyl acetate/hexane=0.1:1:100) to afford the desired product 2a as a light yellowish oil (99 mg, 66% yield) and a trace of product 3a as a light yellowish oil. Then the product 2a was dissolved in dichloromethane, hexane was added into it, and solvent was evaporated to obtain the crystal.

N-cyclohexyl-N-(1,1-dimethoxybutan-2-yl)cyclohexanamine (2a)

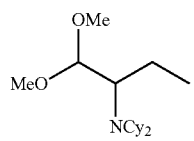

$R_f$=0.79 (hexane:ethyl acetate=3:1); mp: 73.5-74.2° C.; $^1$H NMR (CDCl$_3$, 400 MHz) δ 4.150-4.145 (d, J=2.02 Hz, 1H), 3.43 (s, 3H), 3.42 (s, 3H), 2.74-2.64 (m, 3H), 1.74-1.71 (m, 4H), 1.57-0.94 (m, 16H), 0.92-0.88 (t, J=7.39 Hz, 3H) ppm; $^{13}$C NMR (CDCl$_3$, 100 MHz) δ 112.3, 58.3, 56.64, 56.59, 54.1 (CH$_3$×2), 34.6 (CH$_2$×2), 34.5 (CH$_2$×2), 26.8 (CH$_2$×4), 26.0 (CH$_2$×2), 19.0, 12.4 ppm; FTIR (neat): v=2930, 1215, 754, 669, 494 cm$^{-1}$; HRMS (ESI, m/z): calcd for C$_{18}$H$_{36}$NO$_2$$^+$ [M+H]$^+$ 298.2746, found: 298.2743.

N-cyclohexyl-N-(1,1-dimethoxypropan-2-yl)cyclohexanamine (3a')

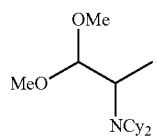

$R_f$=0.61 (hexane:ethyl acetate=3:1); $^1$H NMR (CDCl$_3$, 400 MHz) δ 4.04-4.03 (d, J=4.05 Hz, 1H), 3.43 (s, 3H), 3.42 (s, 3H), 2.99-2.93 (m, 1H), 2.67-2.61 (m, 2H), 1.74-1.70 (m, 4H), 1.63-1.51 (m, 6H), 1.36-1.16 (m, 8H), 1.05-0.95 (m, 5H) ppm; $^{13}$C NMR (CDCl$_3$, 100 MHz) δ 111.5, 56.3, 56.1, 54.7 (CH$_3$×2), 51.7, 34.6 (CH$_2$×2), 33.9 (CH$_2$×2), 26.9 (CH$_2$×2), 26.6 (CH$_2$×2), 26.0 (CH$_2$×2), 14.1 ppm; FTIR (neat): v=2930, 1215, 754, 669, 494 cm$^{-1}$; HRMS (ESI, m/z): calcd for C$_{17}$H$_{34}$NO$_2$$^+$ [M+H]$^+$ 284.2590, found: 284.2597.

N-cyclohexyl-N-(1,1-dimethoxyhexan-2-yl)cyclohexanamine (2b)

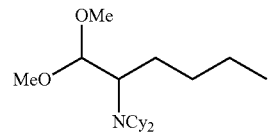

The product was prepared by above general procedure and the same chemicals except employing N-cyclohexyl-N-hexylcyclohexanamine (1b) (0.132 g, 0.5 mmol). After 6 h, the crude product was purified by flash column chromatography (silica gel; triethylamine/ethyl acetate/hexane=0.1:1:100) to afford the desired product 2b as a light yellowish oil (0.105 g, 65% yield); $R_f$=0.81 (hexane:ethyl acetate=3:1); $^1$H NMR (CDCl$_3$, 400 MHz) δ 4.14 (brs, 1H), 3.43 (s, 3H), 3.42 (s, 3H), 2.75-2.69 (m, 3H), 1.73-1.72 (m, 4H), 1.57-1.15 (m, 20H), 1.04-0.96 (m, 2H), 0.90-0.86 (t, J=7.24 Hz, 3H) ppm; $^{13}$C NMR (CDCl$_3$, 100 MHz) δ 112.4, 56.69, 56.63, 56.58, 54.1 (CH$_3$×2), 34.6 (CH$_2$×4), 29.9, 26.8 (CH$_2$×4), 26.0 (CH$_2$×2), 25.9, 23.1, 14.2 ppm; FTIR (neat): v=2930, 1215, 754, 669, 494 cm$^{-1}$; HRMS (ESI, m/z): calcd for C$_2$H$_4$NO$_2$$^+$ [M+H]$^+$ 326.3059, found: 326.3066.

N-cyclohexyl-N-(1,1-dimethoxydodecan-2-yl)cyclohexanamine (2c)

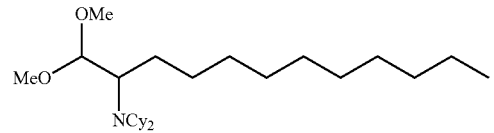

The product was prepared by above general procedure and the same chemicals except employing N-cyclohexyl-N-dodecylcyclohexanamine (1c) (0.174 g, 0.5 mmol). After 24 h, The crude product was purified by flash column chromatography (silica gel; triethylamine/ethyl acetate/hexane=0.1:1:100) to afford the desired product 2c as a light yellowish oil (0.125 g, 61% yield); $R_f$=0.83 (hexane:ethyl acetate=3:1); H NMR (CDCl$_3$, 400 MHz) δ 4.138-4.134 (d, J=1.57 Hz, 1H), 3.43 (s, 3H), 3.42 (s, 3H), 2.74-2.71 (m, 3H), 1.57-1.21 (m, 32H), 1.04-0.98 (m, 2H), 0.89-0.86 (t, J=7.01 Hz, 3H) ppm; $^{13}$C NMR (CDCl$_3$, 100 MHz) δ 112.4, 56.67, 56.61 (CH$_2$×2), 54.1 (CH$_3$×2), 34.59 (CH$_2$×2), 34.56 (CH$_2$×2), 31.9, 30.1, 29.7, 29.6 (CH$_2$×2), 29.4, 27.6, 26.8 (CH$_2$×4), 26.2, 26.0 (CH$_2$×2), 22.7, 14.1 ppm; FTIR (neat): v=2930, 1215, 754, 669, 494 cm$^{-1}$; HRMS (ESI, m/z): calcd for C$_{26}$H$_{52}$NO$_2$$^+$ [M+H]$^+$ 410.3998, found: 410.3998.

Methyl 4-(dicyclohexylamino)-5,5-dimethoxypentanoate (2d)

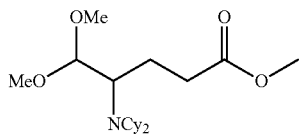

The product was prepared by above general procedure and the same chemicals except employing methyl 5-(dicyclohexylamino)pentanoate (1d) (0.147 g, 0.5 mmol). After 12 h, the crude product was purified by flash column chromatography (silica gel; triethylamine/ethyl acetate/hexane=0.1:2:100) to afford the desired product 2d as a light yellowish oil (0.106 g, 60% yield); $R_f$=0.65 (hexane:ethyl acetate=3:1); $^1$H NMR (CDCl$_3$, 400 MHz) δ 4.183-4.178 (d, J=1.97 Hz, 1H), 3.64 (s, 3H), 3.42 (s, 3H), 3.41 (s, 3H), 2.85-2.81 (m, 1H), 2.73-2.68 (m, 2H), 2.53-2.28 (m, 2H), 1.87-1.79 (m, 1H), 1.74-1.54 (m, 9H), 1.47-1.45 (m, 2H), 1.33-1.16 (m, 8H), 1.04-0.94 (m, 2H) ppm; $^{13}$C NMR (CDCl$_3$, 100 MHz) δ 174.9, 111.4, 56.4 (CH$_2$×2), 55.7, 54.1 (CH$_3$×2), 51.3, 34.6 (CH$_2$×2), 34.3 (CH$_2$×2), 31.8, 26.8 (CH$_2$×2), 26.7 (CH$_2$×2), 25.9 (CH$_2$×2), 21.7 ppm; FTIR (neat): v=2930, 1730, 1449, 1215, 754, 669, 494 cm$^{-1}$; HRMS (ESI, m/z): calcd for C$_{20}$H$_{38}$NO$_4^+$ [M+H]$^+$ 356.2801, found: 356.2799.

N-(6-bromo-1,1-dimethoxyhexan-2-yl)-N-cyclohexylcyclohexanamine (2e)

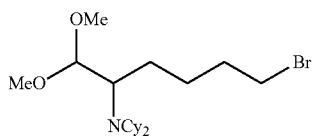

The product was prepared by above general procedure and the same chemicals except employing N-(6-bromohexyl)-N-cyclohexylcyclohexanamine (1e) (0.172 g, 0.5 mmol). After 6 h, the crude product was purified by flash column chromatography (silica gel; triethylamine/ethyl acetate/hexane=0.1:1:100) to afford the desired product 2e as a light yellowish oil (0.109 g, 54% yield); $R_f$=0.75 (hexane:ethyl acetate=3:1); H NMR (CDCl$_3$, 400 MHz) δ 4.15 (brs, 1H), 3.44-3.39 (m, 8H), 2.74-2.72 (m, 3H), 1.89-1.82 (m, 2H), 1.72-1.64 (m, 5H), 1.57-1.55 (m, 4H), 1.48-1.18 (m, 13H), 1.00-0.98 (m, 2H) ppm; $^{13}$C-NMR (CDCl$_3$, 100 MHz) δ 112.2, 56.8, 56.7, 56.5, 54.1 (CH$_3$×2), 34.6 (CH$_2$×2), 34.5 (CH$_2$×2), 34.2, 33.3, 26.8 (CH$_2$×4), 26.2, 26.0 (CH$_2$×2), 25.2 ppm; FTIR (neat): v=2930, 1449, 1215, 754, 669, 494 cm$^{-1}$; HRMS (ESI, m/z): calcd for C$_{20}$H$_{39}$BrNO$_2^+$ [M+H]$^+$ 404.2164, found: 404.2164.

N-cyclohexyl-N-(1,1-dimethoxyhex-5-en-2-yl)cyclohexanamine (2f)

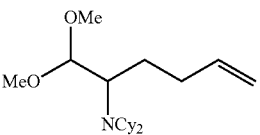

The product was prepared by above general procedure and the same chemicals except employing N-cyclohexyl-N-(hex-5-enyl)cyclohexanamine (1f) (0.131 g, 0.5 mmol). After 24 h, the crude product was purified by flash column chromatography (silica gel; triethylamine/ethyl acetate/hexane=0.1:1:100) to afford the desired product 2f as a light yellowish oil (98 mg, 61% yield); $R_f$=0.5 (hexane:ethyl acetate=3:1); $^1$H NMR (CDCl$_3$, 400 MHz) δ 5.87-5.80 (m, 1H), 5.02-4.98 (d, J=17.18 Hz, 1H), 4.92-4.89 (d, J=10.22 Hz, 1H), 4.154-4.150 (d, J=1.89 Hz, 1H), 3.42 (s, 3H), 3.41 (s, 3H), 2.78-2.70 (m, 3H), 2.28-2.20 (m, 1H), 2.02-1.90 (m, 1H), 1.74-1.72 (m, 4H), 1.57-1.42 (m, 8H), 1.32-1.17 (m, 8H), 1.04-0.95 (m, 2H) ppm; $^{13}$C NMR (CDCl$_3$, 100 MHz) δ 139.9, 113.6, 112.1, 56.6 (CH$_2$×2), 56.1, 54.1 (CH$_3$×2), 34.6 (CH$_2$×2), 34.4 (CH$_2$×2), 31.6, 26.8 (CH$_2$×4), 26.0 (CH$_2$×2), 25.5 ppm; FTIR (neat): v=2930, 1638, 1215, 754, 669 cm$^{-1}$; HRMS (ESI, m/z): calcd for C$_{20}$H$_{38}$NO$_2^+$ [M+H]$^+$ 324.2903, found: 324.2901.

2-(4-(dicyclohexylamino)-5,5-dimethoxypentyl)isoindoline-1,3-dione (2g)

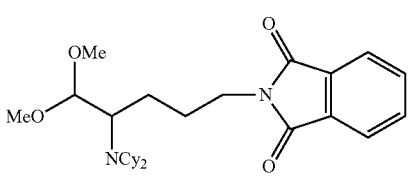

The product was prepared by above general procedure and the same chemicals except employing 2-(5-(dicyclohexylamino)pentyl)isoindoline-1,3-dione (1g) (0.198 g, 0.5 mmol). After 20 h, the crude product was purified by flash column chromatography (silica gel; diethyl ether/hexane=2:100) to afford the desired product 2g as a light yellowish oil (0.128 mg, 56% yield); $R_f$=0.50 (hexane:ethyl acetate=3:1); $^1$H NMR (400 MHz, CDCl$_3$): δ 7.82-7.78 (m, 2H), 7.69-7.64 (m, 2H), 4.122-4.117 (d, J=1.94 Hz, 1H), 3.66-3.62 (m, 2H), 3.40 (s, 3H), 3.73 (s, 3H), 2.76-2.66 (m, 3H), 1.96-1.85 (m, 1H), 1.74-1.34 (m, 13H), 1.27-1.12 (m, 8H), 1.00-0.89 (m, 2H) ppm; $^{13}$C NMR (100 MHz, CDCl$_3$): δ 168.4 (C×2), 133.6 (CH$_2$×2), 132.2 (C×2), 123.0 (CH$_2$×2), 111.8, 56.7, 56.5, 56.2, 54.0 (CH$_3$×2), 38.4, 34.6 (CH$_2$×2), 34.3 (CH$_2$×2), 26.69 (CH$_2$×2), 26.66 (CH$_2$×2), 26.5, 25.9 (CH$_2$×2), 23.3 ppm;

FTIR (neat): v=3460, 2930, 1709, 1396, 1215, 754, 669, 494 cm$^{-1}$; HRMS (ESI, m/z): calcd for $C_{27}H_{41}N_2O_2^+$ [M+H]$^+$ 457.3066, found: 457.3066.

4-(dicyclohexylamino)-5,5-dimethoxypentyl acetate (2h)

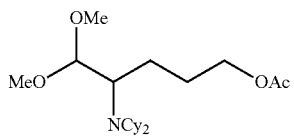

The product was prepared by above general procedure and the same chemicals except employing 5-(dicyclohexylamino)pentyl acetate (1h) (0.154 g, 0.5 mmol). After 20 h, The crude product was purified by flash column chromatography (silica gel; diethyl ether/hexane=2:100) to afford the desired product 2h as a light yellowish oil (0.101 mg, 55% yield); $R_f$=0.60 (hexane:ethyl acetate=3:1); $^1$H NMR (400 MHz, CDCl$_3$): δ 4.158-4.153 (d, J=1.77 Hz, 1H), 4.08-3.98 (m, 2H), 3.43 (s, 3H), 3.42 (s, 3H), 2.75-2.69 (m, 3H), 2.01 (s, 3H), 1.90-1.80 (m, 1H), 1.74-1.71 (m, 4H), 1.57-1.36 (m, 9H), 1.31-1.17 (m, 8H), 1.04-0.94 (m, 2H) ppm; $^{13}$C NMR (100 MHz, CDCl$_3$): δ 171.3, 112.0, 65.2, 56.8, 56.7, 56.4, 54.0 (CH$_3$×2), 34.6 (CH$_2$×2), 34.4 (CH$_2$×2), 26.73 (CH$_2$×4), 26.67, 25.9 (CH$_2$×2), 22.5, 21.0 ppm; FTIR (neat): v=2930, 1730, 1215, 756, 669, 494 cm$^{-1}$; HRMS (ESI, m/z): calcd for $C_{21}H_{40}NO_4^+$ [M+H]$^+$ 370.2957, found: 370.2952.

N-(1,1-dimethoxybutan-2-yl)-N-isopropylcyclohexanamine (2i)

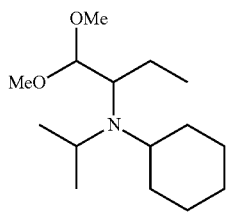

The product was prepared by above general procedure and the same chemicals except employing N-butyl-N-isopropylcyclohexanamine (1i) (98 mg, 0.5 mmol). After 24 h, the crude product was purified by flash column chromatography (silica gel; triethylamine/ethyl acetate/hexane=0.1:1:100) to afford the desired product 2i as a light yellowish oil (58 mg, 45% yield); $R_f$=0.67 (hexane:ethyl acetate=3:1); $^1$H NMR (400 MHz, CDCl$_3$): δ 4.155-4.150 (d, J=2.09 Hz, 1H), 3.43 (s, 3H), 3.41 (s, 3H), 3.33-3.23 (m, 1H), 2.72-2.64 (m, 2H), 1.75-1.72 (m, 2H), 1.61-1.18 (m, 10H), 0.99-0.95 (m, 6H), 0.92-0.88 (t, J=7.43 Hz, 3H) ppm; $^{13}$C NMR (100 MHz, CDCl$_3$): δ 111.9, 57.7, 56.6, 56.5, 53.5, 44.9, 34.4, 34.3, 26.8, 26.0, 23.5, 23.0, 18.9, 12.4 ppm; FTIR (neat): v=2930, 1215, 754, 669, 494 cm$^{-1}$; HRMS (ESI, m/z): calcd for $C_{15}H_{32}NO_2^+$ [M+H]$^+$ 258.2433, found: 258.2433.

methyl 4-(((S)-1-(tert-butyldimethylsilyloxy)-3-methylbutan-2-yl)(isopropyl)amino)-5,5-dimethoxypentanoate (2j)

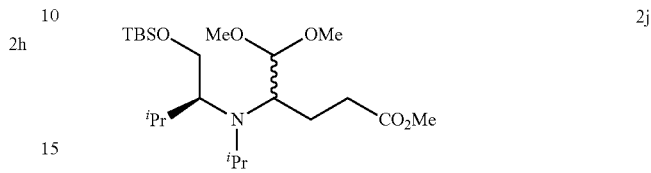

The product was prepared by above general procedure and the same chemicals except employing (S)-methyl 5-((1-(tert-butyldimethylsilyloxy)-3-methylbutan-2-yl)(isopropyl) amino)pentanoate (1j) (0.186 g, 0.5 mmol). After 48 h, the crude product was purified by flash column chromatography (silica gel; diethyl ether/hexane=1:100) to afford the desired product 2j as a light yellowish oil (0.112 g, 52% yield, 61:39 de). One isomer: $R_f$=0.72 (hexane:ethyl acetate=3:1); $^1$H NMR (400 MHz, CDCl$_3$): δ 4.181-4.176 (d, J=1.89 Hz, 1H), 3.72-3.58 (m, 5H), 3.44-3.35 (m, 7H), 3.09-3.05 (m, 1H), 2.59-2.55 (m, 1H), 2.52-2.48 (t, J=7.71 Hz, 2H), 2.00-1.86 (m, 2H), 1.78-1.69 (m, 1H), 1.01-0.99 (d, J=6.64 Hz, 6H), 0.98-0.96 (d, J=6.86 Hz, 3H), 0.92-0.91 (d, J=6.68 Hz, 3H), 0.88 (s, 9H), 0.03 (s, 6H); $^{13}$C NMR (100 MHz, CDCl$_3$): δ 174.8, 112.5, 64.3, 61.5, 56.1, 56.0, 54.5, 51.2, 46.1, 31.7, 29.5, 25.9 (CH$_3$×3), 23.5, 23.4, 22.8, 22.2, 19.8, 18.2, −5.6, −5.8 ppm; FTIR (neat): v=3019, 1730, 1215, 756, 669, 484 cm$^{-1}$; HRMS (ESI, m/z): calcd for $C_{22}H_{48}NO_5Si^+$ [M+H]$^+$ 434.3302, found: 434.3298; $[α]_D^{20}$=−31.0° (c=2.2, CH$_2$Cl$_2$).

Another isomer: $R_f$=0.71 (hexane:ethyl acetate=3:1); $^1$H NMR (400 MHz, CDCl$_3$): δ 4.316-4.312 (d, J=1.44 Hz, 1H), 3.79-3.75 (m, 1H), 3.64 (s, 3H), 3.55-3.51 (m, 1H), 3.50-3.44 (m, 4H), 3.37 (s, 3H), 2.90-2.88 (m, 1H), 2.60-2.48 (m, 2H), 2.40-2.32 (m, 1H), 2.00-1.83 (m, 2H), 1.62-1.63 (m, 1H), 1.04-1.02 (d, J=6.49 Hz, 3H), 0.98-0.97 (d, J=6.76 Hz, 3H), 0.93-0.89 (m, 15H), 0.049-0.045 (m, 6H); C NMR (100 MHz, CDCl$_3$): δ 174.8, 110.4, 64.8, 61.4, 56.6, 56.0, 54.9, 51.3, 45.9, 32.0, 28.3, 25.9 (CH$_3$×3), 23.6, 22.8, 22.4, 21.9, 20.3, 18.2, −5.6, −5.8 ppm; FTIR (neat): v=3019, 1730, 1215, 756, 669, 484 cm$^{-1}$; HRMS (ESI, m/z): calcd for $C_{22}H_{48}NO_5Si^+$ [M+H]$^+$ 434.3302, found: 434.3298.

N,N-diisobutyl-1,1-dimethoxyhexan-2-amine (2k)

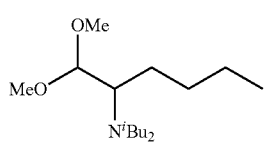

The product was prepared by above general procedure and the same chemicals except employing N,N-diisobutylhex-1-en-1-amine (1k) (0.105 mg, 0.5 mmol). After 5 h, the crude product was purified by flash column chromatography (silica gel; triethylamine/ethyl acetate/hexane=0.1:1:100) to afford the desired product 2k as a light yellowish oil (85 mg, 62% yield); $R_f$=0.65 (hexane:ethyl acetate=3:1); $^1$H NMR (400

MHz, CDCl₃): δ 4.22-4.21 (d, J=4.67 Hz, 1H), 3.371-3.368 (m, 6H), 2.59-2.55 (m, 1H), 2.34-2.17 (m, 4H), 1.66-1.49 (m, 3H), 1.45-1.24 (m, 5H), 0.90-0.84 (m, 15H) ppm; $^{13}$C NMR (100 MHz, CDCl₃): δ 107.8, 61.6, 60.6 (CH₂×2), 54.8 (CH₃× 2), 29.8, 27.2 (CH₂×2), 26.6, 23.0, 21.0 (CH₃×2), 20.8 (CH₃× 2), 14.1 ppm; FTIR (neat): ν=2955, 1456, 1215, 756, 669, 494 cm$^{-1}$.

Figure 2:
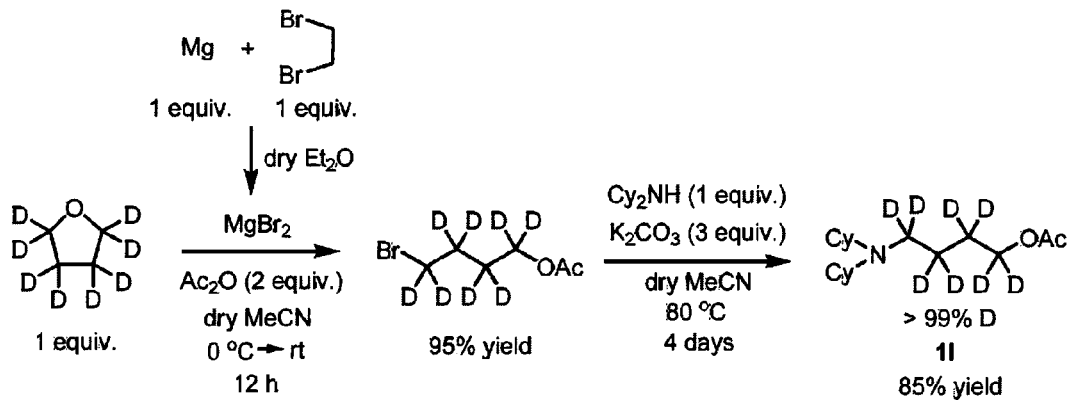
FIG. 2(A) shows a possible mechanism of forming 4-(dicyclohexylamino)butyl-D8 acetate (1l) of Example 1.
FIG. 2(B) shows a possible mechanism of forming 3-(dicyclohexylamino)-4,4-dimethoxybutyl-D5 acetate (2l) of Example 1.
Figure 2:
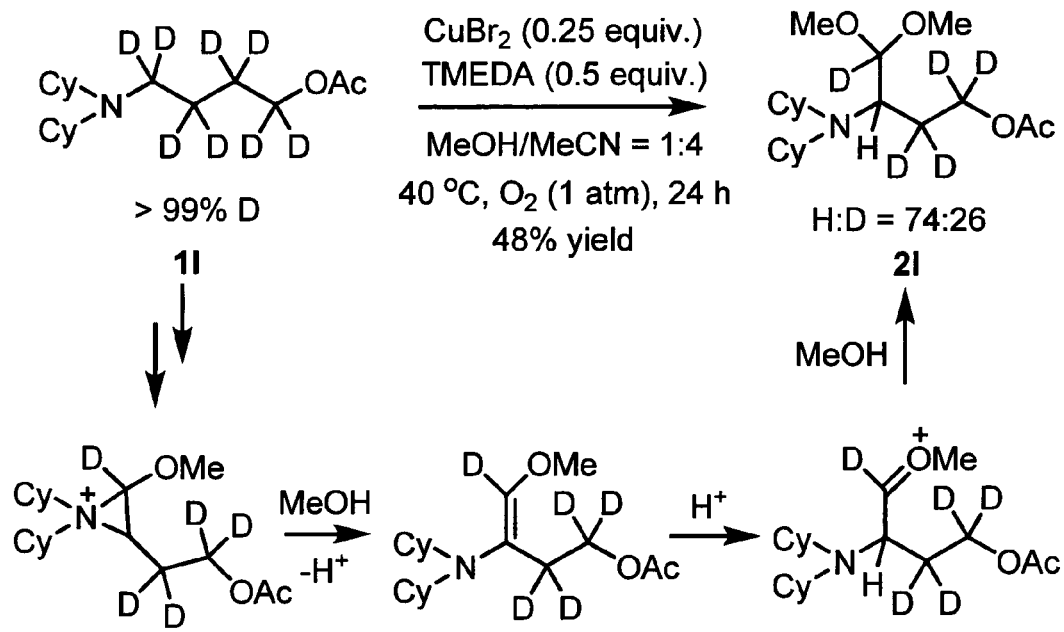

Deuterium Labelling Experiment 4-(dicyclohexylamino)butyl-D8 acetate (1l): The product was prepared by above general procedure (Y. H. Ju, R. S. Varma, *Green Chem.*, 2004, 6, 219-221; Y. H. Ju, R. S. Varma, *J. Org. Chem.*, 2006, 71, 135-141) to afford product as colorless oil; $^1$H NMR (400 MHz, CDCl₃): δ 2.48-2.43 (m, 2H), 2.00 (s, 3H), 1.71-1.64 (m, 8H), 1.57-1.54 (m, 2H), 1.23-1.12 (m, 8H), 1.06-0.97 (m, 2H); $^{13}$C NMR (100 MHz, CDCl₃): δ 171.1, 57.8 (CH₂×2), 31.7 (CH₂×4), 26.4 (CH₂×4), 26.2 (CH₂×2), 20.9 ppm; HRMS (ESI, m/z): calcd for $C_{18}H_{26}D_8NO_2^+$ [M+H]$^+$ 304.3092, found: 304.3089; FIG. 2(A).

3-(dicyclohexylamino)-4,4-dimethoxybutyl-D5 acetate (2l)

The product was prepared by above general procedure and the same chemicals except employing 4-(dicyclohexylamino)butyl-D8 acetate (1l) (0.151 g, 0.5 mmol). After 24 h, The crude product was purified by flash column chromatography (silica gel; triethylamine/ethyl acetate/hexane=0.1:1:100) to afford the desired product 2l as a light yellowish oil (86 mg, 48% yield); R$_f$=0.60 (hexane:ethyl acetate=3:1); $^1$H NMR (400 MHz, CDCl₃): 3.42 (s, 3H), 3.40 (s, 3H), 2.92 (s, 0.74H), 2.72-2.66 (m, 2H), 2.02 (s, 3H), 1.74-1.69 (m, 4H), 1.56-1.54 (m, 4H), 1.50-1.42 (m, 2H), 1.30-1.16 (m, 8H), 1.04-0.94 (m, 2H) ppm; $^{13}$C NMR (100 MHz, CDCl₃): δ 171.2, 56.4 (CH₂×2), 54.2 (CH₃×2), 52.8, 34.4 FTIR (neat): ν=2930, 1215, 754, 669, 494 cm$^{-1}$; HRMS (ESI, m/z): calcd for $C_{20}H_{33}D_5NO_4^+$ [M+H]$^+$ 361.3115, found: 361.3109; FIG. 2(B).

Isolation of the Intermediate

N,N-dicyclohexyl-n-butylamine 1a (0.118 g, 0.5 mmol) was added to a mixture of CuBr₂ (28 mg, 0.125 mmol), and TMEDA (29 mg, 0.25 mmol) in methanol (0.2 mL)/acetonitrile (2.0 mL) in air at room temperature. The mixture was stirred at 40° C. using O₂ balloon until N,N-dicyclohexyl-n-butylamine 1a was completely converted by TLC detection. A white solid (about 10 mg, about 8% yield) was isolated from the reaction mixture by a simple filtration and washed using MeCN (1 mL×3). Then the white solid was dissolved in methanol, hexane was added into it, and solvent was evaporated to obtain the crystal (Cy₂NH₂Br).

Dicyclohexylammonium bromide

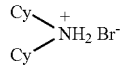

$^1$H NMR (CD₃OD, 400 MHz) δ 3.23-3.18 (m, 2H), 2.09-2.07 (m, 4H), 1.90-1.86 (m, 4H), 1.75-1.71 (m, 2H), 1.41-1.20 (m, 10H) ppm; $^{13}$C NMR (CD₃OD, 100 MHz) δ 54.6 (CH₂×2), 30.6 (CH₂×4), 26.2 (CH₂×2), 25.5 (CH₂×4) ppm.

Results and Discussion

When N,N-dicyclohexyl-n-butylamine 1a was subjected to copper (II) bromide and oxygen in methanol/acetonitrile at 40° C., product α-amino acetal 2a in low yield (11%) (Table 1, entry 2) was unexpectedly obtained. The structure of 2a was confirmed by single crystal X-ray analysis (see below). Most of the substrate 1a was converted into N,N-dicyclohexylformamide (62%) (Table 1, entry 2). The reaction did not proceed without copper catalyst (Table 1, entry 1). Since nitrogen donor ligands is known to play an important role in dioxygen activation, a series of nitrogen donor ligands were tested in this reaction. It was found out that N,N,N',N'-tetramethylethylenediamine (TMEDA) was the best ligand for this reaction to suppress the formation of N,N-dicyclohexylformamide, affording the desired α-amino acetals 2a in 51% isolated yield when the TMEDA/copper (II) bromide ratio was 2:1 (Table 1, entry 3). It is noteworthy that the reaction proceeded even under air without a significant decrease in yield (Compare Table 1, entry 4 with Table 1, entry 17). Among the various solvents screened, acetonitrile emerged as the best solvent for this reaction, generating the desired product in 51% yield (Table 1, entry 3). Other solvents such as methanol, 1,2-dichloroethane (DCE), and tetrahydrofuran (THF) were also screened, but in all cases, the desired α-amino acetal 2a was obtained in lower yield (Table 1, entries 5-7).

Other copper catalysts were also screened (Table 1, entries 3, 8-15). CuI catalyzed the reaction sluggishly to afford the desired product 2a and 3a in 35% and 17% yields, respectively (Table 1, entry 13). Other copper salts showed low or even no catalytic activities for this reaction (Table 1, entries 8-12, 14-15). Notably, among the various copper salts investigated, copper(II) was found to exhibit better catalytic activity than copper (I) having the same anion, and the order of the catalytic activity of the anion among copper salts was found to be I>Br>X (Cl, OAc, and so on). We also found that the best volume ratio of methanol to acetonitrile was 1:4, and 40° C. was the most suitable temperature for this reaction by examining the effect of the volume ratio of MeOH/MeCN and temperature on the yield of α-amino acetal 2a (Table 1, entries 5, 16-19). Therefore, our optimal reaction conditions for the rearrangement of tertiary amines were as follows: the reaction was carried out in oxygen atmosphere at 40° C. using 25 mol % of copper(II) bromide and 50 mol % of TMEDA as the catalytic system, the volume ratio of methanol to acetonitrile was 1:4.

Table 1 shows the optimization of the reaction conditions for the reaction scheme shown in FIG. 1(A).

TABLE 1

Optimization of Reaction Conditions of Scheme Shown in FIG. 1(A)

| Entry | Catalyst | Solvent | T [° C.] | t [h] | Yield [%][b] 2a | 3a |
|---|---|---|---|---|---|---|
| 1 | — | MeCN | 40 | 48 | 0 | 0 |
| 2[c] | CuBr₂ | MeCN | 40 | 48 | 11 | 0 |
| 3 | CuBr₂ | MeCN | 40 | 48 | 51 | trace |
| 4[d,f] | CuBr₂ | MeCN | 40 | 6 | 58 | trace |
| 5 | CuBr₂ | MeOH | 40 | 48 | 23 | trace |
| 6 | CuBr₂ | DCE | 40 | 48 | 17 | trace |
| 7 | CuBr₂ | THF | 40 | 48 | trace | 0 |
| 8 | CuCl₂ | MeCN | 40 | 48 | trace | 0 |

TABLE 1-continued

Optimization of Reaction Conditions of Scheme Shown in FIG. 1(A)

| Entry | Catalyst | Solvent | T [° C.] | t [h] | Yield [%][b] 2a | 3a |
|---|---|---|---|---|---|---|
| 9 | Cu(OAc)$_2$ | MeCN | 40 | 48 | 0 | 0 |
| 10 | Cu(OTf)$_2$ | MeCN | 40 | 48 | 0 | 0 |
| 11 | Cu(acac)$_2$ | MeCN | 40 | 48 | 0 | 0 |
| 12 | Cu(MeCN)$_4$PF$_6$ | MeCN | 40 | 48 | trace | 0 |
| 13 | CuI | MeCN | 40 | 96 | 35 | 17 |
| 14 | CuBr | MeCN | 40 | 48 | trace | 0 |
| 15 | CuCl | MeCN | 40 | 48 | 0 | 0 |
| 16[f] | CuBr$_2$ | MeCN | 25 | 96 | 42 | trace |
| 17[f] | CuBr$_2$ | MeCN | 40 | 5 | 66 | trace |
| 18[f] | CuBr$_2$ | MeCN | 60 | 5 | 57 | trace |
| 19[e] | CuBr$_2$ | MeCN | 40 | 5 | 63 | trace |

Reaction conditions: N,N-dicyclohexylbutylamine (0.5 mmol, 1 equiv.), copper catalyst (0.25 equiv.), TMEDA (0.5 equiv.), MeOH (0.2 mL), solvent (2 mL), under O$_2$ atmosphere (1 atm).
[b]Isolated yields based on N,N-dicyclohexyl-n-butylamine.
[c]The reaction was performed without TMEDA, affording the byproduct N,N-dicyclohexylformamide with 62% yield.
[d]The reaction was carried out in air.
[f]The reaction was performed using 0.5 mL methanol.
[e]The reaction was performed using 1 mL methanol.

TABLE 2

Oxidative Rearrangement of Tertiary Amines

| Entry | Substrate R$^1$ | R$^2$ | R$^3$ | Product | t [h] | Yield [%][b] |
|---|---|---|---|---|---|---|
| 1 | Cy | Cy | H | 2a | 5 | 66 |
| 2 | Cy | Cy | Et | 2b | 6 | 65 |
| 3 | Cy | Cy | n-Octyl | 2c | 24 | 61 |
| 4 | Cy | Cy | CO$_2$Me | 2d | 12 | 60 |
| 5 | Cy | Cy | CH$_2$CH$_2$Br | 2e | 6 | 54 |
| 6 | Cy | Cy | CH=CH$_2$ | 2f | 24 | 61 |
| 7 | Cy | Cy | CH$_2$NPhth | 2g | 20 | 56 |
| 8 | Cy | Cy | CH$_2$OAc | 2h | 20 | 55 |
| 9 | Cy | $^i$Pr | H | 2i | 24 | 45 |

Reaction conditions: N,N-dicyclohexylbutylamine (0.5 mmol, 1 equiv.), copper(II) bromide (0.25 equiv.), TMEDA (0.5 equiv.), MeOH (0.5 mL), MeCN (2 mL).
[b]Isolated yields based on N,N-dicyclohexyl-n-butylamine.

Representative examples of tertiary amines for this oxidative rearrangement investigated are shown in Table 2. Almost all the substrates containing $R^1=R^2=Cy$ provided the desired products in good yields under the standard reaction conditions (Table 2, entries 1-8). The tertiary amine with long carbon chain was also suitable for this reaction (Table 2, entry 3) although the reaction time was much longer. The reaction tolerated a wide array of functional groups including ester group (Table 2, entries 4, 8), bromo group (Table 2, entry 5), double bond (Table 2, entry 6), amino group (Table 2, entry 7). It was found that the substrates of $R^1$ and $R^2$ groups with more branched carbon chain (Table 2, entry 1) had better reactivity for this reaction than those with linear carbon chain (Table 2, entry 9).

Figure 3:
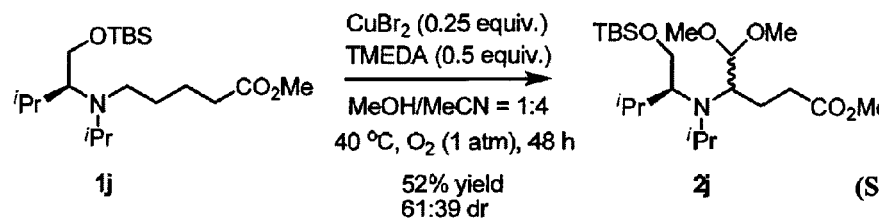
FIG. 3 shows a method for forming methyl 4-(((S)-1-(tert-butyldimethylsilyloxy)-3-methylbutan-2-yl)(isopropyl) amino)-5,5-dimethoxypentanoate (2j) (Scheme 1); a possible mechanism for the method of FIG. 1(A) (Scheme 2); and a method for forming N,N-diisobutyl-1,1-dimethoxyhexan-2-amine (2k) from N,N-diisobutylhex-1-en-1-amine (1k) of Example 1 (Scheme 3).
Figure 3:
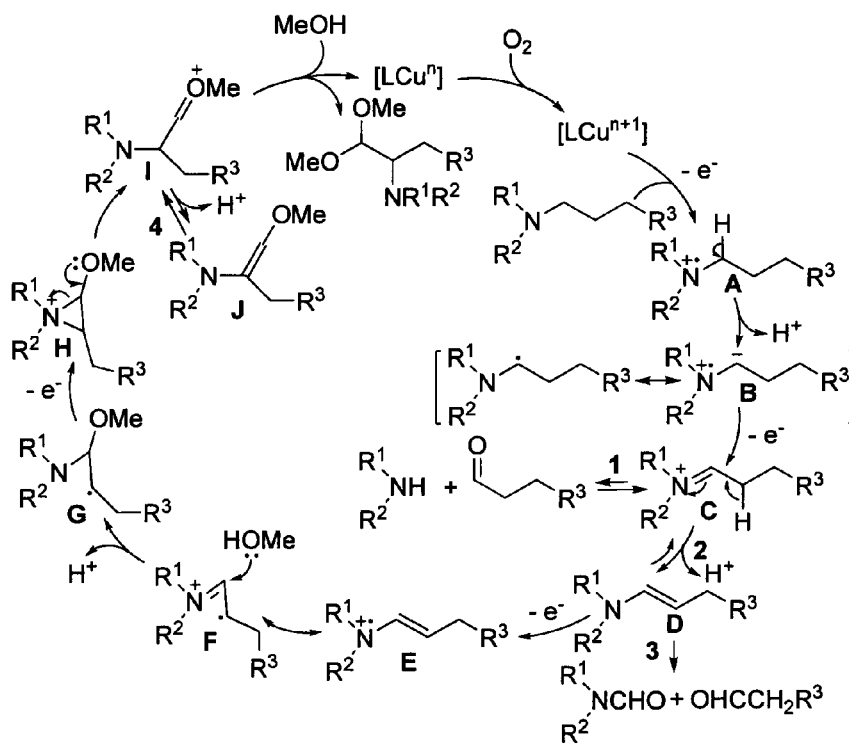
Figure 3:
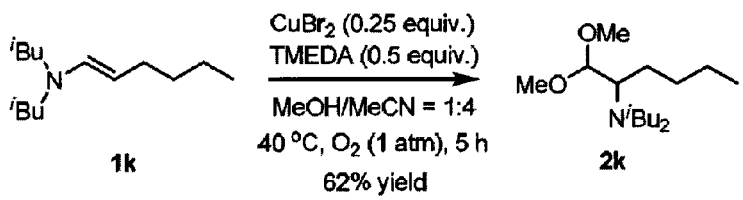

The tertiary amine with a chiral centre was utilized for this reaction, affording the desired product in a moderate yield of 52% with two diastereomers which can be easily separated by silica gel column chromatography (Scheme 1, FIG. 3).

The rearrangement can be rationalized in terms of the proposed mechanism shown in Scheme 2, FIG. 3. Firstly, copper-dioxygen species were thought to function as one-electron oxidizing agents toward tertiary amine, enamine D and intermediates B and G. Initially, copper species [LCu$^{n+1}$] was formed in the catalytic systems of copper salt, molecular oxygen and TMEDA as a bidentate ligand. After electron transfer, deprotonation and electron transfer processes, iminium ion C was produced. Subsequently, iminium ion C was converted into enamine D after deprotonation. Next, electron transfer yielded the cationic radical species E and F. Nucleophilic attack by methanol on the intermediate F and subsequent electron transfer gave the corresponding aziridinium ion H. Upon opening of the three-membered ring to form oxocarbenium ion I, attack by an additional methanol molecule on the oxocarbenium ion I generates the desired product.

Figure 4:
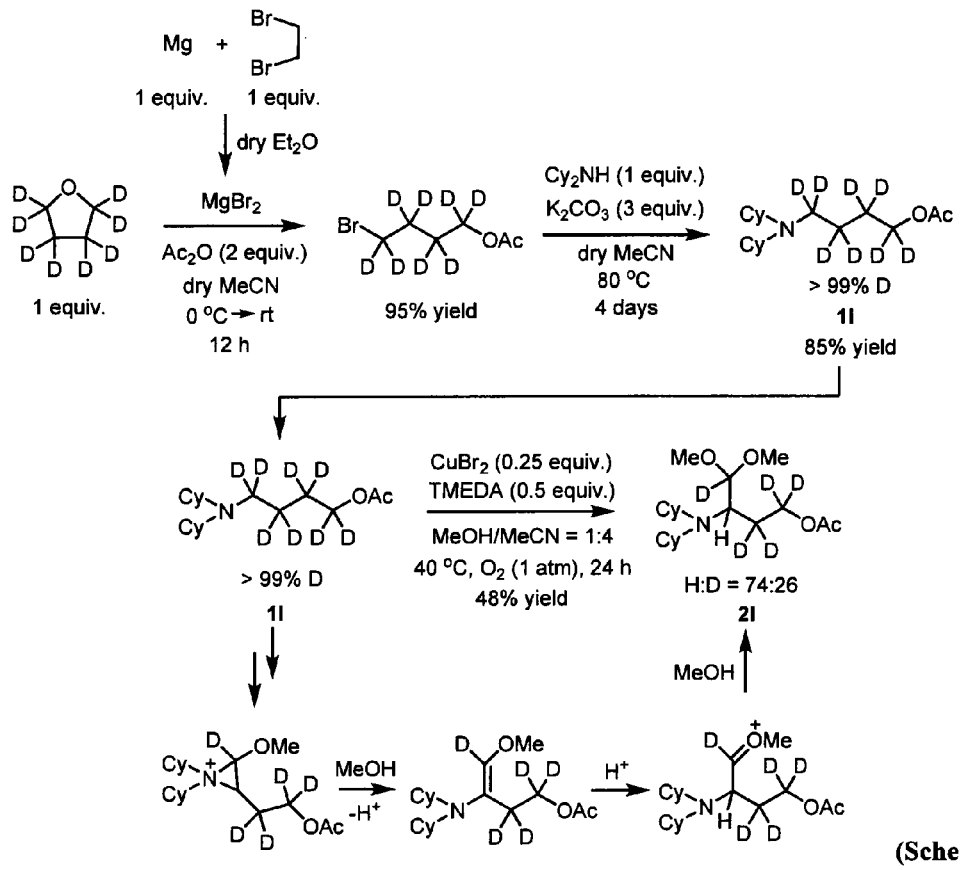
FIG. 4 shows the deuterium labelling experiment of Example 1 and the respective possible mechanism (Schemes 4 and 5).
Figure 4:
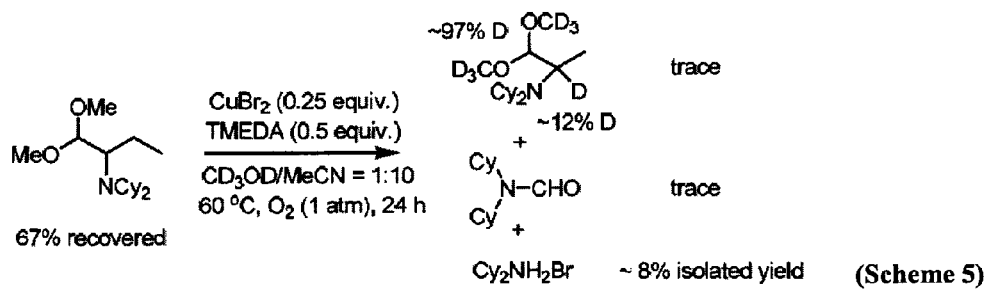

Of mechanistic interests are the followings: (I) the formation of the iminium ion B was proved by the trapping experiment. In the process of carrying out the experiment (Table 1, entries 3, 6-7, 16), it was found that a white solid with the molecular structure Cy$_2$NH$_2$Br (confirmed by X-ray analysis) was isolated from the reaction mixture by a simple filtration with about 8% yield, indicating that the iminium ion B was the reaction intermediate. (II) Enamine is also thought to be the reaction intermediate. In order to prove it, enamine 1k was synthesized for this reaction. Gratifyingly, the desired product 2k was obtained with 62% isolated yield (Scheme 3, FIG. 3). (III) To explore how the rearrangement occurred and which C—H bonds of long carbon chain were activated, substrate 1l for this reaction (Scheme 4, FIG. 4) was synthesized. Interestingly, under the standard reaction conditions, compound 1l gave product 2l in about 48% yield. Especially noteworthy was that 74% hydrogen atom was observed from $^1$H NMR spectrum. This result implied that the product was formed via the below pathway: upon opening of the three-membered ring of aziridinium ion H to form oxocarbenium ion I, attack by an additional methanol molecule on the oxocarbenium ion I generates the desired product. The reason for H/D exchange may be due to deprotonation and protonation of the reversible steps 2 and 4 (Scheme 2, FIG. 3). (IV) When the reaction was performed in the presence of CD$_3$OD using compound 2a as the substrate under the similar reaction conditions, only 67% of 2a was recovered, and the other three byproducts were also produced although the yield was very low (Scheme 5, FIG. 4). This result showed that most of steps in this oxidative rearrangement reaction was reversible, and also explained why these byproducts were produced.

Example 2

Copper-Catalyzed C—H Bond Amination for Direct Synthesis of α-Amino Acetals from Secondary Amines and Aliphatic Aldehydes In this example, a copper-catalyzed C—H bond amination reaction for direct synthesis of α-amino acetals from secondary amines with readily removable protecting groups and aliphatic aldehydes is provided. Furthermore, optically active α-amino acetals were obtained by studying the effect of other chirality elements in the molecule and chiral copper complexes on the reaction. In summary, a copper-catalyzed C—H bond amination reaction for direct synthesis of α-amino acetals from secondary amines with readily removable protecting groups and aliphatic aldehydes was described. Compared with expensive metal catalyst and stoichiometric metal oxidants employed in the traditional methods for C—H bond oxidation, this catalytic system has the obvious advantages of mild reaction conditions and cheap catalysis and oxidant.

General Procedures

All reactions were carried out without exclusion of air or moisture unless otherwise stated. Copper salts, and tert-butyl hydroperoxide (~5.5 M in decane) (TBHP) were purchased from commercial suppliers, and used directly as received. Commercial solvents and reagents were used without further purification. Secondary amines 1(b', j') (C. R. Smith, T. V. RajanBabu, *Org. Lett.*, 2008, 10(8), 1657-1659; S. Mukherjee, B. List, *J. Am. Soc. Chem.*, 2007, 129(37), 11336), enamine 1k' (D. M. Hodgson, C. D. Bray, N. D. Kindon, N. J. Reynolds, S. J. Coote, J. M. Um, and K. N. Houk, *J. Org. Chem.* 2009, 74, 1019-1028), and aliphatic aldehydes 2(f', h') (M. Huckstep, R. J. K. Taylop, *Synthesis* 1982, 881-882; S. Ciblat, J. Kim, C. A. Stewart, J. Z. Wang, P. Forgione, D. Clyne, L. A. Paquette, *Org. Lett.*, 2007, 719) were synthesized. Reactions were monitored through thin layer chromatography [Merck 60 F254 precoated silica gel plate (0.2 mm thickness)]. Subsequent to elution, spots were visualized using UV radiation (254 nm) on Spectroline Model ENF-24061/F 254 nm. Further visualization was possible using basic solution of potassium permanganate or acidic solution of ceric molybdate as stain, followed by heating on a hot plate. Flash chromatography was performed using Merck silica gel 60 with distilled solvents. Infrared spectra were recorded on a Shimadzu IR Prestige-21 FT-IR. Liquid samples were examined as film between NaCl salt plates. HRMS spectra were recorded on a Waters Q-T of Permier Spectrometer. $^1$H NMR and $^{13}$C NMR spectra were recorded using Bruker Avance 300, 400 and 500 MHz spectrometers. Chemical shifts for $^1$H NMR spectra are reported as δ in units of parts per million (ppm) downfield from SiMe$_4$ (δ 0.0) and relative to the signal of chloroform-d (δ 7.260, singlet). Multiplicities were given as: s (singlet); brs (broad singlet); d (doublet); t (triplet); q (quartet); dd (doublets of doublet); ddd (doublets of doublets of doublet); td (triplet of doublet); m (multiplets); ddt (doublet of doublet of triplet) and etc. Coupling constants are reported as a J value in Hz. Carbon nuclear magnetic resonance spectra ($^{13}$C NMR) are reported as δ in units of parts per million (ppm) downfield from SiMe$_4$ (δ 0.0) and relative to the signal of chloroform-d (δ 77.00, triplet).

General Experimental Procedure for Copper-Catalyzed C—H Bond Amination for Direct Synthesis of α-Amino Acetals from Secondary Amines and Aliphatic Aldehydes Typical procedure for copper-catalyzed C—H bond amination for direct synthesis of α-amino acetals from secondary amines and aliphatic aldehydes (dibenzylamine 1a' and butyraldehyde 2a' as a model system) is illustrated in FIG. 1(B): tert-butyl hydroperoxide (~5.5 M in decane) (0.1 mL, ~0.55 mmol) was added to a mixture of CuI (38 mg, 0.2 mmol), dibenzylamine 1a' (98 mg, 0.5 mmol), and butyraldehyde 2a' (54 mg, 0.75 mmol) in methanol (0.4 mL)/acetonitrile (2.0 mL) at room temperature. The mixture was stirred at 40° C. until dibenzylamine 1a' was completely converted by TLC detection. The resulting reaction mixture was mixed with a small amount of silica gel and concentrated. The crude product was purified by flash column chromatography (silica gel; ethyl acetate or diethyl ether/hexane=1:100) to afford the desired product 3a as a light yellowish oil (0.125 g, 80% yield).

N,N-dibenzyl-1,1-dimethoxybutan-2-amine (3a)

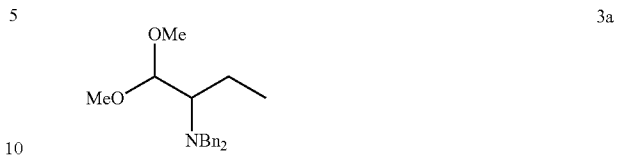

R$_f$=0.70 (hexane:ethyl acetate=3:1); $^1$H NMR (CDCl$_3$, 400 MHz) δ 7.38-7.36 (m, 4H), 7.30-7.26 (m, 4H), 7.22-7.18 (m, 2H), 4.38-4.37 (d, J=5.16 Hz, 1H), 3.82-3.66 (m, 4H), 3.35 (s, 3H), 3.32 (s, 3H), 2.65-2.60 (m, 1H), 1.61-1.44 (m, 2H), 0.94-0.91 (t, J=7.43 Hz, 3H) ppm; $^{13}$C NMR (CDCl$_3$, 100 MHz) δ 140.7 (C×2), 129.0 (CH×4), 128.0 (CH×4), 126.6 (CH$_2$×2), 107.4, 59.4, 54.8, 54.44 (CH$_2$×2), 54.38, 19.5, 12.0 ppm; FTIR (neat): v=3015, 1452, 1215, 754, 700, 494 cm$^{-1}$; HRMS (ESI, m/z): calcd for C$_{20}$H$_{28}$NO$_2^+$ [M+H]$^+$ 314.2120, found: 314.2119.

N,N-dibenzyl-1,1-dimethoxy-3-methylbutan-2-amine (3b)

The product was prepared by above general procedure and the same chemicals except employing dibenzylamine (1a') (98 mg, 0.5 mmol), and 3-methylbutanal (2b') (64 mg, 0.75 mmol). After 24 h, the crude product was purified by flash column chromatography (silica gel; ethyl acetate or diethyl ether/hexane=1:100) to afford the desired product 3b as a light yellowish oil (0.108 g, 66% yield); R$_f$=0.76 (hexane: ethyl acetate=3:1); $^1$H NMR (CDCl$_3$, 400 MHz) δ 7.38-7.36 (m, 4H), 7.30-7.26 (m, 4H), 7.22-7.18 (m, 2H), 4.51-4.50 (d, J=4.28 Hz, 1H), 3.91-3.62 (m, 4H), 3.40 (s, 3H), 3.37 (s, 3H), 2.46-2.43 (m, 1H), 2.05-1.97 (m, 1H), 0.99-0.98 (t, J=6.82 Hz, 3H), 0.84-0.82 (t, J=6.68 Hz, 3H) ppm; $^{13}$C NMR (CDCl$_3$, 100 MHz) δ 140.7 (C×2), 129.2 (CH×4), 128.0 (CH×4), 126.6 (CH×2), 107.1, 62.5, 55.5 (CH$_2$×2), 55.5, 54.8, 27.2, 20.9, 20.7 ppm; FTIR (neat): v=3015, 1215, 754, 700, 494 cm$^{-1}$; HRMS (ESI, m/z): calcd for C$_{21}$H$_{30}$NO$_2^+$ [M+H]$^+$ 328.2277, found: 328.2273.

N,N-dibenzyl-1,1-dimethoxyoctan-2-amine (3c)

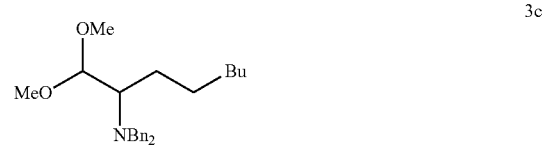

The product was prepared by above general procedure and the same chemicals except employing dibenzylamine (1a') (98 mg, 0.5 mmol), and octanal (2c') (96 mg, 0.75 mmol).

After 24 h, the crude product was purified by flash column chromatography (silica gel; ethyl acetate or diethyl ether/hexane=1:100) to afford the desired product 3c as a light yellowish oil (0.129 g, 70% yield); R$_f$=0.77 (hexane:ethyl acetate=3:1); $^1$H NMR (CDCl$_3$, 400 MHz) δ 7.37-7.35 (m, 4H), 7.30-7.26 (m, 4H), 7.23-7.18 (m, 2H), 4.37-4.36 (d, J=5.03 Hz, 1H), 3.81-3.65 (m, 4H), 3.35 (s, 3H), 3.32 (s, 3H), 2.73-2.68 (m, 1H), 1.59-1.36 (m, 3H), 1.25-1.17 (m, 5H), 1.15-1.08 (m, 2H), 0.88-0.85 (t, J=7.07 Hz, 3H) ppm; $^{13}$C NMR (CDCl$_3$, 100 MHz) δ 140.8 (C×2), 129.0 (CH×4), 128.0 (CH×4), 126.6 (CH$_2$×2), 107.5, 57.4, 54.8, 54.5 (CH$_2$×2), 54.3, 31.9, 29.4, 26.9, 26.5, 22.7, 14.1 ppm; FTIR (neat): v=3015, 1215, 754, 700, 494 cm$^{-1}$; HRMS (ESI, m/z): calcd for C$_{24}$H$_{36}$NO$_2{}^+$ [M+H]$^+$ 370.2746, found: 370.2743.

N,N-dibenzyl-1,1-dimethoxypent-4-en-2-amine (3d)

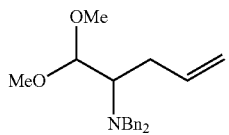

3d

The product was prepared by above general procedure and the same chemicals except employing dibenzylamine (1a') (98 mg, 0.5 mmol), and pent-4-enal (2d') (63 mg, 0.75 mmol). After 24 h, the crude product was purified by flash column chromatography (silica gel; ethyl acetate or diethyl ether/hexane=1:100) to afford the desired product 3d as a light yellowish oil (0.102 g, 63% yield); R$_f$=0.70 (hexane:ethyl acetate=3:1); $^1$H NMR (CDCl$_3$, 400 MHz) δ 7.38-7.37 (m, 4H), 7.30-7.26 (m, 4H), 7.21-7.18 (m, 2H), 5.89-5.79 (m, 1H), 5.08-5.00 (m, 2H), 4.39-4.38 (d, J=4.93 Hz, 1H), 3.80-3.71 (m, 4H), 3.35 (s, 3H), 3.28 (s, 3H), 2.89-2.84 (m, 1H), 2.44-2.26 (m, 2H) ppm; C NMR (CDCl$_3$, 100 MHz) δ 140.5 (C×2), 137.8, 129.0 (CH×4), 128.0 (CH×4), 126.7 (CH$_2$×2), 115.5, 107.0, 57.8, 54.7, 54.5, 54.4 (CH$_2$×2), 31.2 ppm; FTIR (neat): v=3015, 1454, 1215, 754, 700, 494 cm$^{-1}$; HRMS (ESI, m/z): calcd for C$_{21}$H$_{28}$NO$_2{}^+$ [M+H]$^+$ 326.2120, found: 326.2114.

(Z)—N,N-dibenzyl-1,1-dimethoxyhept-4-en-2-amine (3e)

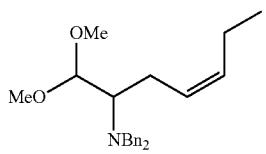

3e

The product was prepared by above general procedure and the same chemicals except employing dibenzylamine (1a') (98 mg, 0.5 mmol), and (Z)-hept-4-enal (2e') (84 mg, 0.75 mmol). After 48 h, the crude product was purified by flash column chromatography (silica gel; ethyl acetate or diethyl ether/hexane=1:100) to afford the desired product 3e as a light yellowish oil (0.115 g, 65% yield); R$_f$=0.72 (hexane:ethyl acetate=3:1); $^1$H NMR (CDCl$_3$, 400 MHz) δ 7.38-7.36 (m, 4H), 7.30-7.26 (m, 4H), 7.24-7.18 (m, 2H), 5.44-5.36 (m, 2H), 4.38-4.37 (d, J=4.73 Hz, 1H), 3.79-3.71 (m, 4H), 3.36 (s, 3H), 3.28 (s, 3H), 2.86-2.81 (m, 1H), 2.44-2.37 (m, 1H), 2.28-2.20 (m, 1H), 2.08-2.01 (m, 2H), 0.95-0.91 (t, J=7.53 Hz, 3H) ppm; $^{13}$C NMR (CDCl$_3$, 100 MHz) δ 140.6 (C×2), 131.9, 129.0 (CH×4), 128.0 (CH×4), 127.6, 126.7 (CH$_2$×2), 107.3, 58.0, 54.8, 54.6, 54.5 (CH$_2$×2), 24.2, 20.7, 14.2 ppm; FTIR (neat): v=3017, 1454, 1215, 1072, 756, 699, 498 cm$^{-1}$; HRMS (ESI, m/z): calcd for C$_{23}$H$_{32}$NO$_2{}^+$ [M+H]$^+$ 354.2433, found: 354.2443.

N,N-dibenzyl-5-(tert-butyldiphenylsilyloxy)-1,1-dimethoxypentan-2-amine (3l)

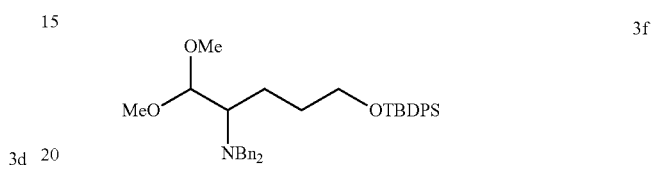

3f

The product was prepared by above general procedure and the same chemicals except employing dibenzylamine (1a') (98 mg, 0.5 mmol), and 5-(tert-butyldiphenylsilyloxy)pentanal (2f') (0.255 g, 0.75 mmol). After 48 h, the crude product was purified by flash column chromatography (silica gel; ethyl acetate or diethyl ether/hexane=1:100) to afford the desired product 3f as a light yellowish oil (0.230 g, 79% yield); R$_f$=0.72 (hexane:ethyl acetate=3:1); $^1$H NMR (CDCl$_3$, 400 MHz) δ 7.66-7.64 (m, 4H), 7.43-7.33 (m, 10H), 7.28-7.17 (m, 6H), 4.38-4.37 (d, J=5.42 Hz, 1H), 3.79-3.66 (m, 4H), 3.61-3.45 (m, 2H), 3.33 (s, 3H), 3.32 (s, 3H), 2.73-2.68 (m, 1H), 1.86-1.76 (m, 1H), 1.68-1.40 (m, 3H), 1.04 (s, 9H) ppm; $^{13}$C NMR (CDCl$_3$, 100 MHz) δ 140.6 (C×2), 135.6 (CH×4), 134.2 (C×2), 129.4 (CH$_2$×2), 129.1 (CH×4), 128.0 (CH×4), 127.5 (CH×4), 126.7 (CH$_2$×2), 107.4, 63.9, 57.4, 54.7, 54.5 (CH$_2$×2), 54.2, 30.3, 26.9 (CH$_3$×3), 22.8, 19.2 ppm; FTIR (neat): v=3017, 1215, 1111, 758, 494 cm$^{-1}$; HRMS (ESI, m/z): calcd for C$_{37}$H$_{48}$NO$_3$Si$^+$ [M+H]$^+$ 582.3403, found: 582.3401.

N,N-dibenzyl-1,1-dimethoxy-3-phenylpropan-2-amine (3g)

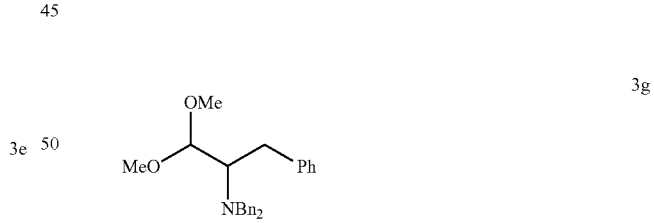

3g

The product was prepared by above general procedure and the same chemicals except employing dibenzylamine (1a') (98 mg, 0.5 mmol), and 3-phenylpropanal (2g') (0.100 g, 0.75 mmol). After 48 h, the crude product was purified by flash column chromatography (silica gel; ethyl acetate or diethyl ether/hexane=1:100) to afford the desired product 3g as a light yellowish oil (0.129 mg, 69% yield); R$_f$=0.72 (hexane:ethyl acetate=3:1); $^1$H NMR (CDCl$_3$, 400 MHz) δ 7.27-7.01 (m, 15H), 4.42-4.41 (d, J=4.38 Hz, 1H), 3.74 (s, 4H), 3.37 (s, 3H), 3.30 (s, 3H), 3.13-3.08 (m, 1H), 2.88-2.86 (m, 2H) ppm; $^{13}$C NMR (CDCl$_3$, 100 MHz) δ 140.8, 140.3 (C×2), 129.6 (CH$_2$×2), 128.7 (CH×4), 128.0 (CH×6), 126.5 (CH$_2$×2), 125.3, 107.2, 59.6, 54.9, 54.8, 54.4 (CH$_2$×2), 32.6 ppm; FTIR methyl 4-(dibenzylamino)-5,5-dimethoxypentanoate (3h)

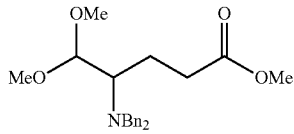

The product was prepared by above general procedure and the same chemicals except employing dibenzylamine (1a') (98 mg, 0.5 mmol), and methyl 5-oxopentanoate (2h') (97 mg, 0.75 mmol). After 48 h, the crude product was purified by flash column chromatography (silica gel; ethyl acetate or diethyl ether/hexane=1:100) to afford the desired product 3h as a light yellowish oil (0.124g, 67% yield); $R_f$=0.54 (hexane: ethyl acetate=3:1); $^1$H NMR (CDCl$_3$, 400 MHz) δ 7.33-7.27 (m, 8H), 7.25-7.19 (m, 2H), 4.44-4.42 (d, J=5.53 Hz, 1H), 3.82-3.63 (m, 4H), 3.55 (s, 3H), 3.363-3.359 (m, 6H), 2.78-2.73 (m, 1H), 2.53-2.26 (m, 2H), 1.86-1.70 (m, 2H) ppm; $^{13}$C NMR (CDCl$_3$, 100 MHz) δ 174.2, 140.2 (C×2), 129.1 (CH× 4), 128.1 (CH×4), 126.8 (CH$_2$×2), 106.7, 56.6, 54.8, 54.2 (CH$_2$×2), 53.6, 51.3, 31.1, 21.9 ppm; FTIR (neat): v=3017, 1454, 1215, 758, 494 cm$^{-1}$; HRMS (ESI, m/z): calcd for C$_{22}$H$_{30}$NO$_4^+$ [M+H]$^+$ 372.2175, found: 372.2178.

N-allyl-N-benzyl-1,1-dimethoxybutan-2-amine (3i)

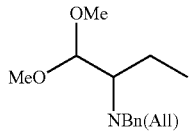

The product was prepared by above general procedure and the same chemicals except employing N-benzylprop-2-en-1-amine (1b') (74 mg, 0.5 mmol), and butyraldehyde (2a') (55 mg, 0.75 mmol). After 24 h, the crude product was purified by flash column chromatography (silica gel; ethyl acetate or diethyl ether/hexane=1:100) to afford the desired product 3l as a light yellowish oil (92 mg, 69% yield); $R_f$=0.72 (hexane: ethyl acetate=3:1); $^1$H NMR (CDCl$_3$, 400 MHz) δ 7.36-7.34 (m, 2H), 7.30-7.26 (m, 2H), 7.24-7.18 (m, 1H), 5.85-5.75 (m, 1H), 5.17-5.03 (m, 2H), 4.32-4.31 (d, J=5.35 Hz, (m, 2H), 0.97-0.94 (t, J=7.41 Hz, 3H) ppm; $^{13}$C NMR (CDCl$_3$, 100 MHz) δ 141.1, 138.1, 128.7 (CH$_2$×2), 128.0 (CH$_2$×2), 126.5, 116.1, 107.3, 60.4, 54.7, 54.5, 54.4, 53.5, 19.7, 12.0 ppm; FTIR (neat): v=3017, 1452, 1215, 1065, 756, 494 cm$^{-1}$; HRMS (ESI, m/z): calcd for C$_{16}$H$_{26}$NO$_2^+$ [M+H]$^+$ 264.1964, found: 264.1965.

N-benzyl-1,1-diethoxy-N—((R)-1-phenylethyl)butan-2-amine (3j)

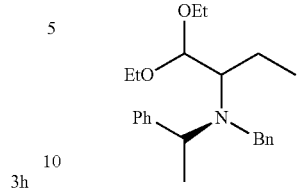

$R_f$=0.71 (hexane:ethyl acetate=3:1); $^1$H NMR (400 MHz, CDCl$_3$): δ 7.36-7.34 (m, 4H), 7.30-7.24 (m, 4H), 7.21-7.17 (m, 2H), 4.48-4.47 (d, J=4.20 Hz, 1H), 4.11-4.05 (q, J=6.86, 13.74 Hz, 1H), 3.99-3.80 (m, 2H), 3.75-3.67 (m, 1H), 3.63-3.55 (m, 1H), 3.48-3.35 (m, 2H), 2.75-2.70 (m, 1H), 1.56-1.46 (m, 1H), 1.39-1.31 (m, 4H), 1.23-1.19 (t, J=7.02 Hz, 3H), 1.15-1.12 (t, J=7.04 Hz, 3H), 0.77-0.73 (t, J=7.43 Hz, 3H); $^{13}$C NMR (100 MHz, CDCl$_3$): δ 145.9, 142.5, 128.8 (CH$_2$×2), 127.90 (CH$_2$×2), 127.89 (CH$_2$×2), 127.87 (CH$_2$× 2), 126.5, 126.3, 106.7, 63.4, 63.3, 60.2, 57.6, 50.9, 19.6, 18.7, 15.5, 15.2, 12.4 ppm.

N,N-diallyl-1,1-dimethoxyhexan-2-amine (3k)

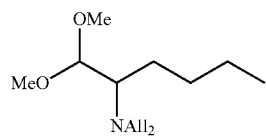

N,N-diallylhex-1-en-1-amine 1k' (90 mg, 0.5 mmol) was added to a mixture of CuBr$_2$ (28 mg, 0.125 mmol), and TMEDA (29 mg, 0.25 mmol) in methanol (0.5 mL)/acetonitrile (2.0 mL) in air at room temperature. The mixture was stirred at 40° C. using O$_2$ balloon for 2 hours. The resulting reaction mixture was mixed with a small amount of silica gel and concentrated. The crude product was purified by flash column chromatography (silica gel; ethyl acetate or diethyl ether/hexane=1:100) to afford the desired product 3k as a light yellowish oil (85 mg, 70% yield); $R_f$=0.70 (hexane:ethyl acetate=3:1); $^1$H NMR (CDCl$_3$, 400 MHz) δ 5.83-5.73 (m, 2H), 5.16-5.03 (m, 4H), 4.24-4.23 (d, J=5.14 Hz, 1H), 3.362-3.359 (m, 6H), 3.29-3.12 (m, 4H), 2.80-2.76 (m, 1H), 1.47-1.36 (m, 3H), 1.35-1.23 (m, 3H), 0.90-0.87 (t, J=7.16 Hz, 3H) ppm; C NMR (CDCl$_3$, 100 MHz) δ 138.2 (CH$_2$×2), 115.8 (CH$_2$×2), 107.3, 59.1, 54.8, 54.6, 53.5 (CH$_2$×2), 29.4, 26.3, 22.8, 14.1 ppm; FTIR (neat): v=2955, 1468, 1215, 1070, 756, 699, 496 cm$^{-1}$.

Deuterium Labelling Experiment

N,N-dibenzyl-1,1-dimethoxy-D6-butan-D1-2-amine (3l)

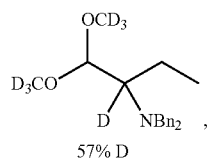

57% D $R_f$=0.70 (hexane:ethyl acetate=3:1); $^1$H NMR (CDCl$_3$, 400 MHz) δ 7.38-7.36 (m, 4H), 7.30-7.26 (m, 4H), 7.23-7.18 (m, 2H), 4.38-4.37 (m, 1H), 3.82-3.66 (m, 4H), 2.64-2.60 (m, 0.43H), 1.59-1.44 (m, 2H), 0.94-0.91 (t, J=7.43 Hz, 3H) ppm; $^{13}$C NMR (CDCl$_3$, 100 MHz) δ 140.7 (C×2), 129.0 (CH×4), 128.0 (CH×4), 126.6 (CH$_2$×2), 107.2, 59.4, 54.5 (CH$_2$×2), 19.54, 19.43, 12.03, 11.99 ppm; FTIR (neat): v=3015, 1215, 754, 700, 494 cm$^{-1}$; HRMS (ESI, m/z): calcd for C$_{20}$H$_{33}$D$_5$NO$_4^+$ [M+H]$^+$ 361.3115, found: 361.3109.

Results and Discussion

In the initial study for the optimization of the reaction conditions about the C—H bond amination reaction to directly synthesize α-amino acetals, dibenzylamine, butyraldehyde, and methanol were selected as the model reaction system. The results are summarized in Table 3. When we subjected dibenzylamine 1a' to copper(I) iodide and oxygen in methanol/acetonitrile at 40° C., no product 3a was observed (Table 3, entry 2). Interestingly, most of the substrate 1a' was converted into the desired product 3a with 80% isolated yield when tert-butyl hydroperoxide (~5.5 M in decane) was used as the oxidant (Table 3, entry 3). It was important to note that the reaction did not proceed without copper catalyst (Table 3, entry 1). Other peroxides such as di-tert-butyl peroxide, tert-butyl benzoylperoxide were also investigated, generating the desired product 2a' with not more than 50% isolated yield (Table 3, entries 4-5). It is noteworthy that the reaction proceeded even at room temperature without a significant decrease in yield (Compare Table 3, entry 3 with Table 3, entry 6).

TABLE 3

Optimization of Reaction Conditions of Scheme Shown in FIG. 1(B)

| Entry | Catalyst | Oxidant | Solvent | T [° C.] | t [h] | Yield [%][b] |
|---|---|---|---|---|---|---|
| 1 | — | $^t$BuOOH | MeCN | 40 | 24 | 0 |
| 2 | CuI | O$_2$ or air (1 atm) | MeCN | 40 | 24 | 0 |
| 3 | CuI | $^t$BuOOH | MeCN | 40 | 24 | 80 |
| 4 | CuI | $^t$BuOO$^t$Bu | MeCN | 40 | 24 | trace |
| 5 | CuI | $^t$BuOOBz | MeCN | 40 | 24 | 50 |
| 6 | CuI | $^t$BuOOH | MeCN | 20 | 96 | 75 |
| 7$^c$ | CuI | $^t$BuOOH | MeCN | 40 | 72 | 57 |
| 8$^d$ | CuI | $^t$BuOOH | MeCN | 40 | 24 | 50 |
| 9 | CuI | $^t$BuOOH | MeOH | 40 | 24 | 50 |
| 10 | CuI | $^t$BuOOH | DCE | 40 | 24 | 48 |
| 11 | CuI | $^t$BuOOH | THF | 40 | 24 | 53 |
| 12 | CuI | $^t$BuOOH | DMSO | 40 | 24 | 51 |
| 13 | CuBr | $^t$BuOOH | MeCN | 40 | 24 | 55 |
| 14 | CuCl | $^t$BuOOH | MeCN | 40 | 24 | 14 |
| 15 | CuBr$_2$ | $^t$BuOOH | MeCN | 40 | 24 | 67 |
| 16 | CuCl$_2$ | $^t$BuOOH | MeCN | 25 | 24 | 9 |
| 17 | Cu(OAc)$_2$ | $^t$BuOOH | MeCN | 40 | 24 | 0 |
| 18 | Cu(OTf)$_2$ | $^t$BuOOH | MeCN | 40 | 24 | trace |

Reaction conditions: Dibenzylamine (0.5 mmol, 1 equiv.), butyraldehyde (0.75 mmol), copper catalyst (0.4 equiv.), oxidant (1.1 equiv.), methanol (0.4 mL), solvent (2 mL).
[b]Isolated yields based on dibenzylamine.
$^c$The reaction was performed using 0.2 equiv. CuI.
$^d$The reaction was performed using 0.2 mL MeOH.

When the amount of copper (I) iodide was reduced from 0.4 equiv to 0.2 equiv (Table 3, entries 3, 7), CuI sluggishly catalyzed the reaction to afford the desired product in 57% yield although it took longer time (72 h) for the reaction (Table 3, entry 7). It was also found that the best volume ratio of methanol to acetonitrile was 1:5, and 40° C. was the most suitable temperature for this reaction by examining the effect of the volume ratio of MeOH/MeCN and temperature on the yield of α-amino acetal 3a (Table 3, entries 3, 6, 8). Among the various solvents screened, acetonitrile emerged as the best solvent for this reaction, generating the desired product in 80% isolated yield (Table 3, entry 3). Other solvents such as methanol, 1,2-dichloroethane (DCE), tetrahydrofuran (THF), and dimethyl sulfoxide (DMSO) were also studied, but in all cases, the desired α-amino acetal 3a was obtained in about 50% isolated yield (Table 3, entries 9-12). Other copper catalysts were also examined (Table 1, entries 13-18). CuBr and CuBr$_2$ also can catalyze the reaction to afford the desired product 3a in moderate yield under the same conditions (Table 3, entries 13, 15). Other copper salts such as CuCl, CuCl$_2$, Cu(OAc)$_2$, and Cu(OTf)$_2$ showed low or even no catalytic activities for this reaction (Table 3, entries 14, 16-18). Therefore, the optimal reaction conditions for C—H bond amination reaction to directly synthesize α-amino acetals were as follows: the reaction was carried out at 40° C. using 40 mol % of copper (I) iodide as the catalysis, tert-butyl hydroperoxide (~5.5 M in decane) was used as the oxidant, and the volume ratio of methanol to acetonitrile was 1:5.

TABLE 4

Oxidative Rearrangement of Secondary Amines and Aliphatic Aldehydes via C—H Bond Amination Entry Product Yield (%)$^a$ Time (h)

1

MeO—CH(OMe)—CH(NBn$_2$)—CH$_2$CH$_3$

80%, 24 h, 3a

2

MeO—CH(OMe)—CH(NBn$_2$)—CH(CH$_3$)$_2$

66%, 24 h, 3b

3

MeO—CH(OMe)—CH(NBn$_2$)—CH$_2$CH$_2$—Bu

70%, 24 h, 3c

4

MeO—CH(OMe)—CH(NBn$_2$)—CH$_2$CH=CH$_2$

63%, 24 h, 3d

5

MeO—CH(OMe)—CH(NBn$_2$)—CH$_2$CH=CHCH$_3$

65%, 48 h, 3e

TABLE 4-continued

Oxidative Rearrangement of Secondary Amines and Aliphatic Aldehydes via C—H Bond Amination

| Entry | Product | Yield (%)[a] Time (h) |
|---|---|---|
| 6 | MeO, OMe, NBn$_2$, OTBDPS | 79%, 48 h, 3f |
| 7 | MeO, OMe, NBn$_2$, Ph | 69%, 48 h, 3g |
| 8 | MeO, OMe, NBn$_2$, O, OMe | 67%, 48 h, 3h |
| 9 | MeO, OMe, NBn(All) | 69%, 24 h, 3i |

Reaction conditions: secondary amine (0.5 mmol), aliphatic aldehyde (0.75 mmol), copper (I) iodide (0.4 equiv.), tert-butyl hydroperoxide (~5.5 M in decane) (~1.1 equiv.), methanol (0.4 mL), MeCN (2 mL).
[b]Isolated yields based on secondary amine.

Representative examples of aliphatic aldehydes for this C—H bond amination reaction investigated are shown in Table 4. Almost all the substrates containing different functional groups provided the desired products in good yields under the standard reaction conditions (Table 4, entries 1-8). The aliphatic aldehydes with long carbon chain or more branched carbon chain were also suitable for this reaction (Table 4, entries 2-3) although the yield slightly decreased under the same reaction conditions (Compare Table 2, entries 2-3 with Table 2, entry 1). The reaction also can tolerate a wide array of functional groups including double bond (Table 4, entries 4-5), tert-butyl diphenylsilyl (TBDPS) group (Table 4, entry 6), phenyl group (Table 4, entry 7), ester group (Table 4, entry 8). For the scope of the secondary amines, some secondary amines with readily removable protecting groups such as an allyl or a benzyl group were chosen for this C—H bond amination reaction. As shown in Table 4, entries 1, 9, this type of substrates were also suitable for this reaction with good yields.

Figure 5:
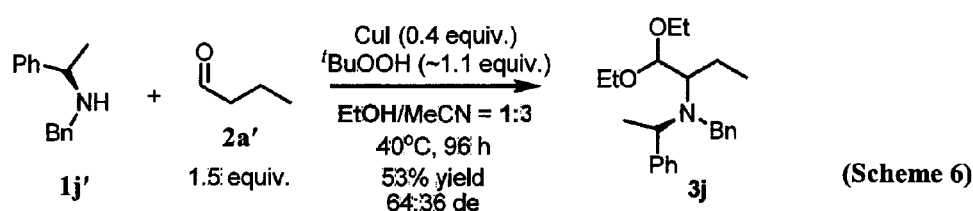
FIG. 5 shows a chiral secondary amine for C—H bond amination reaction of Example 2 (Scheme 6) and a method for forming N,N-diallyl-1,1-dimethoxyhexan-2-amine (3k) from N,N-diallylhex-1-en-1-amine (1k') of Example 2 (Scheme 7).
Figure 5:
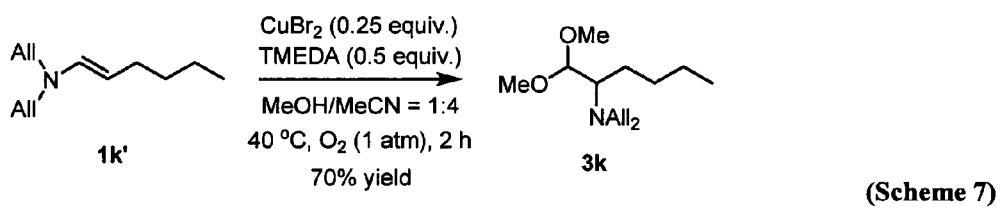

For enantioselective synthesis of α-amino acetals, two strategies were adopted for it. Firstly, the effect of other chirality elements in the molecule including chiral amino protection groups, chiral aliphatic aldehydes, and chiral alcohols was examined for this C—H bond amination reaction. For example, the secondary amine with a chiral centre was utilized for this reaction, affording the desired product in a moderate yield of 53% with two diastereomers which can be easily separated by silica gel column chromatography (Scheme 6, FIG. 5). Another strategy is that chiral metal complexes were used for the catalytic enantioselective C—H amination reaction, affording the desired product with good yields and enantioselectivity.

Enamine is also thought to be the reaction intermediate. On the basis of this, a series of enamines were developed for copper-catalyzed oxidative rearrangement for direct synthesis of α-amino acetals in air or oxygen. For example, enamine 1k' was synthesized for this reaction. The desired product 3k was obtained with 70% isolated yield (Scheme 7, FIG. 5).

Figure 6:
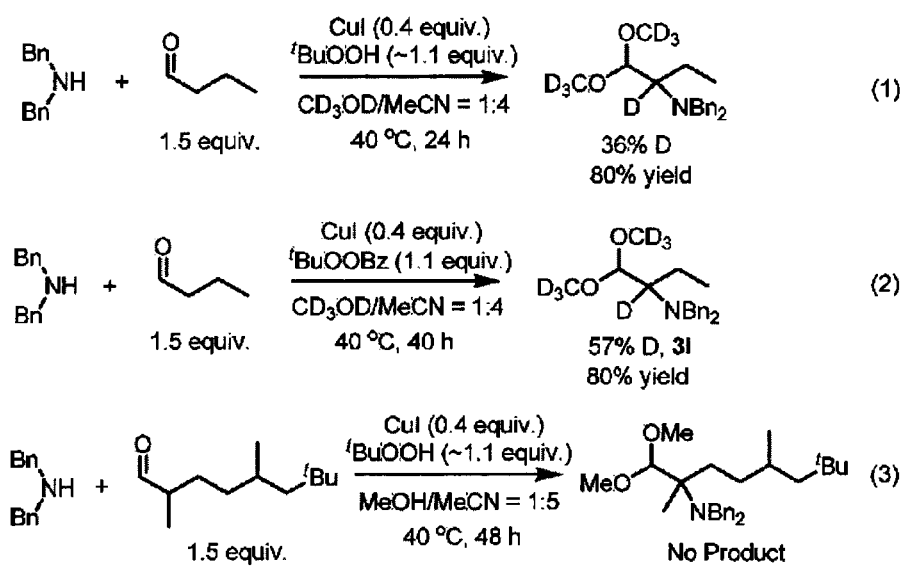
FIG. 6 shows the deuterated labeling experiment of Example 2 (Scheme 8).
Figure 7A:
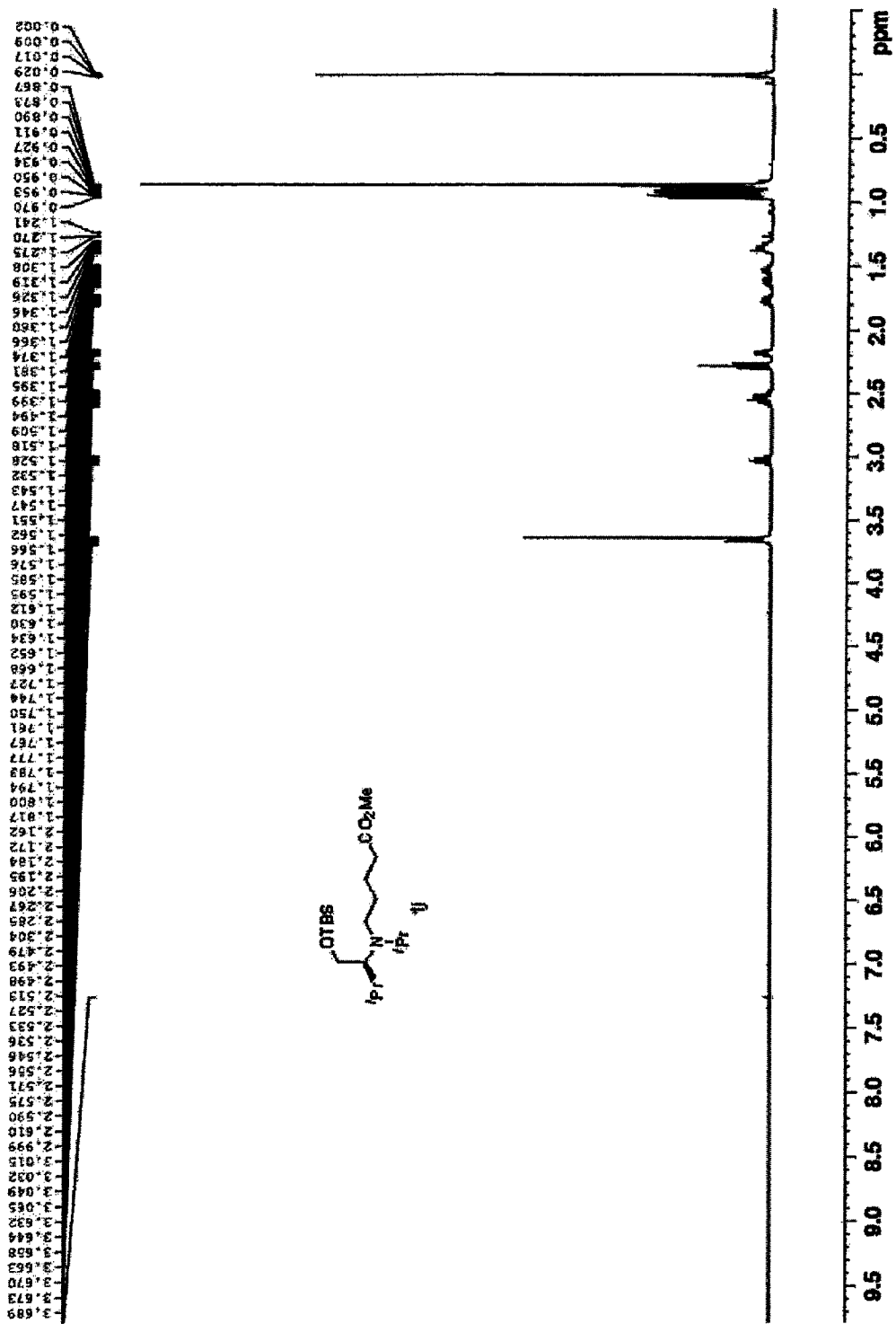
FIGS. 7(A) and (B) show, respectively, the $^1$H NMR and $^{13}$C NMR spectra of (S)-methyl 5-((1-(tert-butyldimethylsilyloxy)-3-methylbutan-2-yl)(isopropyl)amino)pentanoate (1j) of Example 1.
Figure 7B:
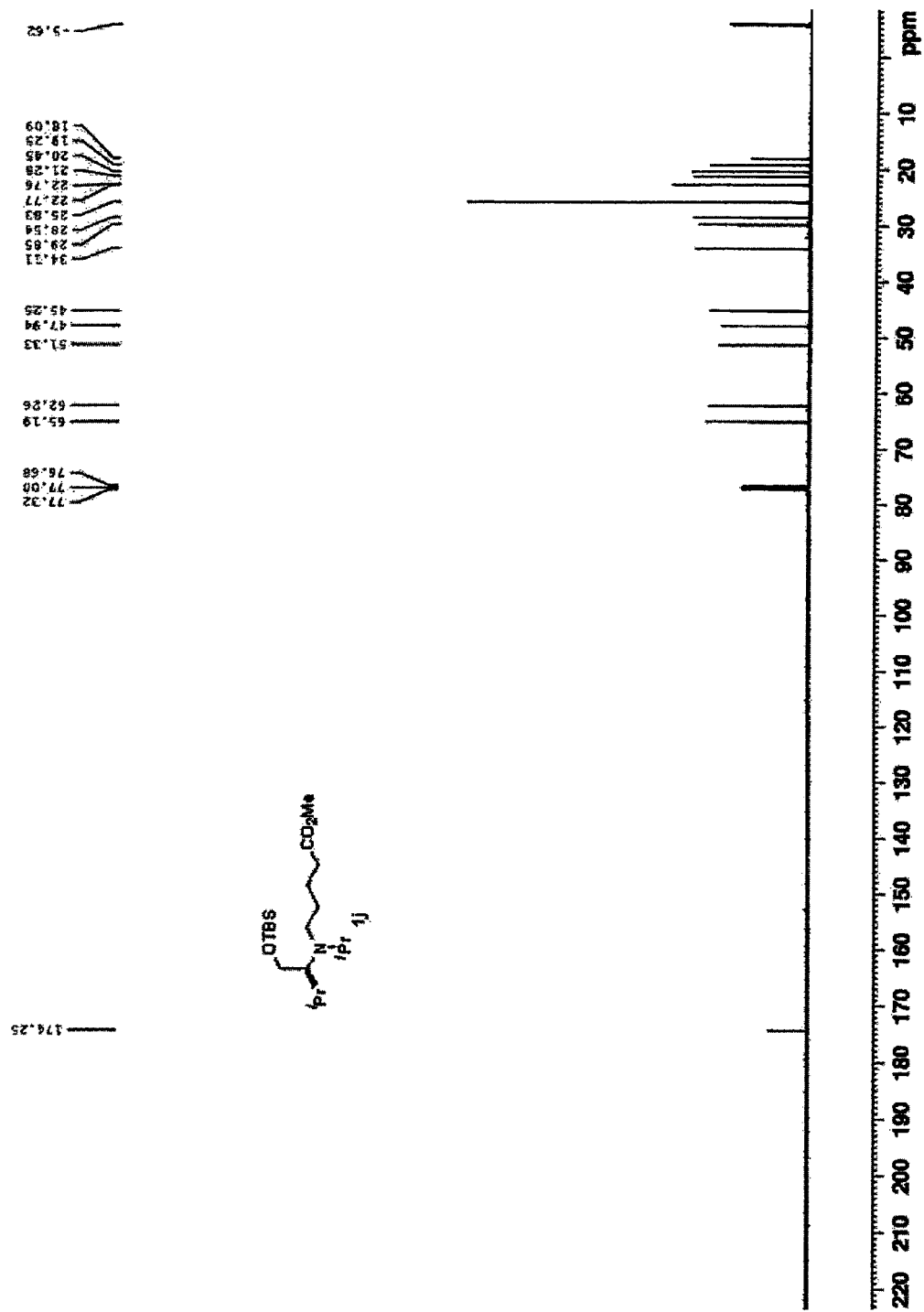
Figure 8A:
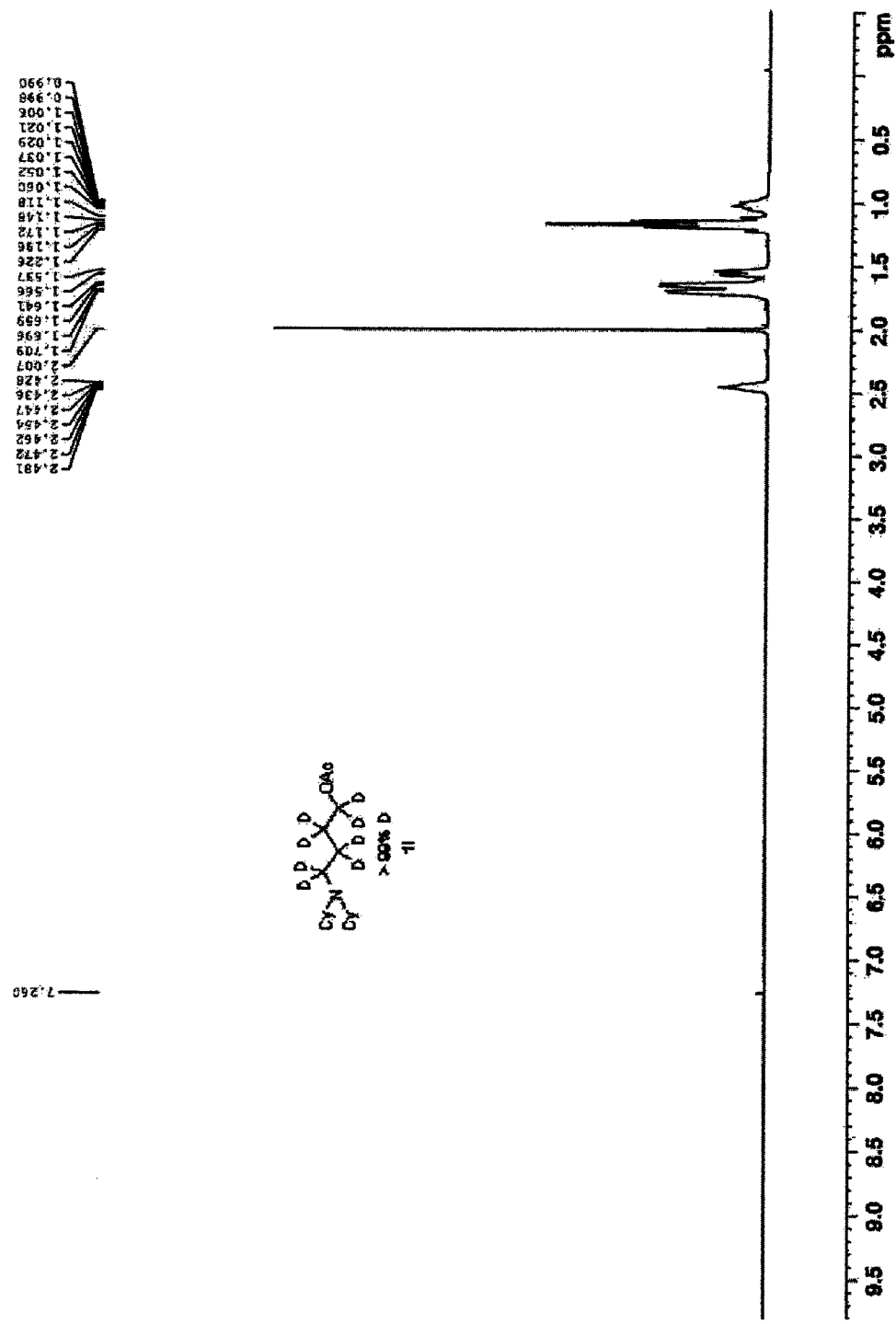
FIGS. 8(A) and (B) show, respectively, the $^1$H NMR and $^{13}$C NMR spectra of 4-(dicyclohexylamino)butyl-D8 acetate (1l) of Example 1.
Figure 8B:
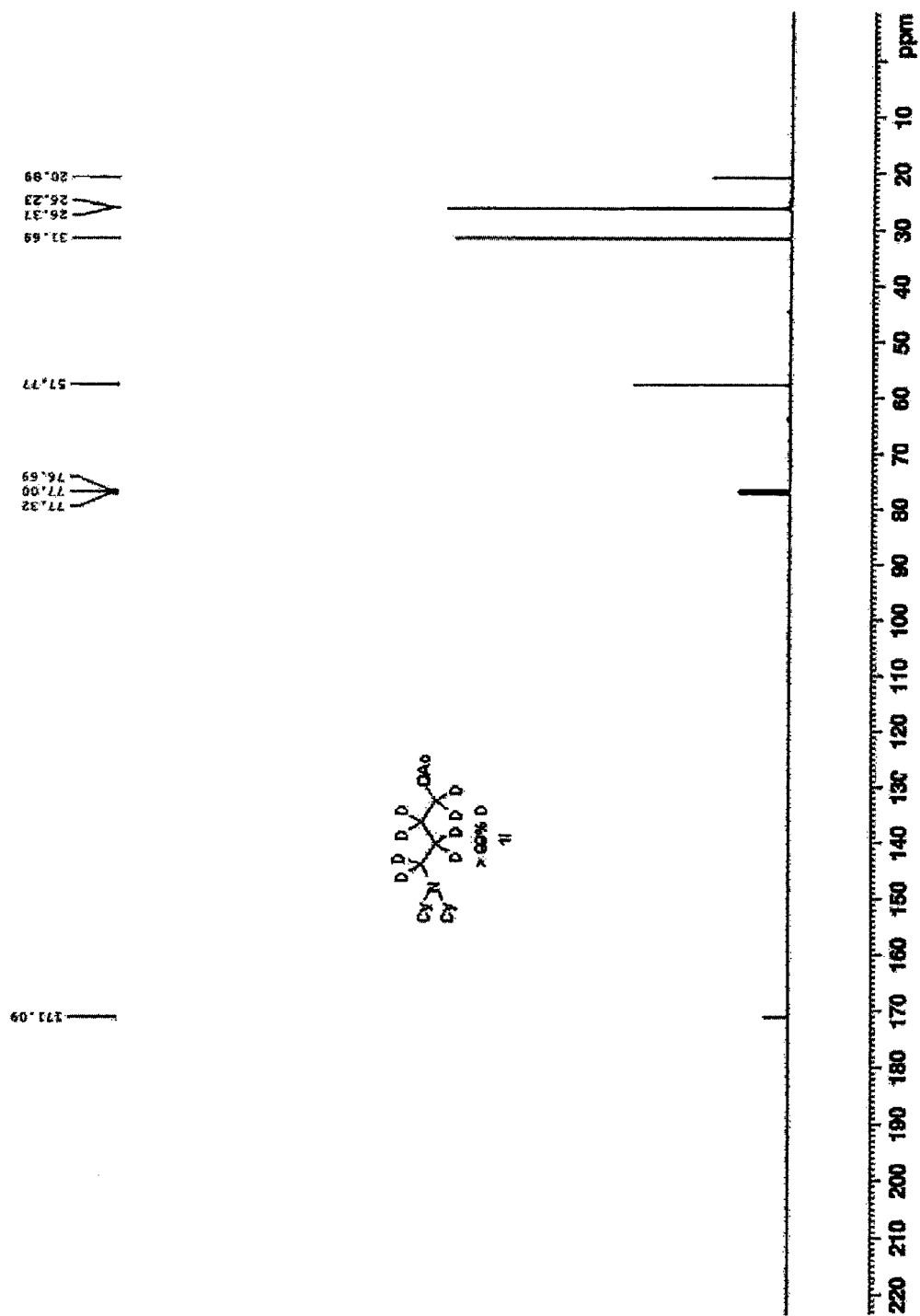
Figure 9A:
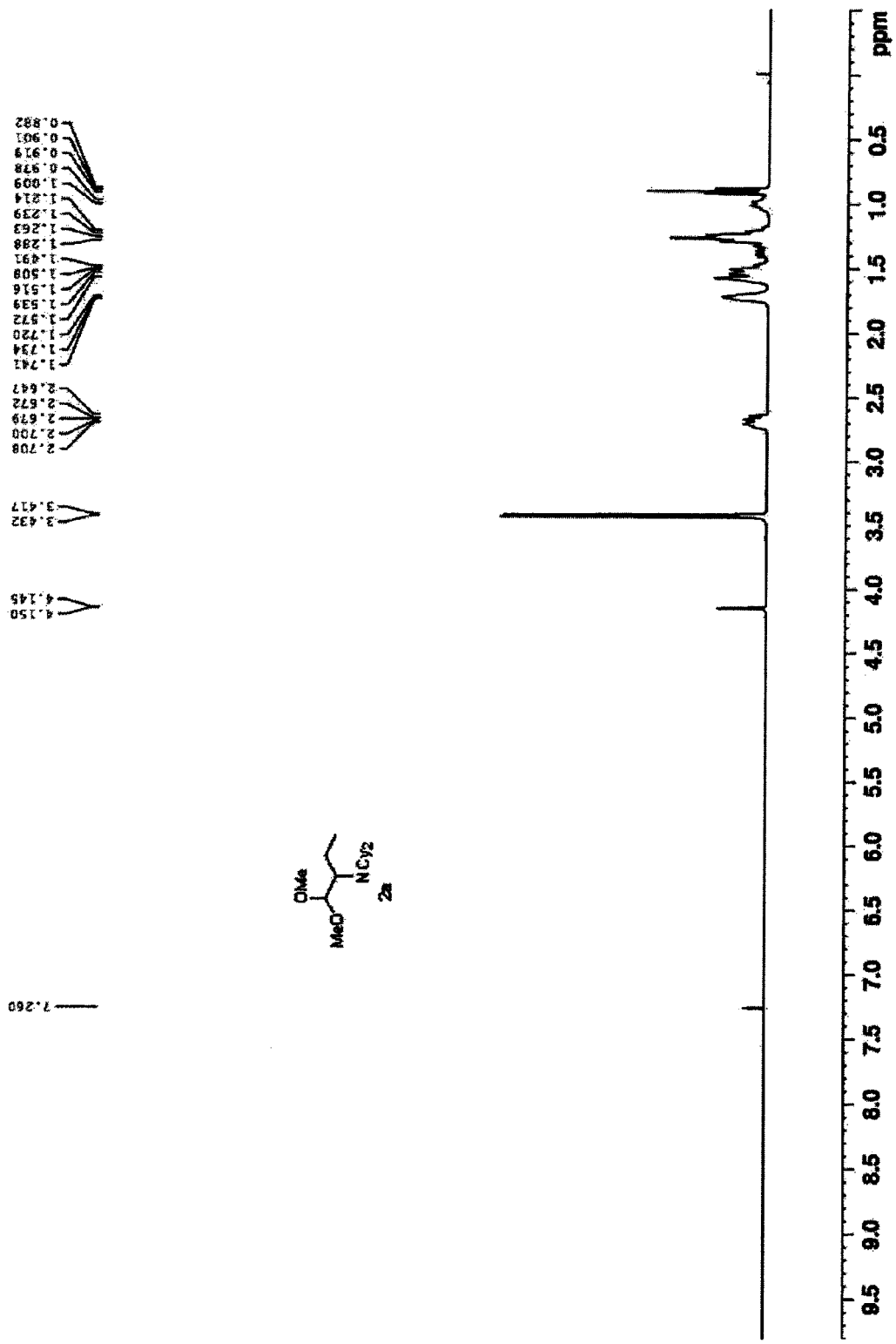
FIGS. 9(A) and (B) show, respectively, the $^1$H NMR and $^{13}$C NMR spectra of N-cyclohexyl-N-(1,1-dimethoxybutan-2-yl)cyclohexanamine (2a) of Example 1.
Figure 9B:
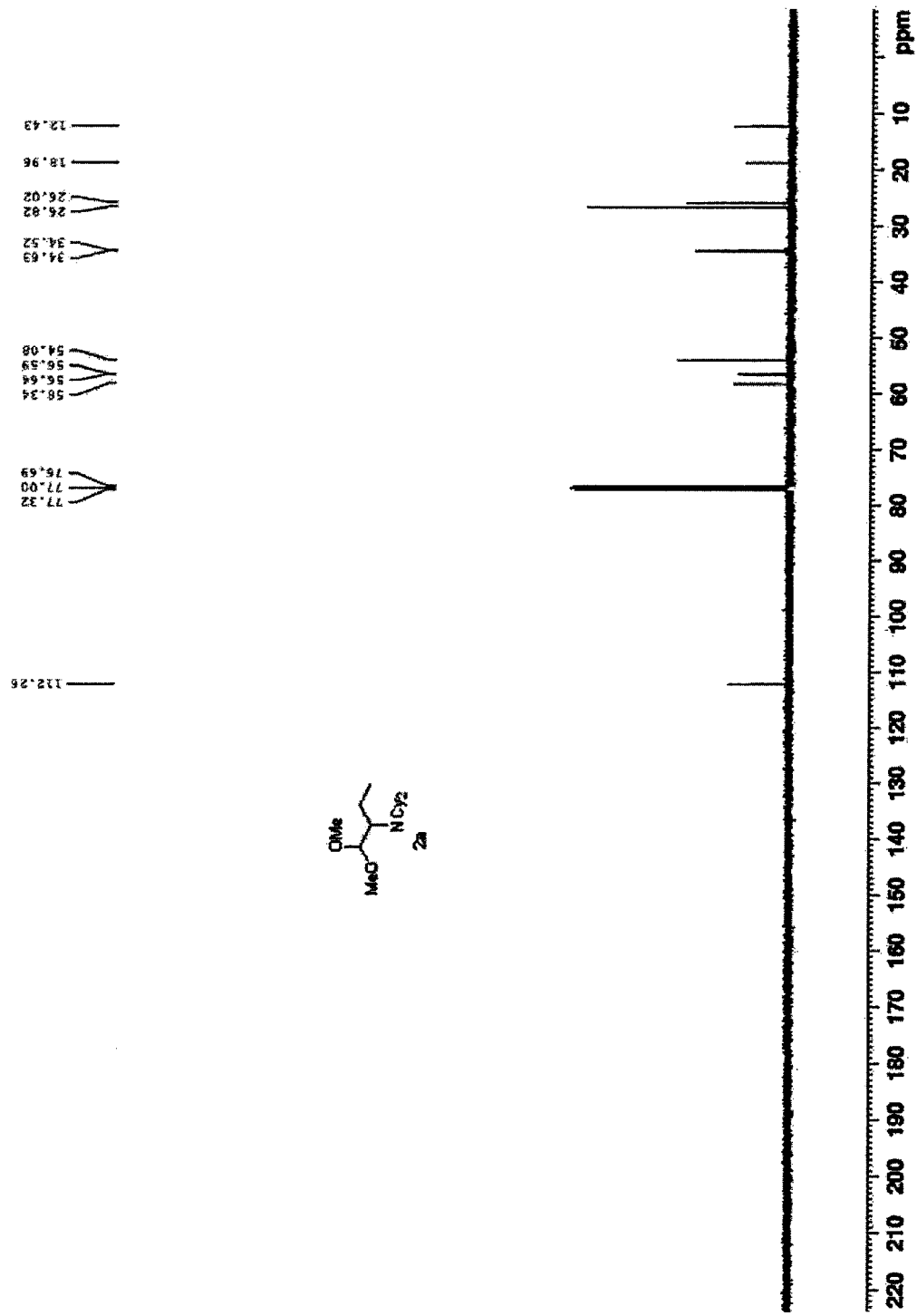
Figure 10A:
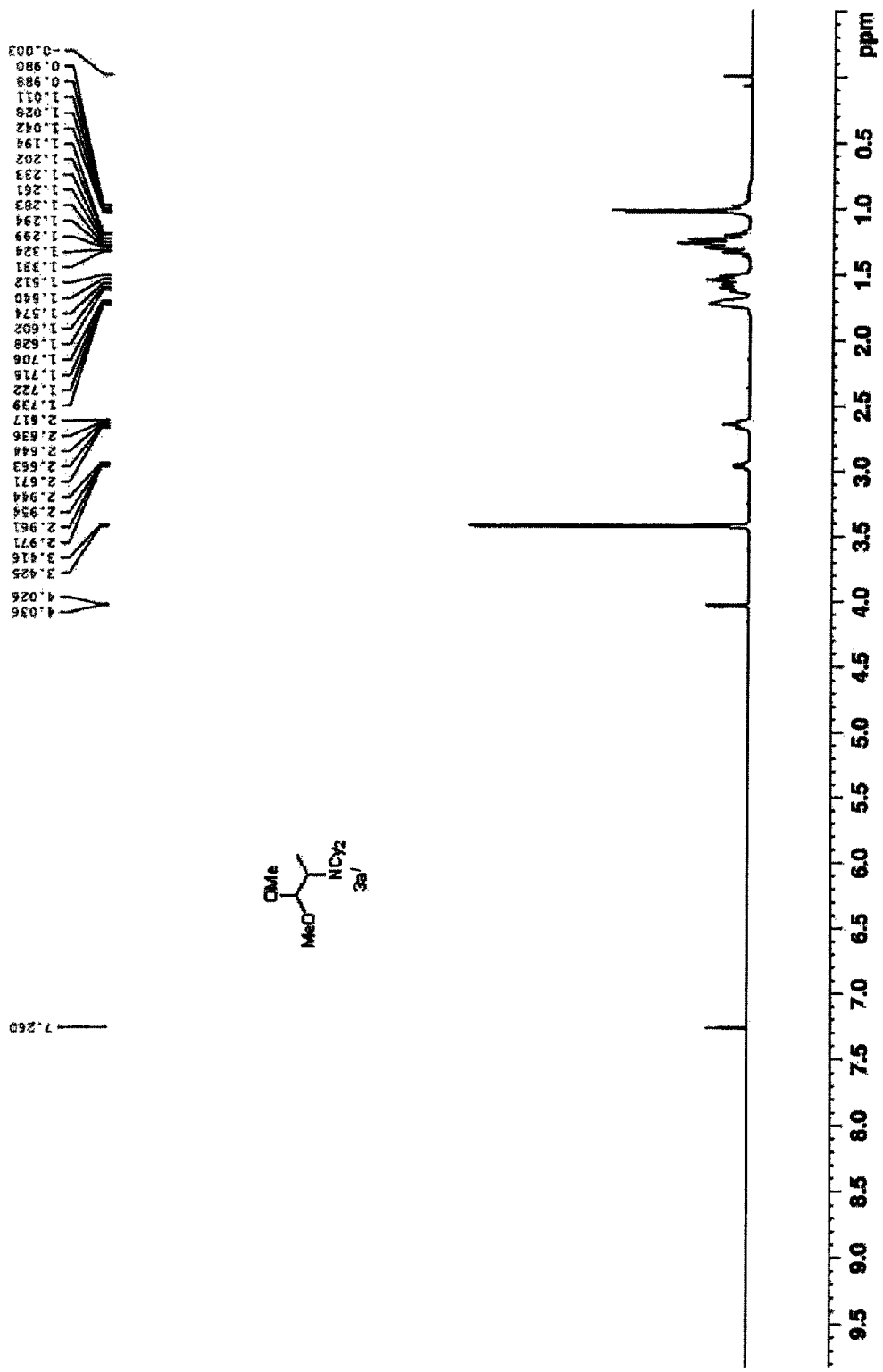
FIGS. 10(A) and (B) show, respectively, the $^1$H NMR and $^{13}$C NMR spectra of N-cyclohexyl-N-(1,1-dimethoxypropan-2-yl)cyclohexanamine (3a') of Example 1.
Figure 10B:
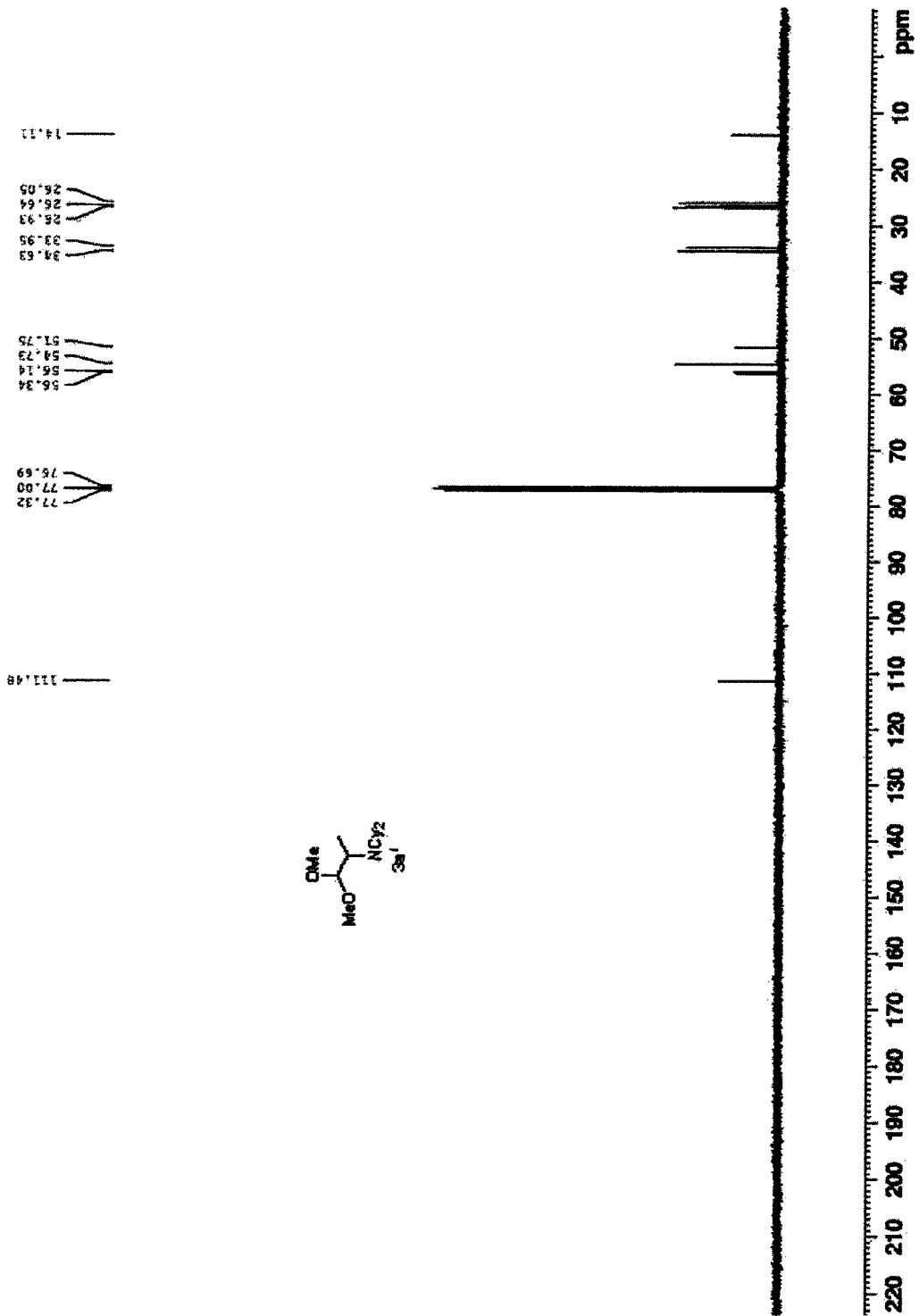
Figure 11A:
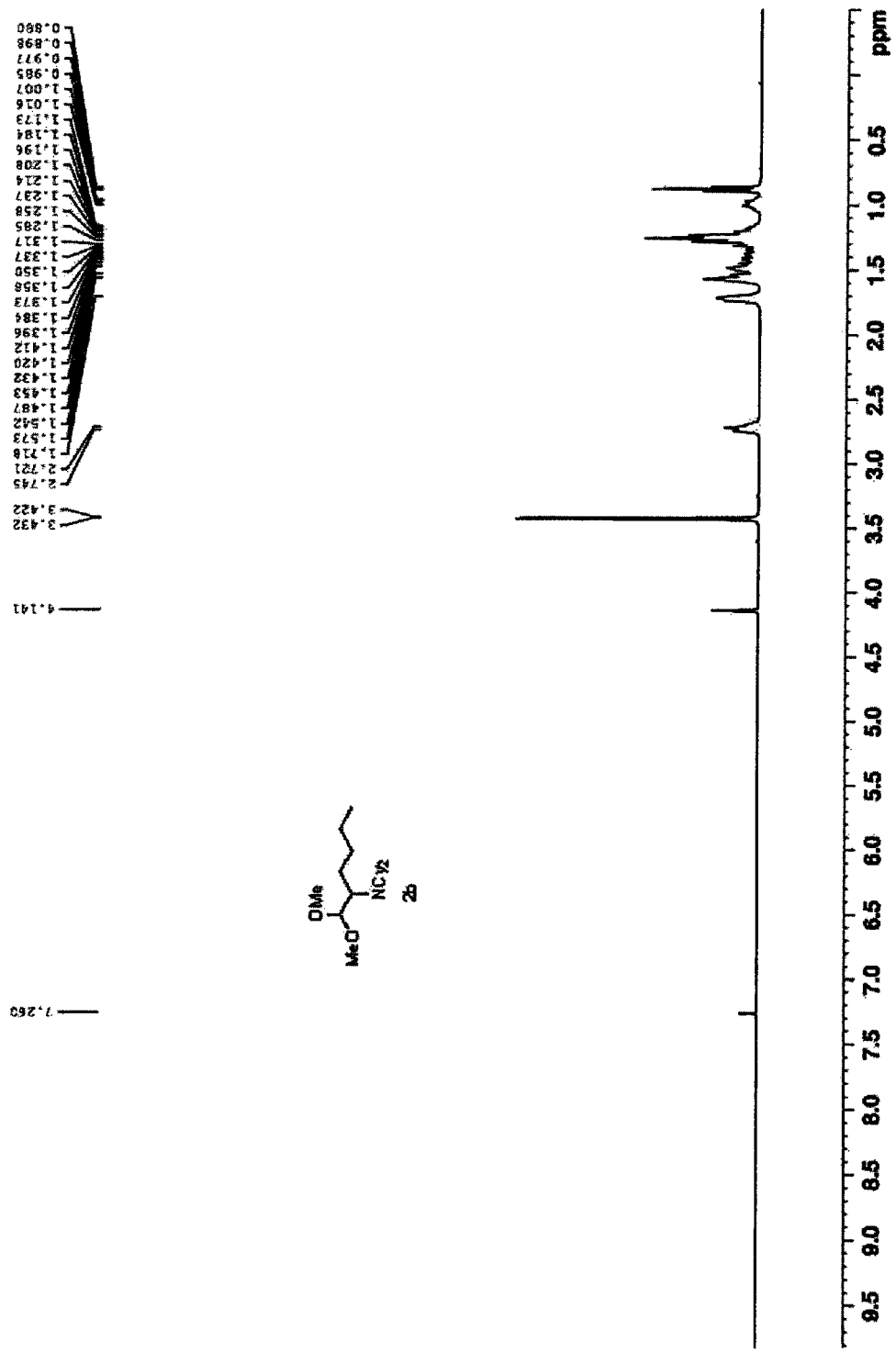
FIGS. 11(A) and (B) show, respectively, the $^1$H NMR and $^{13}$C NMR spectra of N-cyclohexyl-N-(1,1-dimethoxyhexan-2-yl)cyclohexanamine (2b) of Example 1.
Figure 11B:
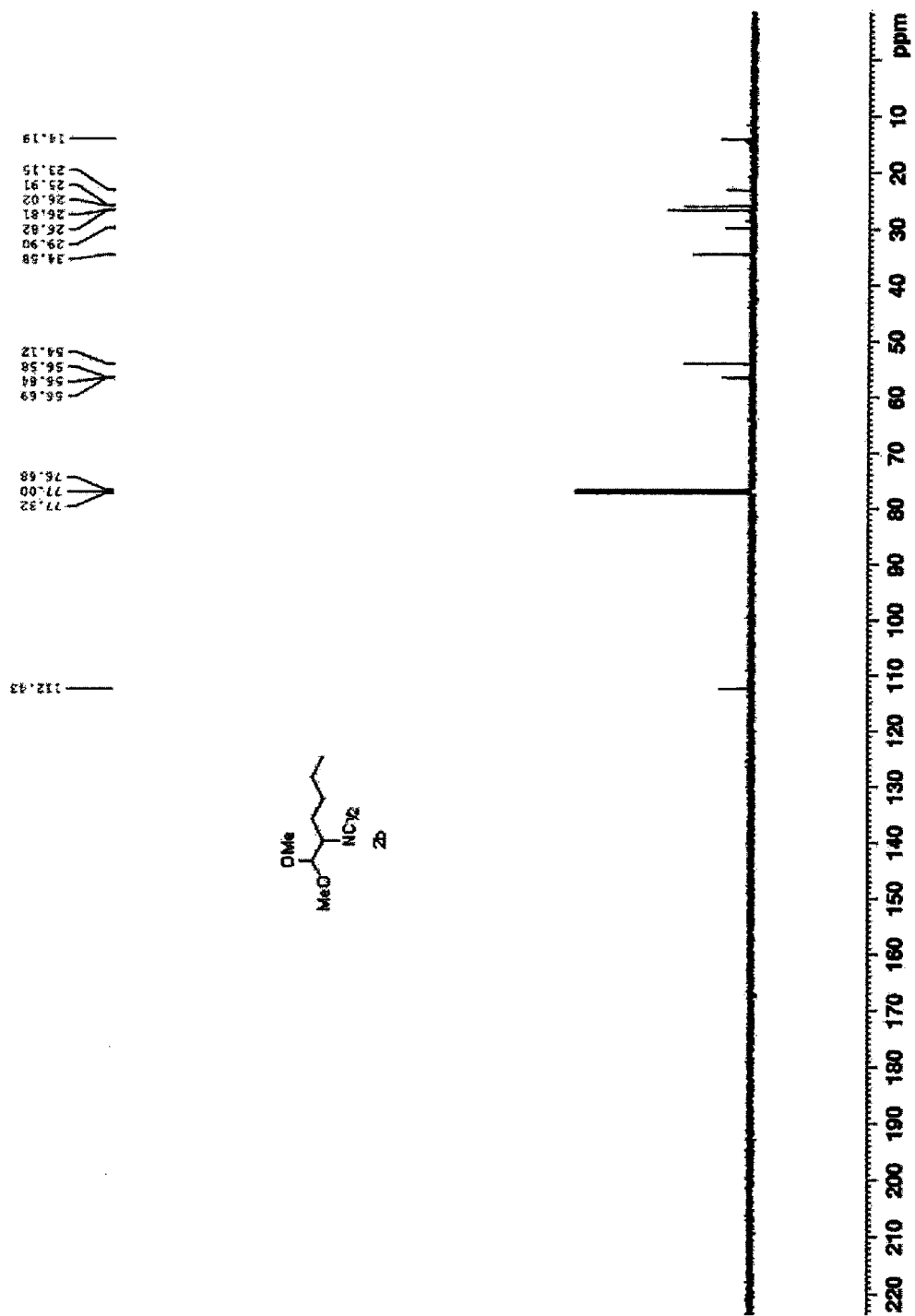
Figure 12A:
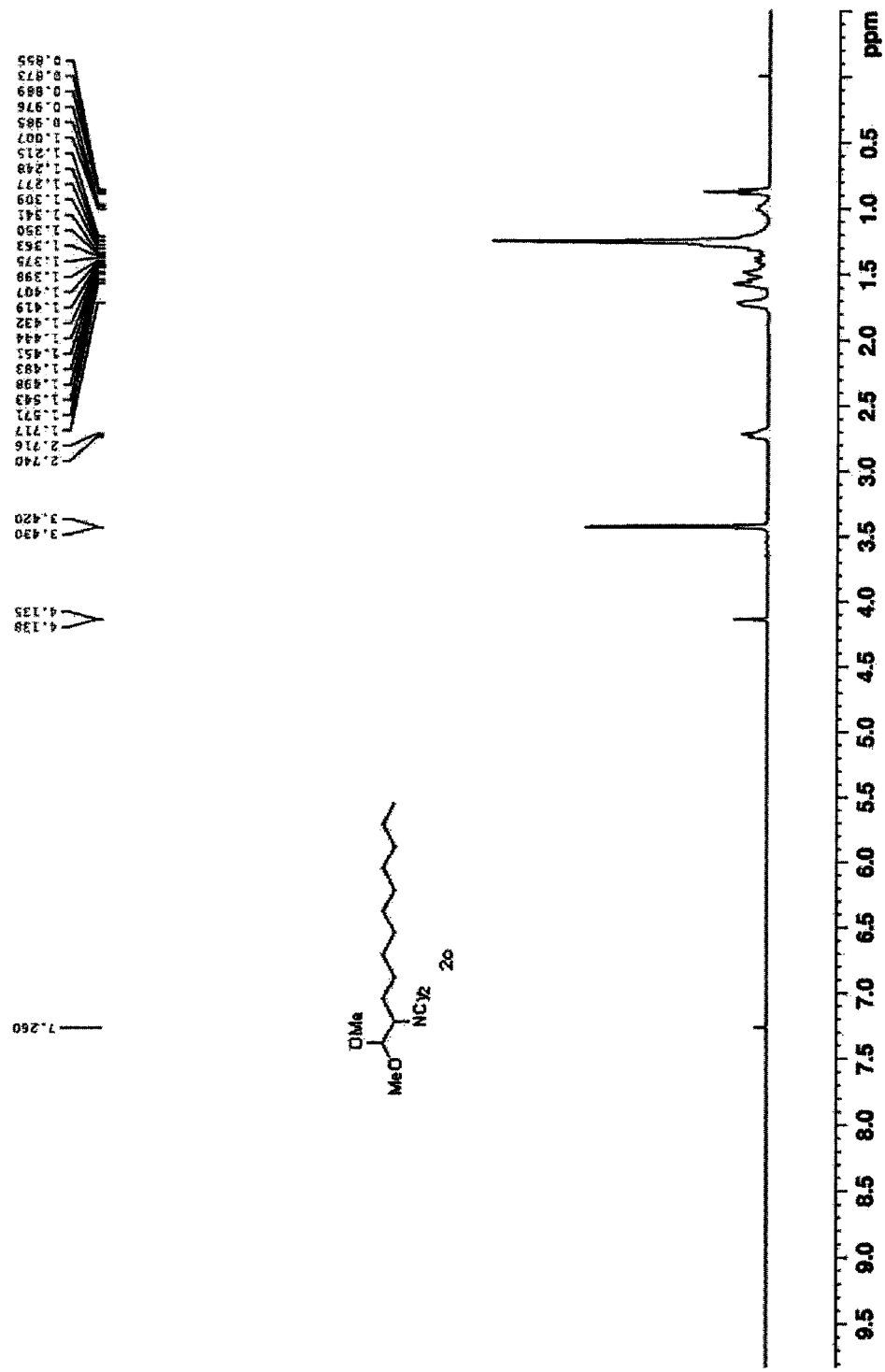
FIGS. 12(A) and (B) show, respectively, the $^1$H NMR and $^{13}$C NMR spectra of N-cyclohexyl-N-(1,1-dimethoxydodecan-2-yl)cyclohexanamine (2c) of Example 1.
Figure 12B:
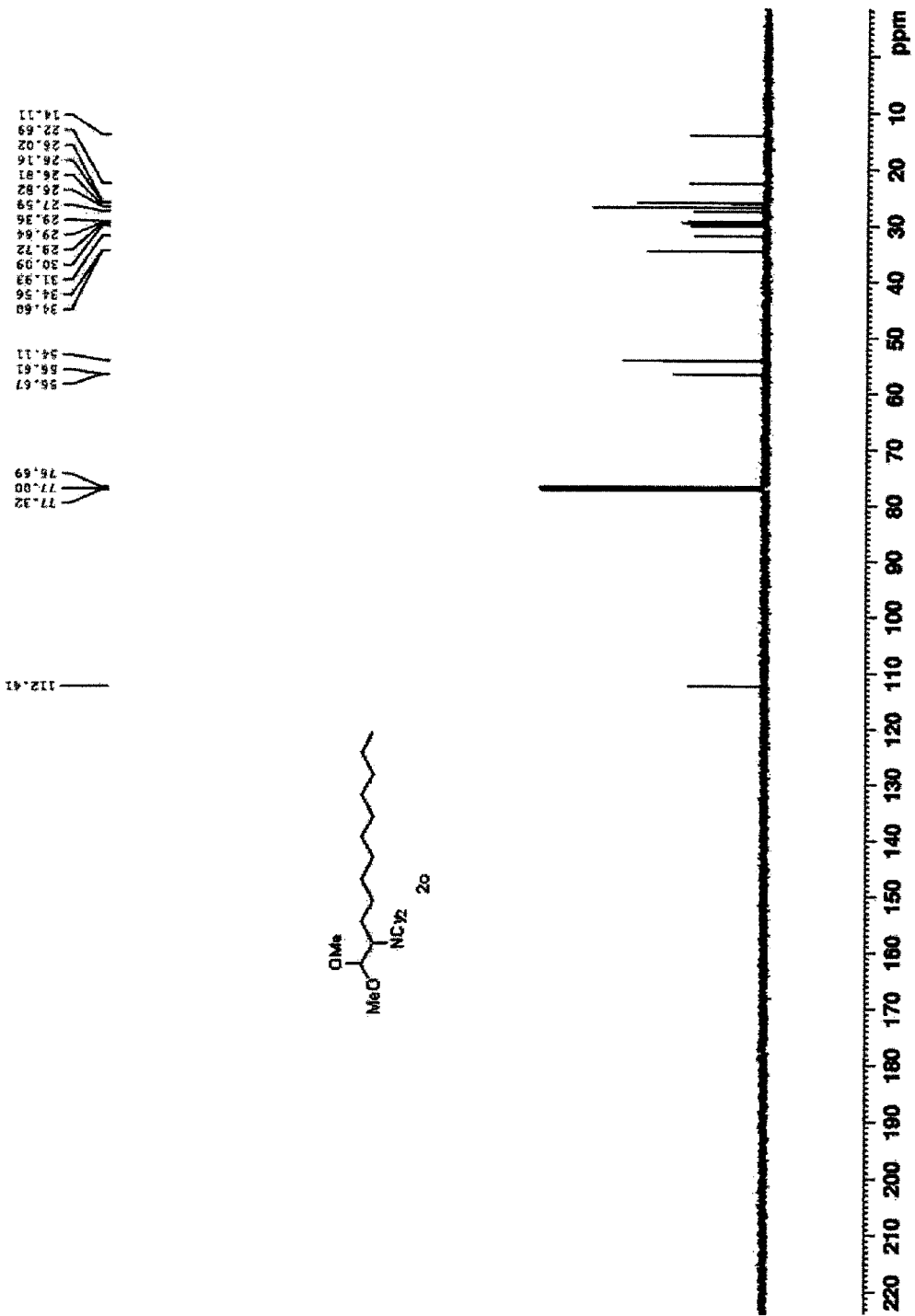
Figure 13A:
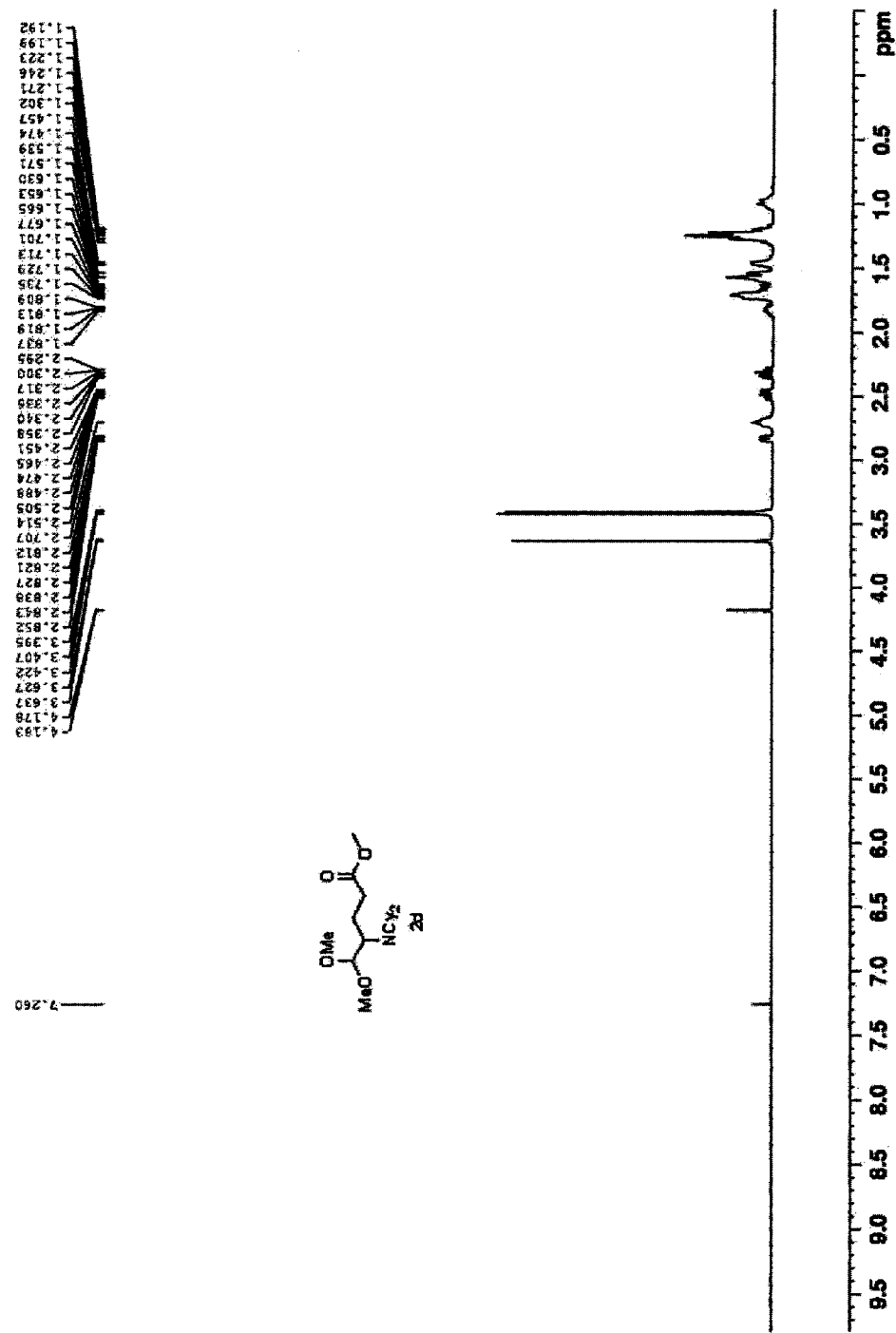
FIGS. 13(A) and (B) show, respectively, the $^1$H NMR and $^{13}$C NMR spectra of methyl 4-(dicyclohexylamino)-5,5-dimethoxypentanoate (2d) of Example 1.
Figure 13B:
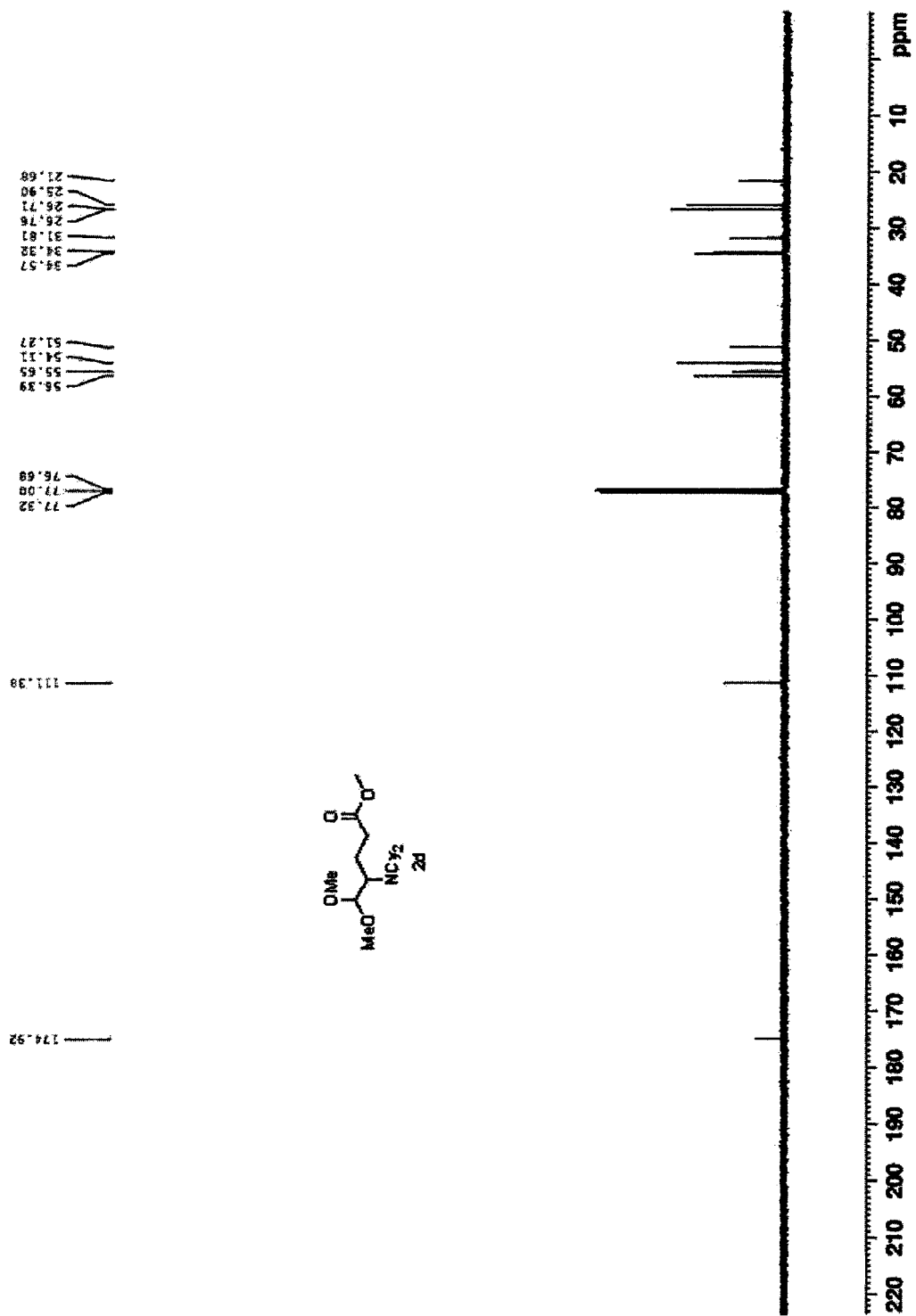
Figure 14A:
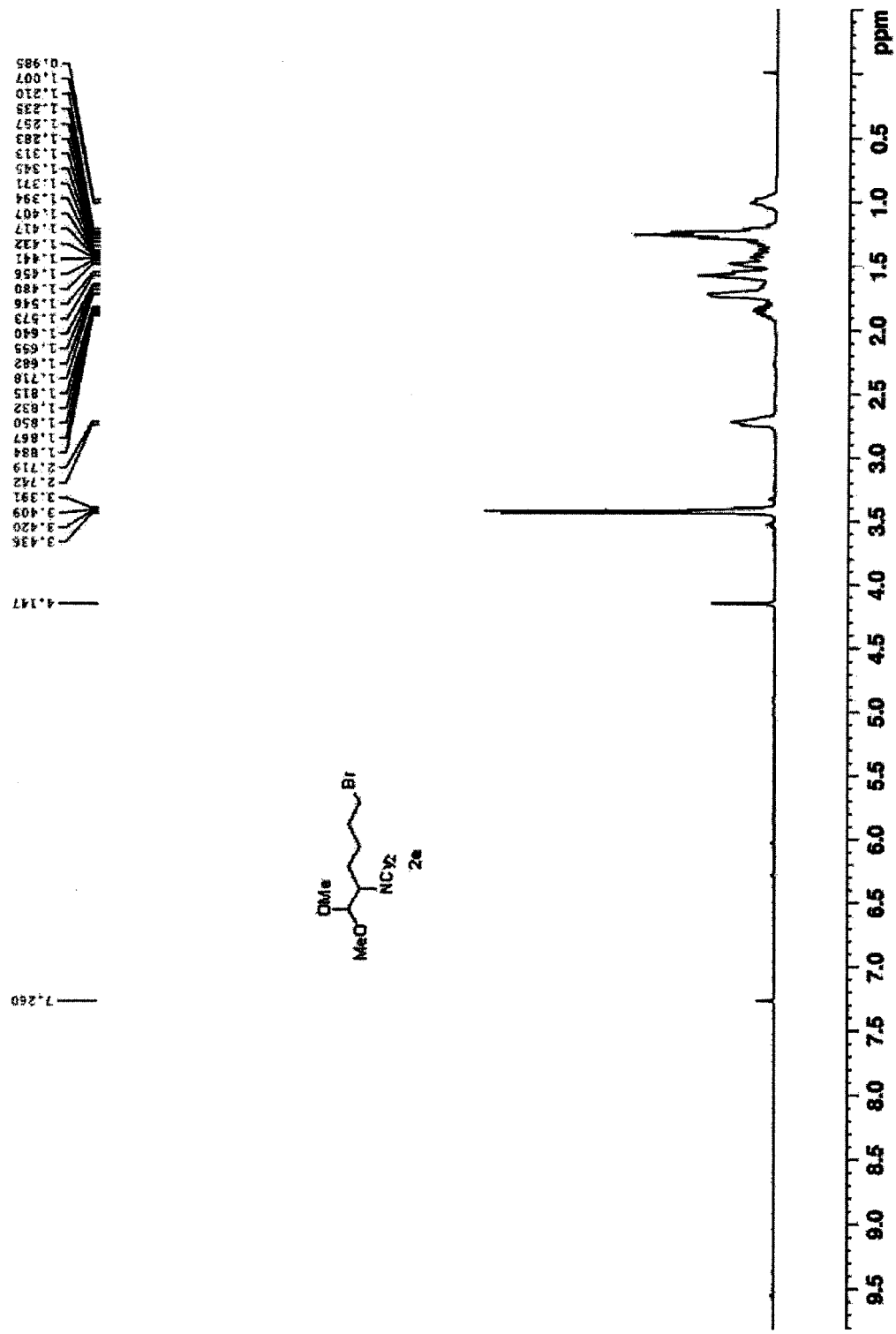
FIGS. 14(A) and (B) show, respectively, the $^1$H NMR and $^{13}$C NMR spectra of N-(6-bromo-1,1-dimethoxyhexan-2-yl)-N-cyclohexylcyclohexanamine (2e) of Example 1.
Figure 14B:
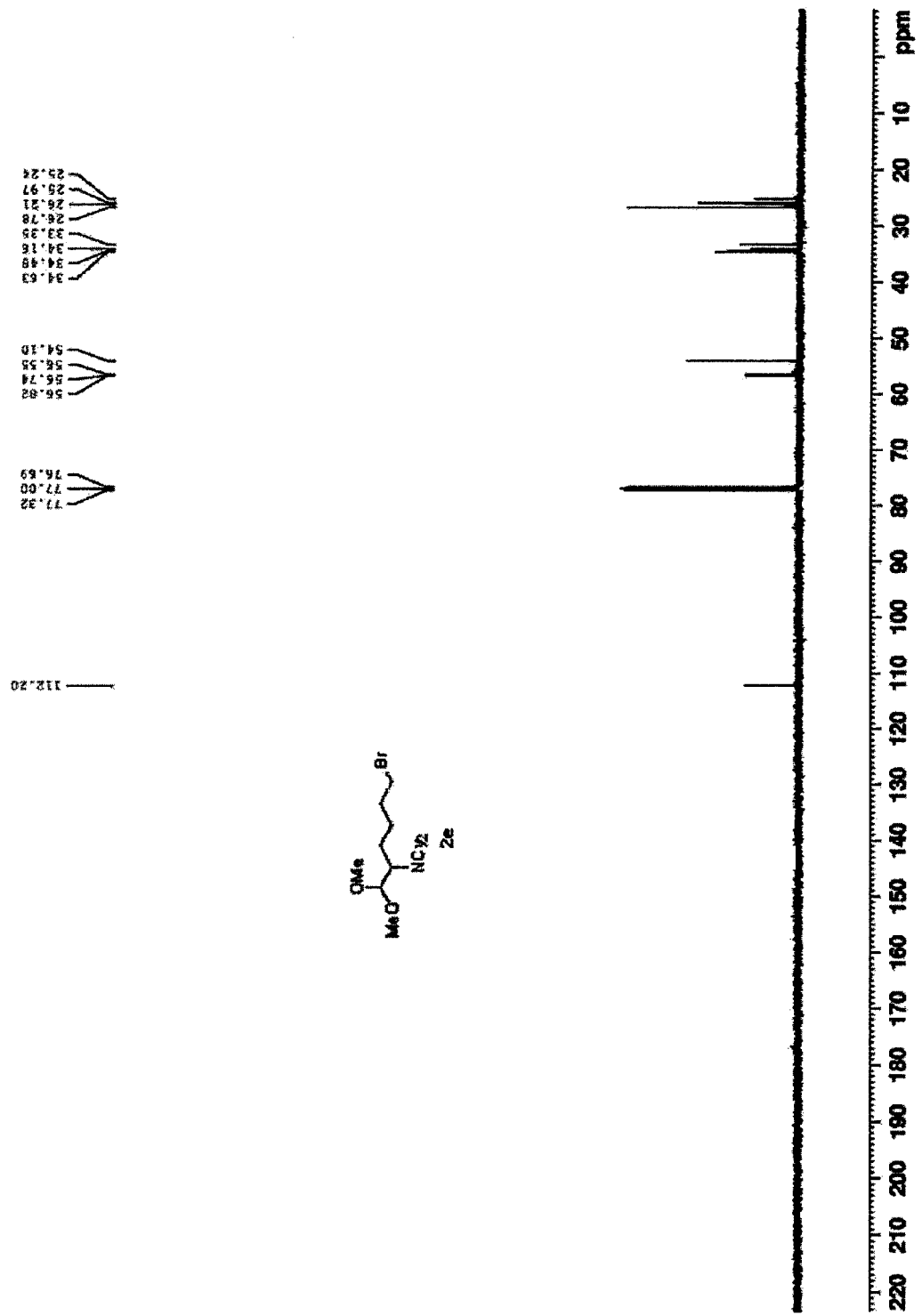
Figure 15A:
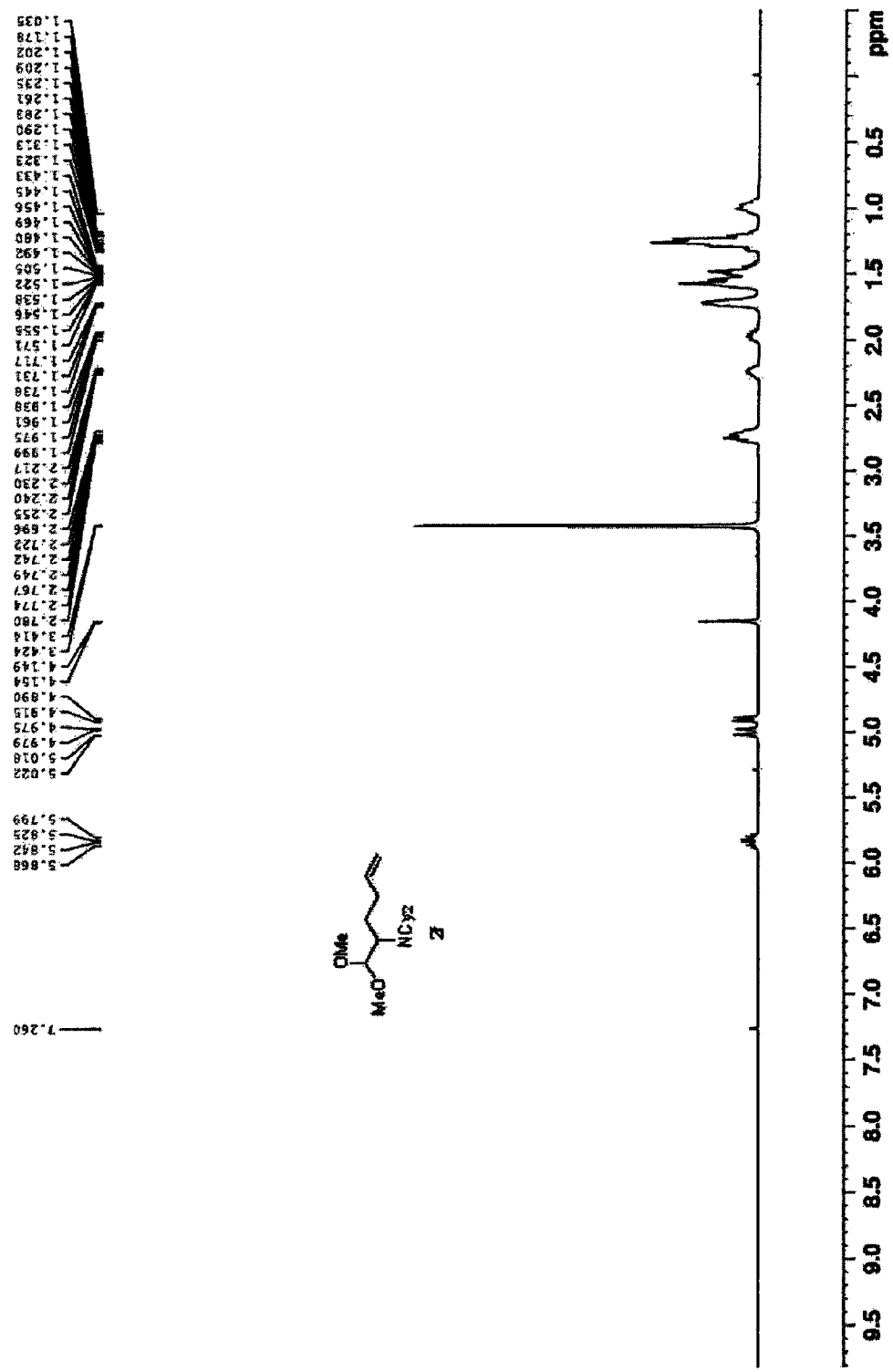
FIGS. 15(A) and (B) show, respectively, the $^1$H NMR and $^{13}$C NMR spectra of N-cyclohexyl-N-(1,1-dimethoxyhex-5-en-2-yl)cyclohexanamine (2f) of Example 1.
Figure 15B:
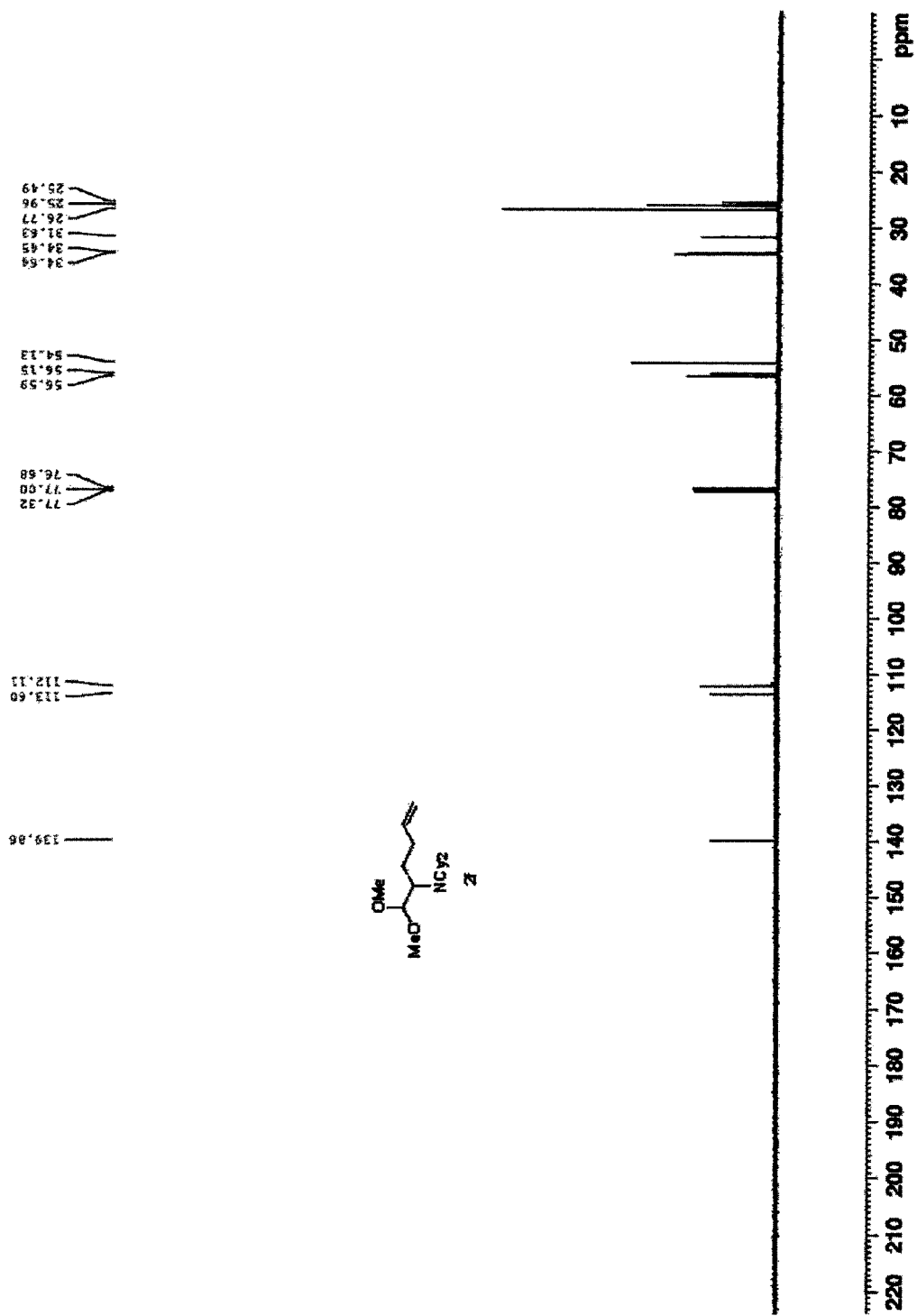
Figure 16A:
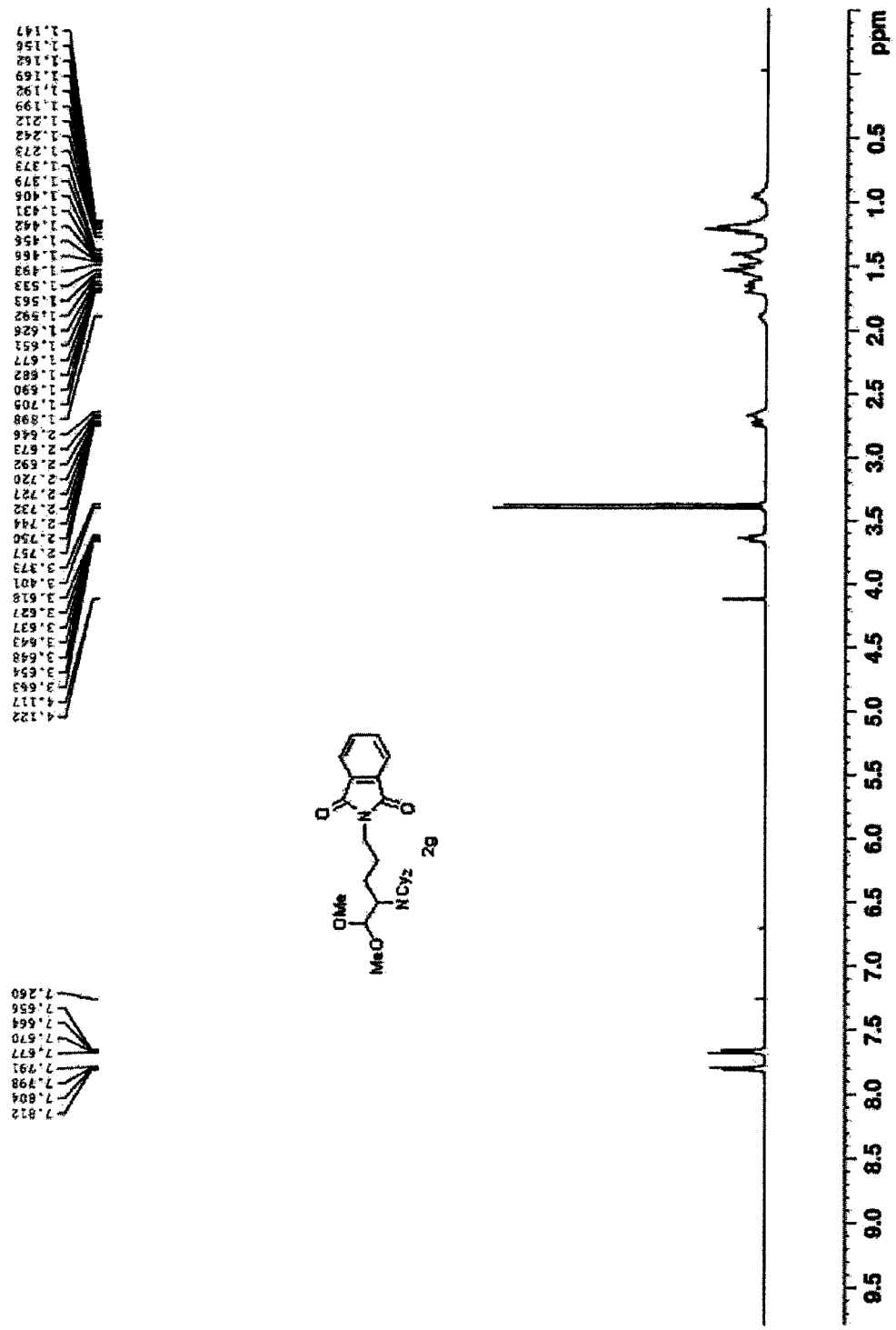
FIGS. 16(A) and (B) show, respectively, the $^1$H NMR and $^{13}$C NMR spectra of 2-(4-(dicyclohexylamino)-5,5-dimethoxypentyl)isoindoline-1,3-dione (2g) of Example 1.
Figure 16B:
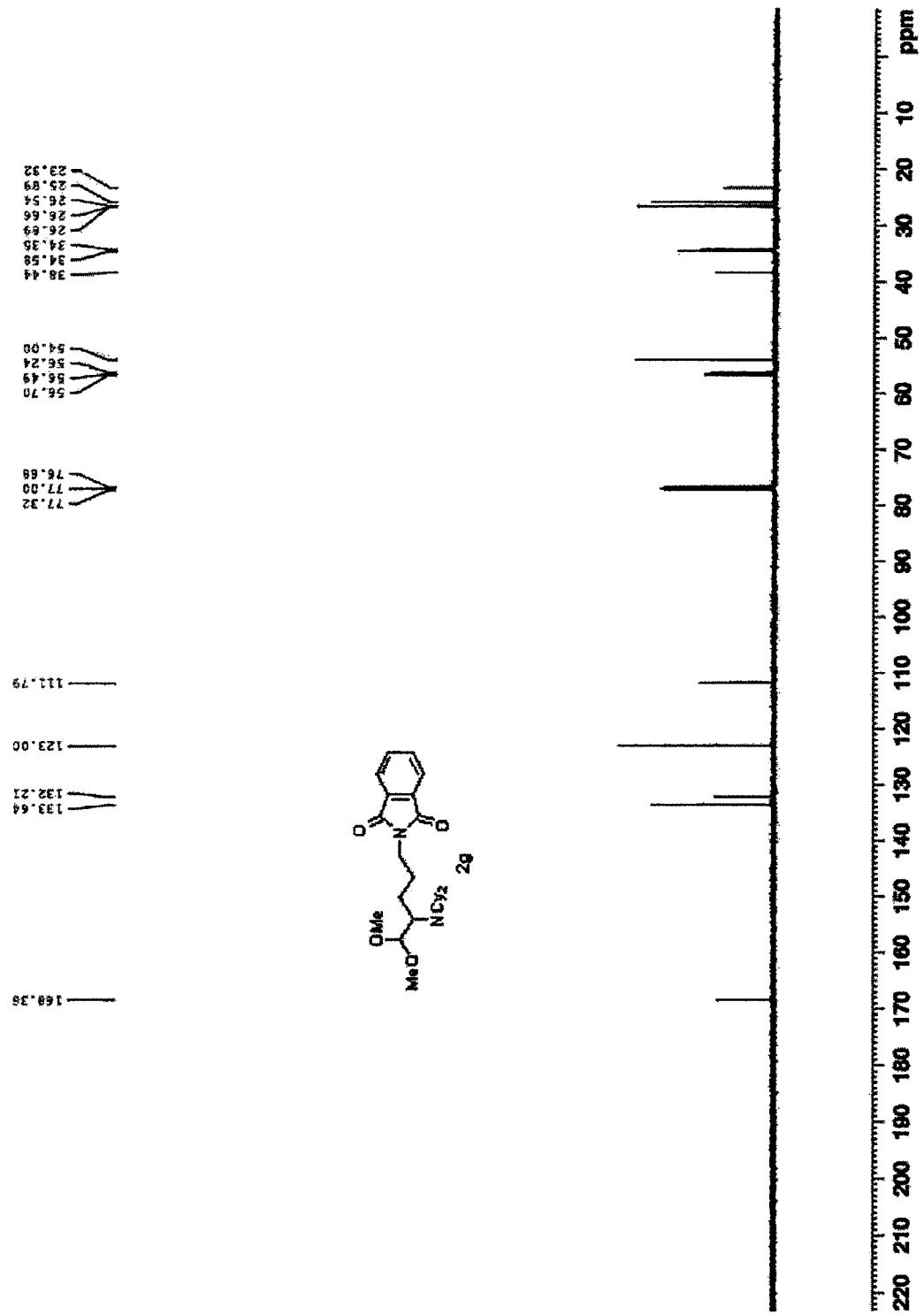
Figure 17A:
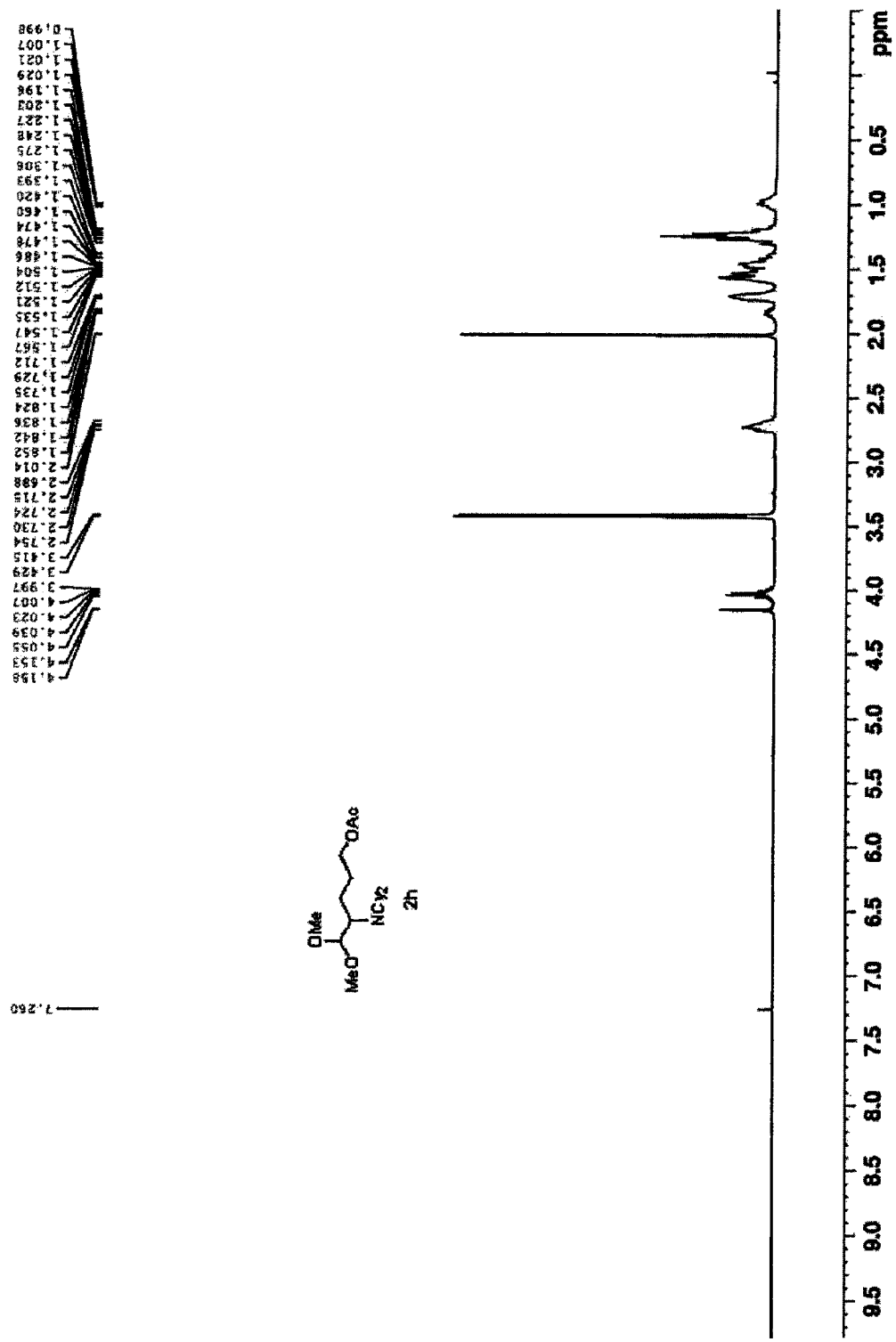
FIGS. 17(A) and (B) show, respectively, the $^1$H NMR and $^{13}$C NMR spectra of 4-(dicyclohexylamino)-5,5-dimethoxypentyl acetate (2h) of Example 1.
Figure 17B:
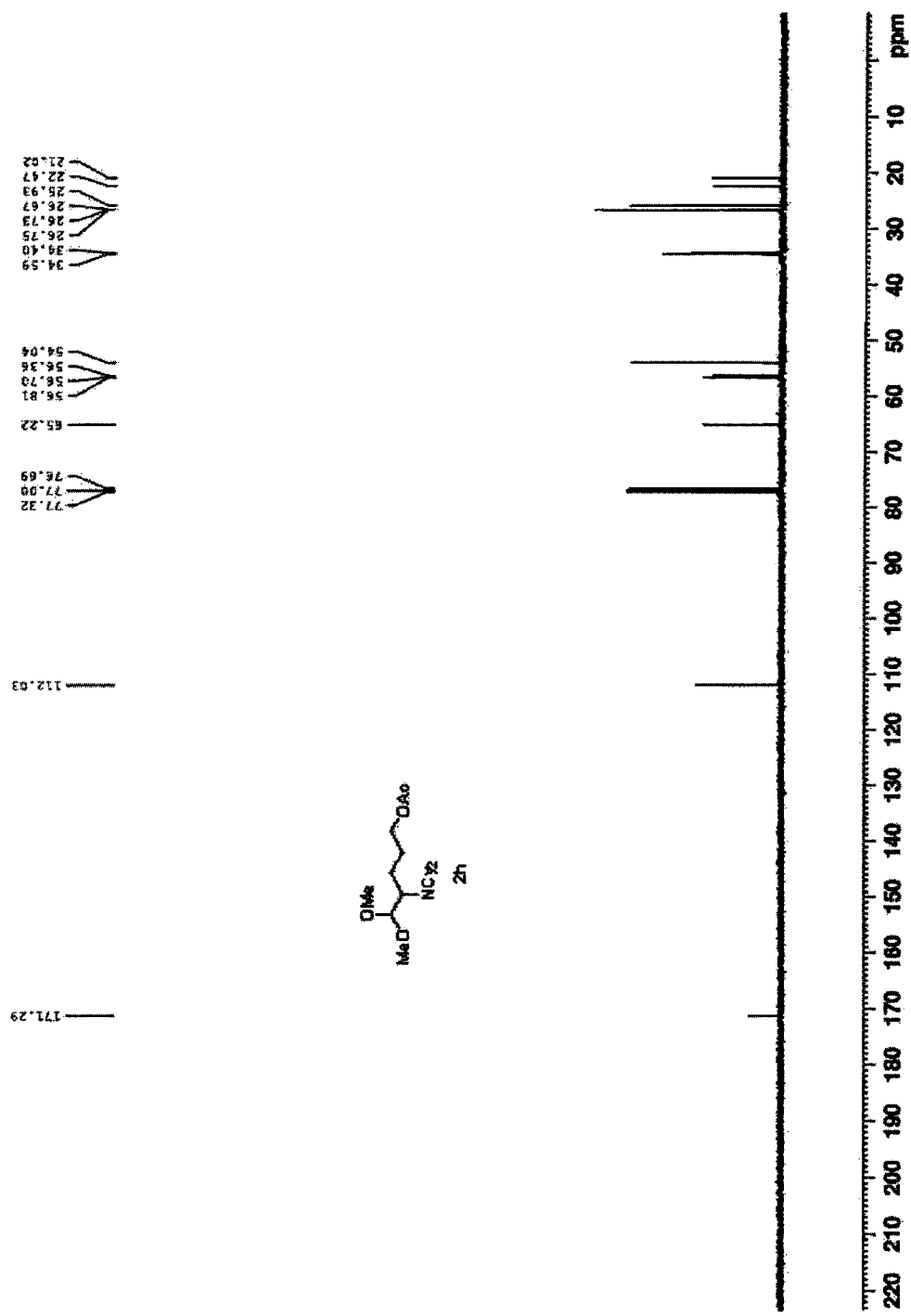
Figure 18A:
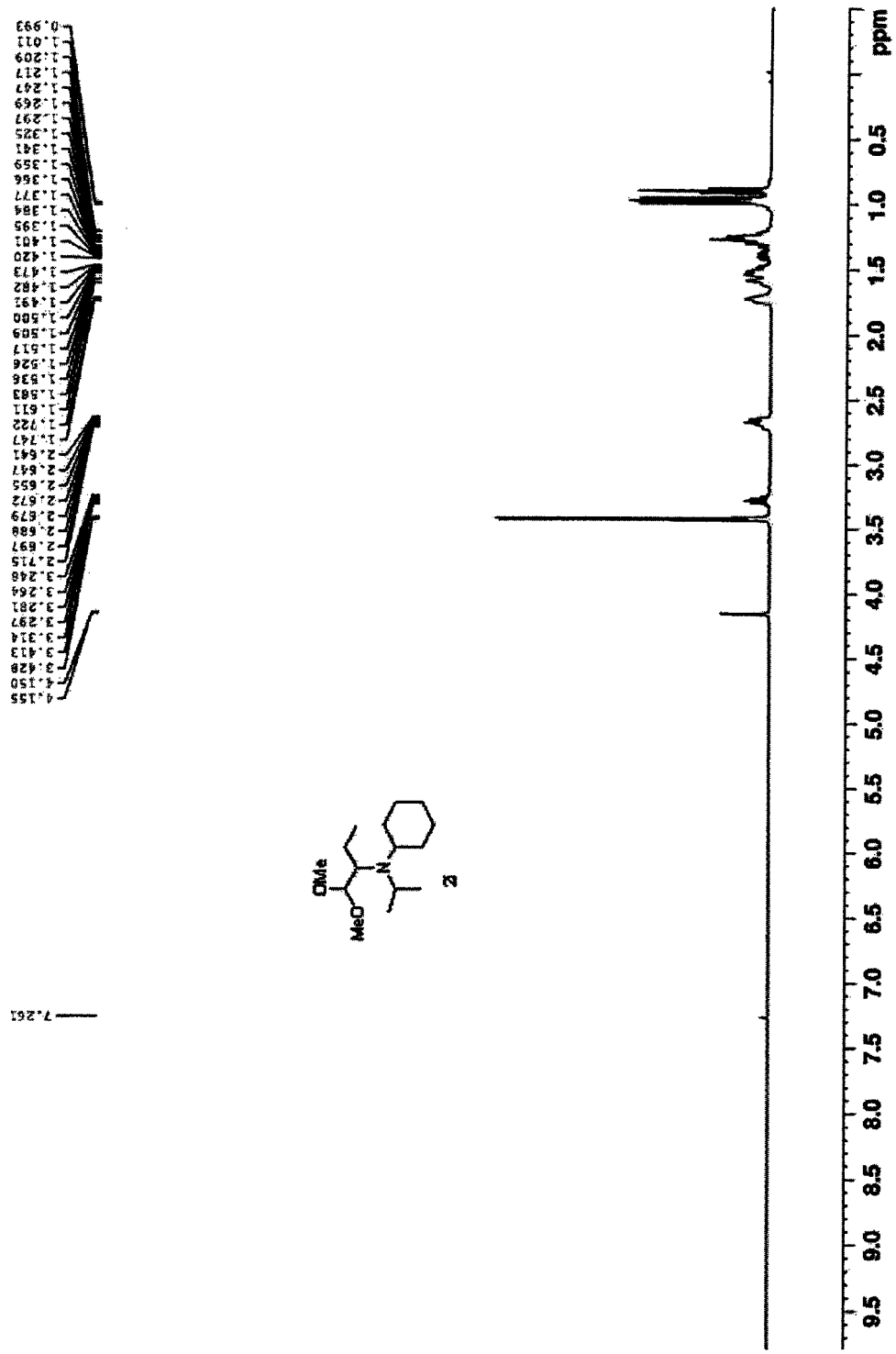
FIGS. 18(A) and (B) show, respectively, the $^1$H NMR and $^{13}$C NMR spectra of N-(1,1-dimethoxybutan-2-yl)-N-isopropylcyclohexanamine (2i) of Example 1.
Figure 18B:
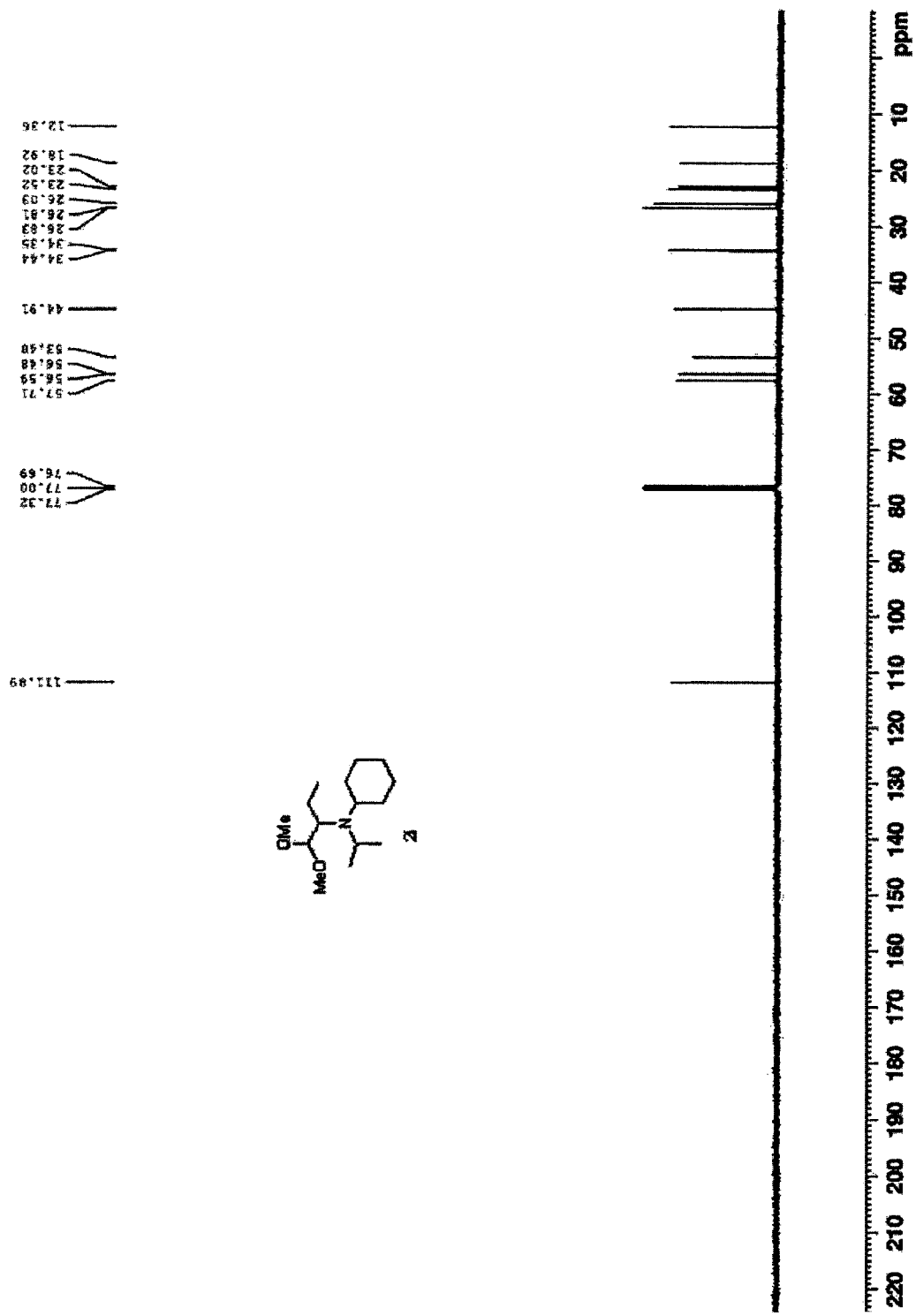
Figure 19A:
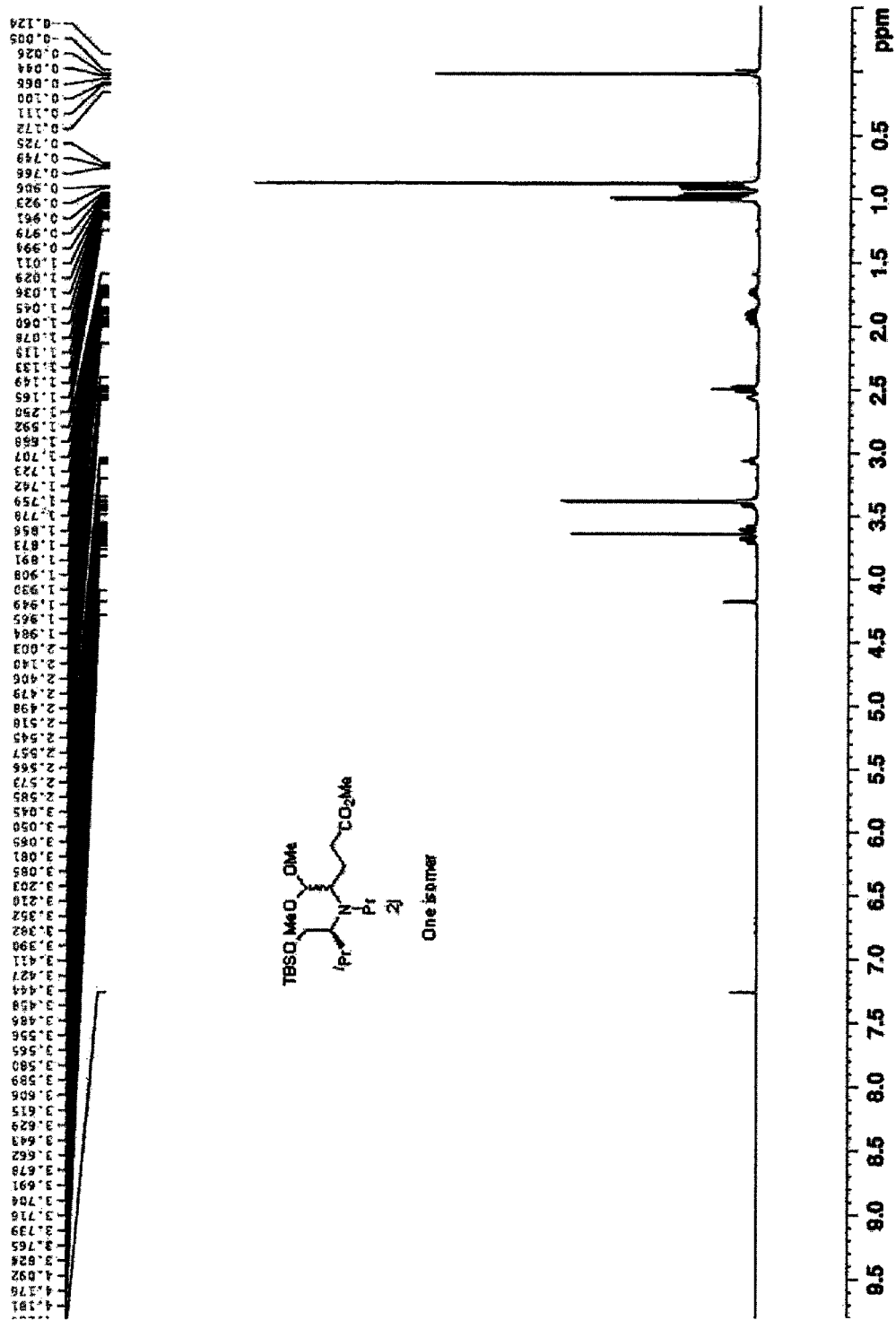
FIGS. 19(A) and (B) show, respectively, the $^1$H NMR and $^{13}$C NMR spectra of a first isomer of methyl 4-(((S)-1-(tert-butyldimethylsilyloxy)-3-methylbutan-2-yl)(isopropyl) amino)-5,5-dimethoxypentanoate (2j) of Example 1.
Figure 19B:
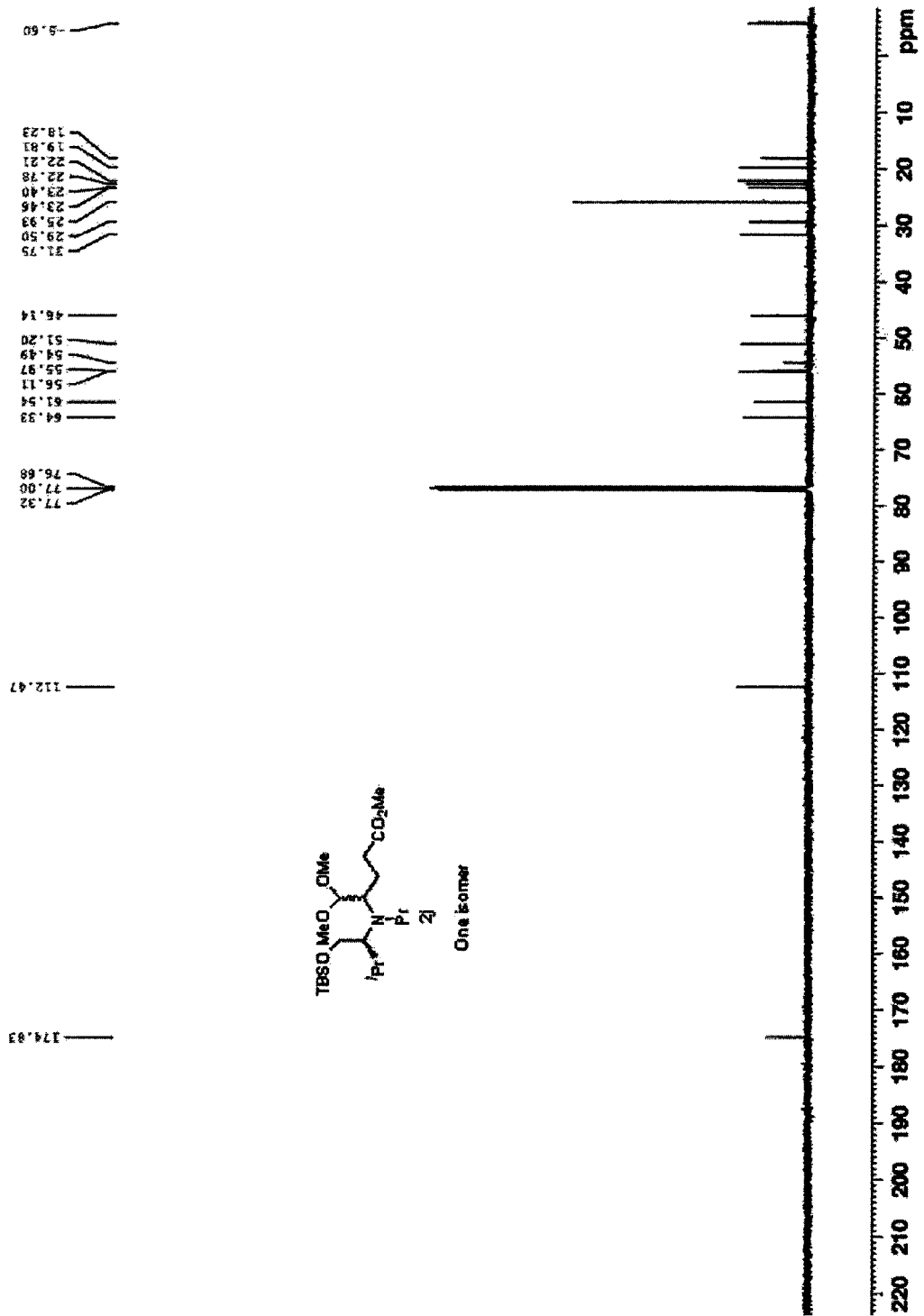
Figure 20A:
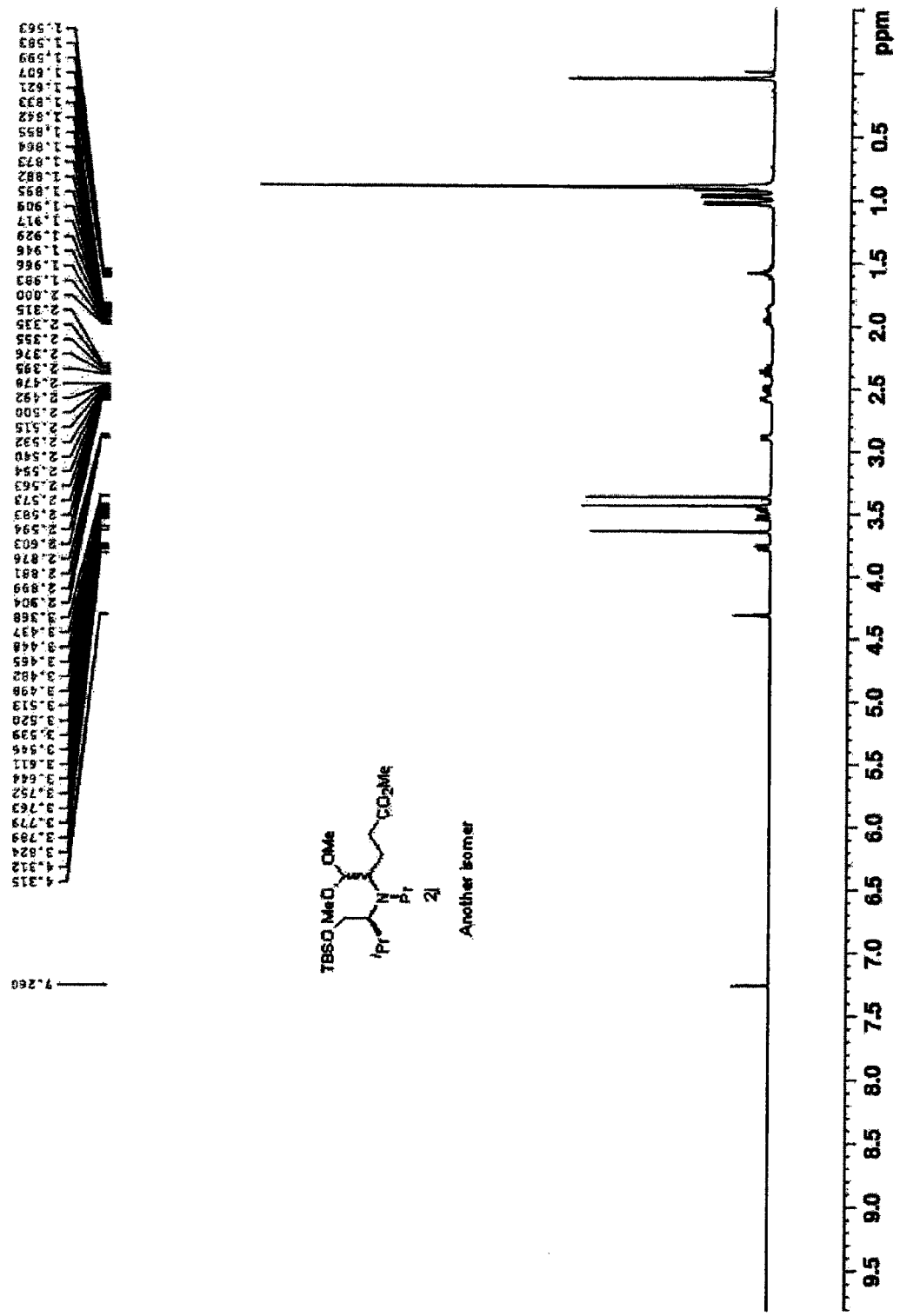
FIGS. 20(A) and (B) show, respectively, the $^1$H NMR and $^{13}$C NMR spectra of a second isomer of methyl 4-(((S)-1-
Figure 20B:
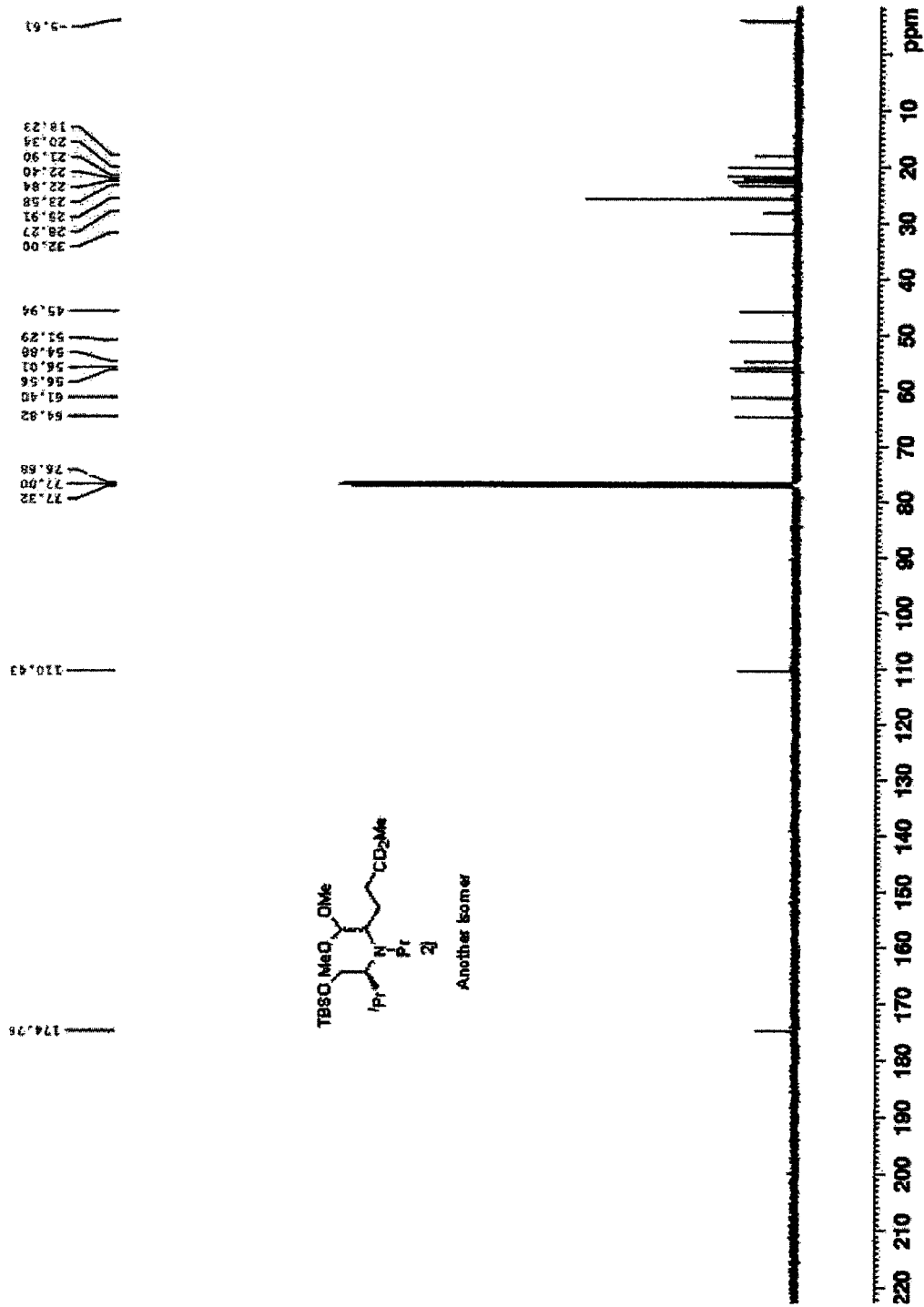

To demonstrate the hypothesis that iminium ion and enamine, and the aziridinium ion with three-membered ring were thought to be the important intermediates for direct synthesis of α-amino acetals from secondary amine and aliphatic aldehydes, some experiments were carried out. Firstly, two deuterated labeling experiments were performed using CD$_3$OD instead of MeOH (Scheme 8, eqs. 1-2, FIG. 6), which affords similar results with the synthesis α-amino acetals via oxidative rearrangement of tertiary amine. Interestingly, α-methyl aliphatic aldehyes was used for this reaction, no desired product was obtained (Scheme 8, eq. 3, FIG. 6).

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A method for the synthesis of an α-amino acetal, comprising
    (i) oxidizing a tertiary amine in the presence of a copper catalyst, at least one oxidant and a solvent, or
    (ii) reacting a secondary amine and an aliphatic aldehyde in the presence of a copper catalyst, at least one oxidant and a solvent.

2. The method of claim 1 for the synthesis of an α-amino acetal of formula I,

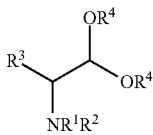

Formula I wherein the method comprises oxidizing a tertiary amine of formula II

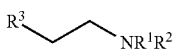

Formula II in the presence of a copper catalyst, one or more alcohols of formula $R^4OH$, at least one oxidant and a solvent,
wherein each $R^1$, $R^2$, $R^3$, and $R^4$ is independently selected from the group consisting of substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ cycloalkyl, substituted or unsubstituted $C_3$-$C_{20}$ heterocycloalkyl, substituted or unsubstituted $C_3$-$C_{20}$ cycloalkenyl, and substituted or unsubstituted $C_3$-$C_{20}$ heterocycloalkenyl.

3. The method of claim 1 for the synthesis of an α-amino acetal of formula I,

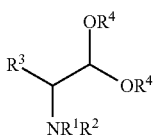

Formula I wherein the method comprises reacting a secondary amine of formula III $HNR^1R^2$   Formula III with an aliphatic aldehyde of formula IV

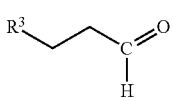

Formula IV in the presence of a copper catalyst, one or more alcohols of formula $R^4OH$, at least one oxidant and a solvent,
wherein each $R^1$, $R^2$, $R^3$, and $R^4$ is independently selected from the group consisting of substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ cycloalkyl, substituted or unsubstituted $C_3$-$C_{20}$ heterocycloalkyl, substituted or unsubstituted $C_3$-$C_{20}$ cycloalkenyl, and substituted or unsubstituted $C_3$-$C_{20}$ heterocycloalkenyl.

4. The method of claim 1 for the synthesis of an α-amino acetal of formula I,

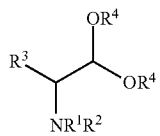

Formula I wherein the method comprises oxidizing an enamine of formula V

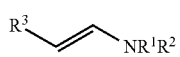

Formula V in the presence of a copper catalyst, one or more alcohols of formula $R^4OH$, at least one oxidant and a solvent,
wherein each $R^1$, $R^2$, $R^3$, and $R^4$ is independently selected from the group consisting of substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ cycloalkyl, substituted or unsubstituted $C_3$-$C_{20}$ heterocycloalkyl, substituted or unsubstituted $C_3$-$C_{20}$ cycloalkenyl, and substituted or unsubstituted $C_3$-$C_{20}$ heterocycloalkenyl.

5. The method of claim 1, wherein the reaction is carried out in the presence of a nitrogen donor ligand.

6. The method of claim 5, wherein the nitrogen donor ligand is N,N,N',N'-tetramethylethylenediamine (TMEDA).

7. The method of claim 6, wherein the molar ratio of copper catalyst:TMEDA is between about 1:1 and about 1:5.

8. The method of claim 7, wherein the molar ratio of copper catalyst:TMEDA is about 1:2.

9. The method of claim 1, wherein the copper catalyst is copper (II) halide or copper (I) halide.

10. The method of claim 9, wherein the halide is iodide, bromide or chloride.

11. The method of claim 10, wherein the copper catalyst is selected from the group consisting of $CuBr_2$, $CuI_2$, CuI, and CuBr.

12. The method of claim 2, wherein the copper catalyst is $CuBr_2$ or $CuI_2$.

13. The method of claim 3, wherein the copper catalyst is CuI, CuBr or $CuBr_2$.

14. The method of claim 1, wherein the one or more alcohols are methanol or ethanol.

15. The method of claim 1, wherein the solvent is an organic solvent selected from the group consisting of acetonitrile (MeCN), methanol (MeOH), 1,2-dichloroethane (DCE), tetrahydrofuran (THF), dimethyl sulfoxide (DMSO), and mixtures thereof.

16. The method of claim 15, wherein the solvent comprises a mixture of MeOH and MeCN.

17. The method of claim 16, wherein the solvent comprises a volume ratio of MeOH:MeCN in a range of between about 1:1 and about 1:10.

18. The method of claim 1, wherein the oxidant is selected from the group consisting of air, oxygen, a peroxide, and a mixture thereof.

19. The method of claim 18, wherein the peroxide is selected from the group consisting of tert-butyl hydroperoxide, di-tert-butyl peroxide, tert-butyl benzoylperoxide, and a mixture thereof.

* * * * *